(12) United States Patent
Austin et al.

(10) Patent No.: US 12,643,099 B2
(45) Date of Patent: Jun. 2, 2026

(54) DEVICES AND METHODS FOR CYTOGENETIC ANALYSIS

(71) Applicants: DIMENSIONGEN, Grand Cayman (KY); Dimension Genomics Inc, San Diego, CA (US)

(72) Inventors: Michael David Austin, San Diego, CA (US); Han Cao, San Diego, CA (US)

(73) Assignees: DIMENSIONGEN, Grand Cayman (KY); Dimension Genomics Inc

( * ) Notice: Subject to any disclaimer, the term of this patent is extended or adjusted under 35 U.S.C. 154(b) by 615 days.

(21) Appl. No.: 17/928,377

(22) PCT Filed: May 28, 2021

(86) PCT No.: PCT/US2021/034754
§ 371 (c)(1),
(2) Date: Nov. 29, 2022

(87) PCT Pub. No.: WO2021/247394
PCT Pub. Date: Dec. 9, 2021

(65) Prior Publication Data
US 2023/0321653 A1      Oct. 12, 2023

Related U.S. Application Data

(60) Provisional application No. 63/143,857, filed on Jan. 31, 2021, provisional application No. 63/087,131, (Continued)

(51) Int. Cl.
*B01L 3/00*        (2006.01)
*B01F 33/302*      (2022.01)
(Continued)

(52) U.S. Cl.
CPC ........ *B01L 3/50273* (2013.01); *C12Q 1/6874* (2013.01); *B01L 2300/16* (2013.01)

(58) Field of Classification Search
CPC ............. B01L 3/50273; B01L 2300/16; C12Q 1/6874
See application file for complete search history.

(56) References Cited

U.S. PATENT DOCUMENTS

2016/0369331 A1*  12/2016  Saghbini ................ G16B 20/00
2017/0073666 A1*   3/2017  Stedman .............. C12Q 1/6806

FOREIGN PATENT DOCUMENTS

WO        2013036860 A1    3/2013
WO        2013088098 A2    6/2013
(Continued)

OTHER PUBLICATIONS

Lam, Ernest T., et al. "Genome mapping on nanochannel arrays for structural variation analysis and sequence assembly." Nature biotechnology 30.8 (2012): 771-776. (Year: 2012).*
(Continued)

*Primary Examiner* — Jennifer Wecker
*Assistant Examiner* — Oyeleye Alexander Alabi
(74) *Attorney, Agent, or Firm* — Garrett H. Anderson

(57) ABSTRACT

Genome whole chromosome analysis is a critical gold standard method for clinicians to study molecular lesions at single cell level in diseases and cancers. However, they suffer from low-sample-yielding, labor-intensive procedures that require subjective manual involvement of highly trained professionals. Here we disclose new devices, systems, and methods to automate, standardize, and accelerate the digital cytopathological sample and data generation with improved data quality to enable precision medicine and improve clinical practice. This disclosure describes a family of micro-fluidic devices, and accompanying methods for using said devices, to perform cytogenomic analysis on cells, nucleus, vesicles exosomes and their respective chromosomes, chromatins, nucleic acid polymers, subcellular genomic elements and any other dynamic transitional states between these forms. Collectively, these microfluidic
(Continued)

devices allow for the consistent physical manipulation and preparation of macromolecules to substantially improve the quality of the of the cytogenetic information being interrogated.

6 Claims, 29 Drawing Sheets

Related U.S. Application Data filed on Oct. 2, 2020, provisional application No. 63/032,984, filed on Jun. 1, 2020.

(51) Int. Cl.

| | |
|---|---|
| *B01F 33/3033* | (2022.01) |
| *B01L 7/00* | (2006.01) |
| *B33Y 80/00* | (2015.01) |
| *C12M 1/00* | (2006.01) |
| *C12M 1/34* | (2006.01) |
| *C12M 3/00* | (2006.01) |
| *C12M 3/06* | (2006.01) |
| *C12Q 1/6848* | (2018.01) |
| *C12Q 1/686* | (2018.01) |
| *C12Q 1/6874* | (2018.01) |
| *G01N 21/29* | (2006.01) |

(56)                 References Cited

FOREIGN PATENT DOCUMENTS

| WO | WO-2013158860 A1 * | 10/2013 | ........... C12Q 1/6816 |
|---|---|---|---|
| WO | 2015126840 A1 | 8/2015 | |
| WO | 2015134785 A1 | 9/2015 | |
| WO | 2017220637 A1 | 12/2017 | |

OTHER PUBLICATIONS

Abbyad, P., Dangla, R., Alexandrou, A., & Baroud, C. N. (2011). Rails and anchors: Guiding and trapping droplet microreactors in two dimensions. Lab on a Chip, 11(5), 813-821. website://doi.org/10.1039/c0lc00104j.

Mahshid S, Lu J, Abidi AA, Sladek R, Reisner WW, Ahamed MJ. Transverse dielectrophoretic-based DNA nanoscale confinement. Sci Rep. Apr. 13, 2018;8(1):5981. doi: 10.1038/s41598-018-24132-5. PMID: 29654238; PMCID: PMC5899125.

Kwang W Oh and Chong H Ahn 2006 J. Micromech. Microeng. 16 R13 DOI 10.1088/0960-1317/16/5/R01.

Alberts B, Bray D, Hopkin K, Johnson A, Lewis J, Raff M, Roberts K, Walter P (2014). Essential Cell Biology (Fourth ed.). New York, NY, USA: Garland Science. pp. 621-626. ISBN 978-0-8153-4454-4.

Amselem G, Guermonprez C, Drogue B, Michelin S, Baroud CN. Universal microfluidic platform for bioassays in anchored droplets. Lab Chip. Oct. 18, 2016;16(21):4200-4211. doi: 10.1039/c6lc00968a. PMID: 27722379.

Antonin W, Neumann H (Jun. 2016). "Chromosome condensation and decondensation during mitosis". Current Opinion in Cell Biology. 40: 15-22. doi:10.1016/j.ceb.2016.01.013. PMID 26895139.

Baroud, C. N., Gallaire, F., & Emi Dangla, R. (2010). Dynamics of microfluidic droplets. Lab on a Chip. website://doi.org/10.1039/c001191f.

Bonev, Boyan; Cavalli, Giacomo (Oct. 14, 2016). "Organization and function of the 3D genome". Nature Reviews Genetics. 17 (11): 661-678. doi:10.1038/nrg.2016.112. ISSN 1471-0056.

Casavant, B. P., Berthier, E., Theberge, A. B., Berthier, J., Montanez-Sauri, S. I., Bischel, L. L., . . . Beebe, D. J. (2013). Suspended microfluidics. Proceedings of the National Academy of Sciences of the United States of America, 110(25), 10111-10116. website://doi.org/10.1073/pnas.1302566110.

Chan, T.-F., Ha, C., Phong, A., Cai, D., Wan, E., Leung, L., . . . Xiao, M. (2006). A simple DNA stretching method for fluorescence imaging of single DNA molecules. Nucleic Acids Research, 34(17). website://doi.org/10.1093/nar/gkl593.

Chou CF, Tegenfeldt JO, Bakajin O, Chan SS, Cox EC, Darnton N, Duke T, Austin RH. Electrodeless dielectrophoresis of single- and double-stranded DNA. Biophys J. Oct. 2002;83(4):2170-9. doi: 10.1016/S0006-3495(02)73977-5. PMID: 12324434; PMCID: PMC1302305.

Chung J, Kim YJ, Yoon E. Highly-efficient single-cell capture in microfluidic array chips using differential hydrodynamic guiding structures. Appl Phys Lett. Mar. 21, 2011;98(12):123701. doi: 10.1063/1.3565236. PMID: 21673831; PMCID: PMC3112185.

Conti, et al. (2003) Current Protocols in Cytometry John Wiley & Sons, Inc.

Dai, L., Renner, C. B., & Doyle, P. S. (2016). The polymer physics of single DNA confined in nanochannels. Advances in Colloid and Interface Science, vol. 232, pp. 80-100. website://doi.org/10.1016/j.cis.2015.12.002.

DeCarvalho AC, Kim H, Poisson LM, Winn ME, Mueller C, Cherba D, et al. (May 2018). "Discordant inheritance of chromosomal and extrachromosomal DNA elements contributes to dynamic disease evolution in glioblastoma". Nature Genetics. 50 (5): 708-717. doi:10.1038/s41588-018-0105-0. PMC 5934307. PMID 29686388.

Deschamps J, Rowald A, Ries J. Efficient homogeneous illumination and optical sectioning for quantitative single-molecule localization microscopy. Opt Express. Nov. 28, 2016;24(24):28080-28090. doi: 10.1364/OE.24.028080. PMID: 27906373.

Dong YZ, Seo Y , Choi HJ . Recent development of electro-responsive smart electrorheological fluids. Soft Matter. Apr. 24, 2019;15(17):3473-3486. doi: 10.1039/c9sm00210c. PMID: 30968927.

Ebner, A., Wildling, L., & Gruber, H. J. (2019). Functionalization of AFM tips and supports for molecular recognition force spectroscopy and recognition imaging. In Methods in Molecular Biology (vol. 1886). website://doi.org/10.1007/978-1-4939-8894-5_7.

Frühauf, J., Kronert, S. Wet etching of silicon gratings with triangular profiles. Microsyst Technol 11, 1287-1291 (2005). https://doi.org/10.1007/s00542-005-0612-7.

Gaanin, J., Synatschke, C. V., & Weil, T. (Jan. 11, 2020). Biomedical Applications of DNA-Based Hydrogels. Advanced Functional Materials, vol. 30, p. 1906253. website://doi.org/10.1002/adfm.201906253.

Gibb, B., Silverstein, T. D., Finkelstein, I. J., & Greene, E. C. (2012). Single-stranded DNA curtains for real-time single-molecule visualization of protein-nucleic acid interactions. Analytical Chemistry, 84(18), 7607-7612. website://doi.org/10.1021/ac302117z.

Grubb J, Brown MS, Bishop DK. Surface Spreading and Immunostaining of Yeast Chromosomes. J Vis Exp. Aug. 9, 2015;(102): e53081. doi: 10.3791/53081. PMID: 26325523; PMCID: PMC4632477.

Gueroui, Z., Place, C., Freyssingeas, E., & Berge, B. (2002). Observation by fluorescence microscopy of transcription on single combed DNA. Proceedings of the National Academy of Sciences of the United States of America, 99(9), 6005-6010. website://doi.org/10.1073/pnas.092561399.

Hammond CM, Strømme CB, Huang H, Patel DJ, Groth A (Mar. 2017). "Histone chaperone networks shaping chromatin function". Nature Reviews. Molecular Cell Biology. 18 (3): 141-158. doi:10.1038/nrm.2016.159. PMC 5319910. PMID 28053344.

Han, J., Fu, J., & Schoch, R. B. (2007). Molecular sieving using nanofilters: Past, present and future. In Lab on a Chip (vol. 8, Issue 1, pp. 23-33). website://doi.org/10.1039/b714128a.

Hilber, W. (2016). Stimulus-active polymer actuators for next-generation microfluidic devices. Applied Physics A: Materials Science and Processing, 122(8). website://doi.org/10.1007/s00339-016-0258-6.

Shehadul Islam M, Aryasomayajula A, Selvaganapathy Pr. A Review on Macroscale and Microscale Cell Lysis Methods. Micromachines (Basel). Mar. 8, 2017;8(3):83. doi: 10.3390/mi8030083. PMCID: PMC6190294.

(56)　　　　　References Cited

OTHER PUBLICATIONS

Juncker, D., Schmid, H., Drechsler, U., Wolf, H., Wolf, M., Michel, B., . . . Delamarche, E. (2002). Autonomous microfluidic capillary system. Analytical Chemistry, 74(24), 6139-6144. website://doi.org/10.1021/ac0261449.

Kelly EA , Willis-Fox N , Houston JE , Blayo C , Divitini G , Cowieson N , Daly R , Evans RC . A single-component photorheological fluid with light-responsive viscosity. Nanoscale. Mar. 21, 2020;12(11):6300-6306. doi: 10.1039/c9nr10350c. Epub Mar. 12, 2020. PMID: 32162625.

Kempfer, R., & Pombo, A. (2020). Methods for mapping 3D chromosome architecture. Nature Reviews Genetics, 21 (4), 207-226. website://doi.org/10.1038/s41576-019-0195-2.

Koch J, Vogt G, Kissel W. Cytoplasmic DNA is structurally different from nuclear DNA. Naturwissenschaften. May 1983;70(5):252-4. doi: 10.1007/BF00405447. PMID: 6877387.

Larson, Ronald G., "The Structure and Rheology of Complex Fluids (Topics in Chemical Engineering)", Oxford University Press, 1998, ISBN 13: 9780195121971.

Lebofsky, R., & Bensimon, A. (2003). Single DNA molecule analysis: Applications of molecular combing. Briefings in Functional Genomics and Proteomics, 1(4), 385-396. website://doi.org/10.1093/bfgp/1.4.385.

Di Carlo D, Wu LY, Lee LP. Dynamic single cell culture array. Lab Chip. Nov. 2006;6(11):1445-9. doi: 10.1039/b605937f. Epub Sep. 4, 2006. PMID: 17066168.

Gac, S. & de Boer, Hans & Wijnperle, Daniel & Meuleman, W. & Carlen, Edwin & Van den Berg, Albert & Kim, Tae & Lee, Yoon-Sik & Chung, Taek-Dong & Jeon, Noo & Lee, Sang-Hoon & Suh, Kahp-Yang. (2009). Parallel single cell analysis on an integrated microfluidic platform for cell trapping, lysis and analysis. IEEE Systems Journal—IEEE Syst J.

Li, H., Liu, J., Li, K., & Liu, Y. (2019). Piezoelectric micro-jet devices: A review. Sensors and Actuators, A: Physical, 297, 111552. website://doi.org/10.1016/j.sna.2019.111552.

Li, C., Hite, Z., Warrick, J. W., Li, J., Geller, S. H., Trantow, V. G., . . . Beebe, D. J. (2020). Under oil open-channel microfluidics empowered by exclusive liquid repellency. Retrieved from website://advances.sciencemag.org/.

Lira RB, Steinkühler J, Knorr RL, Dimova R, Riske KA. Posing for a picture: vesicle immobilization in agarose gel. Sci Rep. May 3, 2016;6:25254. doi: 10.1038/srep25254. PMID: 27140695; PMCID: PMC4853705.

Maher CA, Wilson RK (2012). "Chromothripsis and Human Disease: Piecing Together the Shattering Process". Cell. 148 (1-2): 29-32. doi:10.1016/j.cell.2012.01.006. PMC 3658123. PMID 22265399.

Mahshid S, Ahamed MJ, Berard D, Amin S, Sladek R, Leslie SR, Reisner W. Development of a platform for single cell genomics using convex lens-induced confinement. Lab Chip. Jul. 21, 2015;15(14):3013-20. doi: 10.1039/c5lc00492f. PMID: 26062011.

Moore, C. M., & Best, R. G. (2001). Chromosome preparation banding. Encyclopedia of Life Sciences.

Mugele, F., & Baret, J. C. (2005). Electrowetting: From basics to applications. Journal of Physics Condensed Matter, vol. 17, pp. 705-774. website://doi.org/10.1088/0953-8984/17/28/R01.

Nathanson DA, Gini B, Mottahedeh J, Visnyei K, Koga T, Gomez G, et al. (Jan. 2014). "Targeted therapy resistance mediated by dynamic regulation of extrachromosomal mutant EGFR DNA". Science. 343 (6166): 72-6. Bibcode:2014Sci343.72N. doi:10.1126/science.1241328. PMC 4049335. PMID 24310612.

Nguyen HQ, Chattoraj S, Castillo D, Nguyen SC, Nir G, Lioutas A, Hershberg EA, Martins NMC, Reginato PL, Hannan M, Beliveau BJ, Church GM, Daugharthy ER, Marti-Renom MA, Wu CT. 3D mapping and accelerated super-resolution imaging of the human genome using in situ sequencing. Nat Methods. Aug. 2020;17(8):822-832. doi: 10.1038/s41592-020-0890-0. Epub Jul. 27, 2020. PMID: 32719531; PMCID: PMC7537785.

Nilsson, A. N., Emilsson, G., Nyberg, L. K., Noble, C., Stadler, L. S., Fritzsche, J., . . . Westerlund, F. (2014). Competitive binding-based optical DNA mapping for fast identification of bacteria-multi-ligand transfer matrix theory and experimental applications on Escherichia coli. Nucleic Acids Research, (1). website://doi.org/10.1093/nar/gku556.

Nyberg LK, Persson F, Berg J, Bergström J, Fransson E, Olsson L, Persson M, Stålnacke A, Wigenius J, Tegenfeldt JO, Westerlund F. A single-step competitive binding assay for mapping of single DNA molecules. Biochem Biophys Res Commun. Jan. 6, 2012;417(1):404-8. doi: 10.1016/j.bbrc.2011.11.128. Epub Dec. 7, 2011. PMID: 22166208.

Oshige M, Yamaguchi K, Matsuura S, Kurita H, Mizuno A, Katsura S. A new DNA combing method for biochemical analysis. Anal Biochem. May 1, 2010;400(1):145-7. doi: 10.1016/j.ab.2010.01.021. Epub Jan. 18, 2010. PMID: 20085744.

Park MC, Hur JY, Kwon KW, Park SH, Suh KY. Pumpless, selective docking of yeast cells inside a microfluidic channel induced by receding meniscus. Lab Chip. Aug. 2006;6(8):988-94. doi: 10.1039/b602961b. Epub Jun. 19, 2006. PMID: 16874367.

Paterson, Lynn & Agate, B. & Sibbert, W. & Dholakia, K. & Comrie, M. & Brown, Christian & Riches, Andrew & Bryant, Peter & Ferguson, R. & Stevenson, D. & Lake, Tanya & Gunn-Moore, Frank. (2005). Violet diode-assisted photoporation and transfection of cells. BioPharm International. 18. 30-35.

Payne AC, Chiang ZD, Reginato PL, Mangiameli SM, Murray EM, Yao CC, Markoulaki S, Earl AS, Labade AS, Jaenisch R, Church GM, Boyden ES, Buenrostro JD, Chen F. In situ genome sequencing resolves DNA sequence and structure in intact biological samples. Science. Feb. 26, 2021;371(6532):eaay3446. doi: 10.1126/science.aay3446. Epub Dec. 31, 2020. PMID: 33384301; PMCID: PMC7962746.

Pihan, G. a. (2013). Centrosome dysfunction contributes to chromosome instability, chromoanagenesis, and genome reprograming in cancer. Frontiers in Oncology, (Nov. 3), 277. doi: 10.3389/fonc.2013.00277.

Oh H, Lu AX, Javvaji V, DeVoe DL, Raghavan SR. Light-Directed Self-Assembly of Robust Alginate Gels at Precise Locations in Microfluidic Channels. ACS Appl Mater Interfaces. Jul. 13, 2016;8(27):17529-38. doi: 10.1021/acsami.6b03826. Epub Jun. 27, 2016. PMID: 27347595.

Rand, A. C., Jain, M., Eizenga, J. M., Musselman-Brown, A., Olsen, H. E., Akeson, M., & Paten, B. (2017). Mapping DNA methylation with high-throughput nanopore sequencing. Nature Methods, 14(4), 411-413. website://doi.org/10.1038/nmeth.4189.

Reisner, W. W., Morton, K. J., Riehn, R., Wang, Y. M., Yu, Z., Rosen, M., . . . Austin, R. H. (2005). Statics and dynamics of single DNA molecules confined in nanochannels. Physical Review Letters, 94(19). website://doi.org/10.1103/PhysRevLett.94.196101.

Reisner, W. W., Larsen, N. B., Flyvbjerg, H., Tegenfeldt, J. O., & Kristensen, A. (2009). Directed self-organization of single DNA molecules in a nanoslit via embedded nanopit arrays. Proceedings of the National Academy of Sciences of the United States of America, 106(1), 79-84.

Lim SF, Karpusenko A, Sakon JJ, Hook JA, Lamar TA, Riehn R. DNA methylation profiling in nanochannels. Biomicrofluidics. Sep. 2011;5(3):34106-341068. doi: 10.1063/1.3613671. Epub Jul. 25, 2011. PMID: 21869910; PMCID: PMC3161501.

Rush MG, Misra R (Nov. 1985). "Extrachromosomal DNA in eucaryotes". Plasmid. 14 (3): 177-91. doi:10.1016/0147-619X(85)90001-0. PMID 3912782.

Schleyden, M. J. (1847). Microscopical researches into the accordance in the structure and growth of animals and plants.

Schurra C, Bensimon A. Combing genomic DNA for structural and functional studies. Methods Mol Biol. 2009;464:71-90. doi: 10.1007/978-1-60327-461-6_5. PMID: 18951180.

Sharim, H., Grunwald, A., Gabrieli, T., Michaeli, Y., Margalit, S., Torchinsky, D., . . . Ebenstein, Y. (2019). Long-read single-molecule maps of the functional methylome. Genome Research, 29(4), 646-656. website://doi.org/10.1101/gr.240739.118.

Shen MM. Chromoplexy: a new category of complex rearrangements in the cancer genome. Cancer Cell. May 13, 2013;23(5):567-9. doi: 10.1016/j.ccr.2013.04.025. PMID: 23680143; PMCID: PMC3673705.

(56) References Cited

OTHER PUBLICATIONS

Rachel K Smith, Penelope A Lewis, Paul S Weiss, Patterning self-assembled monolayers, Progress in Surface Science, vol. 75, Issues 1-2, 2004, pp. 1-68, ISSN 079-6816, https://doi.org/10.1016/j.progsurf.2003.12.001.

Sounart, T. L., Michalske, T. A., & Zavadil, K. R. (2005). Frequency-dependent electrostatic actuation in microfluidic MEMS. Journal of Microelectromechanical Systems, 14(1), 125-133. website://doi.org/10.1109/JMEMS.2004.839006.

Sounart, T. L., Panchawagh, H. V, & Mahajan, R. L. (2010). Frequency-dependent stability of parallel-plate electrostatic actuators in conductive fluids. Applied Physics Letters, 96(20), 203505. website://doi.org/10.1063/1.3389491.

Stephens PJ, Greenman CD, Fu B, et al. (2011). "Massive Genomic Rearrangement Acquired in a Single Catastrophic Event during Cancer Development". Cell. 144 (1): 27-40. doi:10.1016/j.cell.2010.11.055. PMC 3065307. PMID 21215367.

Szabo Q, Bantignies F, Cavalli G. Principles of genome folding into topologically associating domains. Sci Adv. Apr. 10, 2019;5(4):eaaw1668. doi: 10.1126/sciadv.aaw1668. PMID: 30989119; PMCID: PMC6457944.

Takahashi, Y., Kumatani, A., Shiku, H., & Matsue, T. (2017). Scanning Probe Microscopy for Nanoscale Electrochemical Imaging. Analytical Chemistry, 89(1), 342-357. website://doi.org/10.1021/acs.analchem.6b04355.

Tan, Y.-C., Fisher, J. S., Lee, A. I., Cristini, V., & Lee, A. P. (2004). Design of microfluidic channel geometries for the control of droplet volume, chemical concentration, and sorting +. Miniaturisation for Chemistry, Biology & Bioengineering. website://doi.org/10.1039/b403280m.

Tanyeri, M., Ranka, M., Sittipolkul, N., & Schroeder, C. M. (2011). A microfluidic-based hydrodynamic trap: Design and implementation. Lab on a Chip, 11(10), 1786-1794. website://doi.org/10.1039/c0lc00709a.

Wang YM, Tegenfeldt JO, Reisner W, Riehn R, Guan XJ, Guo L, Golding I, Cox EC, Sturm J, Austin RH. Single-molecule studies of repressor-DNA interactions show long-range interactions. Proc Natl Acad Sci U S A. Jul. 12, 2005;102(28):9796-801. doi: 10.1073/pnas.0502917102. Epub Jun. 30, 2005. PMID: 15994229; PMCID: PMC1168954.

Tøstesen, E., Jerstad, G. I., & Hovig, E. (2005). Stitchprofiles.uio. no: Analysis of partly melted DNA conformations using stitch profiles. Nucleic Acids Research, 33(SUPPL. 2), 573-576. website://doi.org/10.1093/nar/gki424.

Turner KM, Deshpande V, Beyter D, Koga T, Rusert J, Lee C, et al. (Mar. 2017). "Extrachromosomal oncogene amplification drives tumour evolution and genetic heterogeneity". Nature. 543 (7643): 122-125. Bibcode:2017Natur.543.122T. doi:10.1038/nature21356. PMC 5334176. PMID 28178237.

Verhaak RG, Bafna V, Mischel PS (May 2019). "Extrachromosomal oncogene amplification in tumour pathogenesis and evolution". Nature Reviews. Cancer. 19 (5): 283-288. doi:10.1038/s41568-019-0128-6. PMID 30872802.

Volkmuth, W. D., & Austin, R. H. (1992). DNA electrophoresis in microlithographic arrays. Nature, 358(6387), 600-602. website://doi.org/10.1038/358600a0.

Wang, Y. M., Tegenfeldt, J. O., Reisner, W. W., Riehn, R., Guan, X. J., Guo, L., Golding, I., Cox, E. C., Sturm, J. C., & Austin, R. H. (2005). Single-molecule studies of repressor-DNA interactions show long-range interactions. Proceedings of the National Academy of Sciences of the United States of America, 102(28), 9796-9801. website://doi.org/10.1073/pnas.0502917102.

Wheeler AR, Throndset WR, Whelan RJ, Leach AM, Zare RN, Liao YH, Farrell K, Manger ID, Daridon A. Microfluidic device for single-cell analysis. Anal Chem. Jul. 15, 2003;75(14):3581-6. doi: 10.1021/ac0340758. PMID: 14570213.

"Soft Lithography in Biology and Biochemistry," by George M. Whitesides, Emanuele Ostuni, Shuichi Takayama, Xingyu Jiang and Donald E. Ingber, Annual Review of Biomedical Engineering, 2001, vol. 3, pp. 335-373.

Wilson, John (2002). Molecular biology of the cell : a problems approach. New York: Garland Science. ISBN 978-0-8153-3577-1.

"Soft Lithography," by Younan Xia and George M. Whitesides, Annual Review of Material Science, 1998, vol. 28, pp. 153-184.

Xiao, M., Phong, A., Ha, C., Chan, T. F., Cai, D., Leung, L., . . . Kwok, P. Y. (2007). Rapid DNA mapping by fluorescent single molecule detection. Nucleic Acids Research, 35(3).

Yu, Zhaoning & Chou, Stephen. (2004). Triangular Profile Imprint Molds in Nanograting Fabrication. Nano Letters—Nano Lett. 4. 10.1021/nl0349471.

Zhao, Y.-P., & Wang, Y. (2013). Fundamentals and applications of electrowetting: A critical review. Reviews of Adhesion and Adhesives, 1(1), 114-174. website://doi.org/10.7569/RAA.2013.097304.

Alex R. Hastie et al: "Rapid Genome Mapping in Nanochannel Arrays for Highly Complete and Accurate De Novo Sequence Assembly of the Complex Aegilops tauschii Genome", PLoS ONE, vol. 8, No. 2, Feb. 6, 2013; 10 pages.

Somes K Das et al: "Single molecule linear analysis of DNA in nanochannel labeled with sequence specific fluorescent probes", Nucleic Acids Research, Oxford University Press, GB vol. 38, No. 18 Jan. 1, 2010; 8 pages.

* cited by examiner

[0001]

[0002]

A)

B)

(A)

(B)

(A)

(B)

DEVICES AND METHODS FOR CYTOGENETIC ANALYSIS

CROSS-REFERENCE TO RELATED APPLICATIONS

This document claims the benefit of priority to U.S. Provisional Application Ser. No. 63/032,984, filed Jun. 1, 2020, to U.S. Provisional Application Ser. No. 63/087,131, filed Oct. 2, 2020, and to U.S. Provisional Application Ser. No. 63/143,857, filed Jan. 31, 2021, each of which is hereby incorporated by reference in its entirety; and this application is a US Regional Phase entry of PCT/US2021/034754, filed May 28, 2021, which published as WO 2021/247394 on Dec. 9, 2021, which is hereby incorporated by reference in its entirety.

BACKGROUND

Genomic materials including chromosomes, extrachromosomal DNA, exogenous and transcribed RNAs are different in various species, and heterogenous among the individuals in the same species. These genomic materials can be distinct and heterogenous among the individual cells in tissues of the same individual, such as in the cases of mosaicism, cancer or neuron development. Furthermore, they can change dynamically within the same cell along the natural course of time, or from a pathological development such as an infectious event or mutation, or in divergent environment with external stimulus. Ideally, genomic and proteomic analysis technology should be able to detect and discern these differences and changes at individual cellular and subcellular level with structural, environmental, spatial, and chronological context, in real time. A chromosome is a deoxyribonucleic acid (DNA) molecule that contains all or part of the genetic material of an organism, its "genome". Most eukaryotic chromosomes include packaging proteins which, aided by chaperone proteins, bind to and condense the DNA molecule to prevent it from becoming an unmanageable tangle [Hammond, 2017][Wilson, 2002]. For example, an average freely suspended human cell in solution with diameter of 20-100 um contains about 6.4 billion base pairs of DNA divided among 46 chromosomes (diploid). The length of each base pair is about 0.34 nm. Therefore, if the DNA molecule in a diploid cell were elongated, and laid out end to end, the total length of DNA would be approximately 2 meters, and yet remarkably this genomic material can fit in a cell nucleus of diameter 10 micrometers in an organized manner. This is accomplished by packaging the DNA in cells in highly ordered three-dimensional chromosomes. Furthermore, the genome structure of this packaging plays a significant role in gene transcriptional regulation [Bonev, 2016]. Chromosomes are physically visible in discrete forms under a light microscope when the cell is undergoing the metaphase of cell division (where all chromosomes are aligned in the center of the cell in their condensed form) [Alberts, 2014]. Before this happens, every chromosome is copied once (S phase), and the copy is joined to the original by a centromere, resulting either in an X-shaped structure if the centromere is located in the middle of the chromosome, or a two-arm of uneven length structure if the centromere is located near one of the ends. The original chromosome and the copy are now called sister chromatids. In cells, chromosomes go through progressively condensed stages from prophase, metaphase and reach their highest compaction level in anaphase during chromosome segregation [Antonin, 2016]. In human cells, the typical metaphase chromosome size has an approximate dimension of 1.4 micron in width to 10 microns in length. In these highly condensed forms, chromosomes are easiest to distinguish and study [Schleyden, 1847]. Chromosomal recombination during meiosis and subsequent sexual reproduction plays a significant role in genetic diversity. If these structures are manipulated incorrectly, through processes known as chromosomal instability, can result in changes ranging from simpler rearrangements such as inversion, translocation, to highly complex chromoanagenesis [Pihan, 2013] such as chromoplexy [Shen, 2013] and chromothripsis [Maher, 2012] [Stephens, 2011]. Usually, this will make the cell initiate apoptosis leading to its own death, but sometimes mutations in the cell hamper this process and thus cause progression of cancer or developmental and congenital disorders. Extrachromosomal DNA (abbreviated ecDNA) is any DNA that is found off the chromosomes, either inside or outside the nucleus of a cell. Most DNA in an individual genome is found in chromosomes contained in the nucleus. Multiple forms of extrachromosomal DNA exist and serve important biological functions [Rush, 1985], e.g. they can play a role in disease, such as ecDNA in cancer [Verhaak, 2019]. In prokaryotes, nonviral extrachromosomal DNA are primarily found in plasmids whereas in eukaryotes extrachromosomal DNA are primarily found in organelles such as Mitochondria. Although found in normal eukaryotic cells, extrachromosomal DNA (ecDNA) are distinct entities that have been identified in the nuclei of cancer cells and have been shown to carry many copies of driver oncogenes [Nathanson, 2014][deCarvalho, 2018][Turner, 2017]. EcDNA molecules are considered to be a primary mechanism of gene amplification, resulting in many copies of driver oncogenes and very aggressive cancers. EcDNA in the cytoplasm have been found to be structurally different from nuclear DNA. Cytoplasmic DNA are less methylated than DNA found within the nucleus. It was also confirmed that the sequences of cytoplasmic DNA were different from nuclear DNA in the same organism, showing that cytoplasmic DNAs are not simply fragments of nuclear DNA [Koch, 1983]. In cancer cells, ecDNA have been shown to be primarily isolated to the nucleus. In addition to DNA found outside the nucleus in cells, infection of viral genomes also provides an example of extrachromosomal DNA. Clinical Samples are extremely complex, individualized and heterogeneous, at cellular and molecular levels. Large amounts of chromosomal lesions and rearrangements are well known large structural or numerical aberrations to affect biological functions and are associated with complex diseases such as developmental and mental disorders, rare & undiagnosed diseases, reproductive anomalies, blood and all cancers.

Cytogenetics is the study of chromosomes, which are long strands of DNA and associated proteins that contain most of the genomic information in a cell. Cytogenetics involves testing samples of tissue, blood, amniotic fluid or bone marrow in a laboratory to look for changes in chromosomes, including broken, missing, rearranged, or extra chromosomes, as potential signs of a genetic disease or condition or some types of cancer. Cytogenetics may be used to help diagnose a disease or condition, plan treatment, or find out how well treatment is working. Techniques used include karyotyping, analysis of G-banded chromosomes, other cytogenetic and optical banding techniques, as well as molecular cytogenetics such as fluorescent in situ hybridization (FISH) and comparative genomic hybridization (CGH). For example, the Mitelman Database of Chromosome Aberrations and Gene Fusions in Cancer is just one of the databases, supported by National Cancer Institute (NCI), has catalogued a total number of published unique clinical cases of 69,551 (October 2019), with a total number of unique gene fusions of 22,091 and a total number of genes involved of 12,044, since they started to collect information in 1983 (3844 cases) [Mitelman, 2019]. These documented chromosome aberrations were largely discovered by the gold standards of first-line clinical cytogenetics testing (karyotyping, FISH, Array, and CGH), with guidelines recommended by American College of Medical Genetics (ACMG), American Society for Clinical Pathology (ASCP), National Comprehensive Cancer Network (NCCN), American College of Medical Genetics (ACMG), American College of Obstetricians/Gynecologists (ACOG), and World Health Organization (WHO).

The advancement of next generation sequencing (NGS) technologies has rapidly expanded genome analysis. Using such technologies, a large data base of genomic changes mostly comprised with millions of point mutations and SNPs (Single Nucleotide Polymorphisms) in human or biological populations have been generated, but direct clinical utility of vast majority of these genomic changes remains unproven. There are over 8000 known genetic diseases, yet more than 2/3 remain without a clear understanding of the genetic cause. Despite the progress of NGS technology, the cost and technology limitations (for example limited native read length, library bias, and the bioinformatics complexity, to name a few) have limited NGS's wider adoption into more clinical settings.

NGS provides a gain in genome nucleotide resolution, but at the expense of a loss in spatial and structural resolution of the chromosomes and genome analysis. In addition, with a large portion of the genome comprising "Dark Matter" such as instable repetitive regions that are still not easily accessible, NGS technologies have yet to provide true diploid/multiploidy medical grade genome data that is critical for clinical environment. In addition, complete extrachromosomal DNA (ecDNA) information and complex chromothripsis structures remains elusive, as NGS sample prep and algorithms cannot distinguish them a priori. NGS data for accurately identifying structural variants is largely limited to SNPs and short indels.

The well-established cytogenetics techniques of optically interrogating chromosome spreads represent an elegant "top down" true single-cell, single-molecule level test with full real time view of the entire genomic chromosomal sets. The techniques remain the gold standard of first-line tests used by clinicians in tens of thousands hospital and clinical labs with established protocols and guidelines, yielding results trusted by doctors and clinicians. However, despite the historical success of these techniques, significant technological challenges have limited their potential to achieve lower cost, consistent quality, reduced errors, and improved resolution of genomic changes. These limitations include: labor-intensive procedures requiring subjective manual involvement of highly trained professionals (low scalability with 100~500 tests/person/year) [NPAAC, 2013], low resolution of identifying genomic changes, limited to megabases or larger, long turn-around time from sample to answer (typically 3~28 days), and ambiguous or erroneous raw image datasets that hinder the adaption of machine learning that requires further manual curation. Technologies that overcome these limitations, while maintaining the clinical validity of traditional cytogenetic methods will allow for improved patient and doctor access to actionable genomic information of clinical value, unleash the power of medical AI analysis, and help fulfill the promise of personalized medicine.

As provided herein, devices and methods to integrate clinical single-cell cytogenomic optical imaging techniques with microfluidic devices. Here we present devices, systems and methods to automate, standardize, and accelerate the digital cytopathological sample preparation and data generation. In some device and method embodiments, the sample input cell quantity is substantially reduced over traditional methods, thus allowing for a reduction in time required to multiply the cells via growth. In some device and method embodiments, the chromosomes are presented for interrogation in an ordered and controlled manner, thus reducing ambiguities in the image data, and allowing for greater automation and reduced manual curation. In some device and method embodiments, the chromosomes are presented in a substantially elongated format over tradition chromosome spreads, such that with optically equivalent interrogation tools, improved resolution of identifying genomic features within the chromosomes are feasible. In some device and method embodiments, the genomic material can be manipulated in the microfluidic device such that region of interest can be interrogated from different perspectives, in addition, the genomic material can be manipulated to elongate single strands of long nucleic acid molecules in order to un-obfuscate the underlying genomic content that would normally be intractable to interrogation while in a metaphase chromosome state. In some device and method embodiments, single chromosomes, or portions of single chromosomes representing regions of interest can be isolated. In some device and method embodiments, these isolated regions of interest can then be further processed, including amplified, sequenced, or genotyped, on the device, or off the device.

SUMMARY OF THE INVENTION

The invention relates to microfluidic devices for the interrogation of macromolecules, more particularly for preparation of isolated single macromolecules for subsequent processing, including interrogation. In a further aspect, a method is provided for preparing isolated single macromolecules for subsequent processing. The invention is particularly suited for preparing, processing, and interrogating long nucleic acid molecules.

According to a further aspect, the present invention relates to systems, apparatus, kits, algorithms and methods for handling, preparing, analyzing and characterizing (in any order) biological samples. The invention also describes uses of the invention, particularly in relation to nucleic acid physical mapping techniques.

The present disclosure provides devices and methods that facilitate the characterization of genomic variation in large nucleic acid molecules. The devices and methods disclosed herein can enable improved quality of physical maps, for example karyotyping or FISH spreads. In another example, the devices and methods herein can enable manipulation of large nucleic acid molecules in a microfluidic environment to improve the quality and reliability of the genomic data obtained from the interrogation of said molecules. In another example, the specific package from which the nucleic acid macromolecule will be selected from in order to perform interrogation is selected from a collection of packages. In another example, the nucleic acid macromolecule is manipulated in a microfluidic device such that the macromolecule's physical conformation can be altered to obtain interrogation data of the desired region and resolution in the macromolecule.

In some embodiments, the package is a single cell, or single nucleus, contained within are long nucleic acid molecules. In the preferred embodiment, the macromolecules are condensed such as metaphase chromosomes. In yet another embodiment, the cells or nucleus are in a hypotonic state.

In some embodiments, the package is a droplet containing long nucleic acid molecules. The droplet can be an oil-in-water, water-in-oil, water-in-oil-in-water droplet. In some embodiments, the macromolecules are entire chromosomes that originate from a single cell. In some embodiments the macromolecules have already undergone some degree of processing, for example digestion of proteins, binding of labeling bodies, binding of PCR primers, binding of MDA primers, binding of barcodes, digestion of nucleic acid with frequent or rare cutters to achieve the desired size distribution, or combination-there-of. In some embodiments, there may be at least one nucleic acid barcode incorporated into the droplet, which may be separately suspended in solution inside the droplet with the long nucleic acid molecules, or bound to the molecules. In some embodiments, the barcode contains information unique to the droplet, or originating cell, or some other content.

In one set of embodiments, we disclose devices and methods for a passive fluidic device consumable that enables the positioning of a long nucleic acid molecule in a manner such that the nucleic acid can be prepared for interrogation, and imaged using traditional cytogenetic procedures, yet the macromolecule is physically positioned on the device in a controlled manner to improve analysis of the interrogation data via reducing ambiguities. In one set of embodiments, this is accomplished via the deposition of the nucleic acid into a fluidic region of the device defined by patterned features. In another set of embodiments, this is accomplished via the capillary flow of the nucleic acid into a fluidic region of the device defined by patterned features. In all cases, the nucleic acid can be in a variety of states depending on the sample preparation method used, and desired cytogenetic data type. Different embodiments of this invention are designed to accommodate these differing user needs. For example, in one set of embodiments, the input material are cells containing metaphase chromosomes that are to be 'spread' on the device in a non-overlapping manner via the patterned features present on the device. In another set of embodiments, the input material is long nucleic acid molecules that are to be presented in a mostly linear, elongated state within the patterned features present on the device. For all embodiments within this set, the preparation of the nucleic acid with labelling bodies can be done prior to introducing the sample to the device, after the sample has entered the patterned features, or a combination there-of.

In another set of embodiments, we disclose devices and methods for an active microfluidic device in which the positioning and state of the long nucleic acid molecule within said device is controlled by a control instrument. In this set of embodiments, patterned features within the fluidic chip combined with the application of external forces on said molecule controlled by the control instrument, is used to manipulate said molecule such that it can be interrogated or captured for analysis.

For all embodiment devices described, the interrogation of the nucleic acid molecules includes optical interrogation techniques, including but not limited to: fluorescent, TIRF, epifluorescence, brightfield, darkfield, phase contrast.

For all embodiment devices described, the nucleic acid molecules may be recovered for further processing after interrogation, including amplification, sequencing, or genotyping.

For all embodiment devices described, the interrogation of the nucleic acid molecules may be performed while the long nucleic acid molecule is at least partially contained within a gel, or semi-gel like material. The gelling material may be introduced as part of the input solution that contains the input sample, or may be introduced at a later time-point, or may be present before the introduction of the molecule. In one preferable embodiment, the gelling material is added to the device after the packages have been lysed.

The present Invention describe devices and methods that facilitate the improved quantitative characterization of native state chromatin, chromosomes, extrachromosomal DNA, or large genomic variations features (>50 bp, >1000 bp, >10 kb, >100 kb, >1 Mb, >5 Mb or >10 nm, >100 nm, >200 nm, >300 nm, >500 nm, >1?m, >10?m, >100?m, >1000?m) in large nucleic acid DNA molecules, large native state chromatin and chromosomes, extrachromosomal DNA, that are isolated, manipulated, organized for interrogation with traceability to individual nucleus or cell, on or within specifically designed and fabricated micro/nanofluidic surface or environment.

The devices and methods disclosed herein can enable improved quality of physical maps, for example karyotyping or FISH spreads. In some device and method embodiments, the sample input cell quantity is substantially reduced over traditional methods, thus allowing for a reduction in time required to multiply the cells via growth: or allowing direct interrogation of primary cells without culture, or samples of the nature of scarcity, such as CFC (circulating fetal cells), CTC (circulating tumor cells), forensic samples, environmental samples, archaeological samples (frozen tundra), extraterrestrial samples.

In some device and method embodiments, the chromosomes are presented, with improved alignment, for interrogation in an ordered and controlled manner, without physical obstruction/overlapping, with a substantially elongated format over tradition chromosome spreads, improved resolution of identifying genomic features within the chromosomes, thus reducing ambiguities in the image data, and allowing for greater automation, improved machine learning and artificial intelligent analysis, and reduced manual curation. These will enable more accurate data analysis, faster turnaround time and more precise and more conclusive diagnosis and prognosis report generation, ultimately leading to less patient suffering, in time and duration of sample acquisition, waiting time (less so-called Diagnostic Odyssey that could last up to decades or life time), more efficient clinic practice, less clinician and staff exhaustion, and overall tremendous saving in medical cost and burden to society)

In some device and method embodiments, the genomic material such as the nucleus and the chromosomes are presented in native state with the so-called top down approach, without brutal uncontrolled bulk solution style chemical or enzymatic treatment, can be manipulated in the microfluidic device such that regions of interest can be pinpointed and interrogated from multiple different perspectives, dynamically or even chronologically, to un-obfuscate the underlying genomic content that would normally be intractable to interrogation, with a typical conventional fixed static metaphase chromosome karyotyping, or with a brutal force fragmented bulk solution sample preparation methods in conventional sequencing or optical genome mapping methods. For example, this would, for the first time, allow direct in situ interrogation of dynamic genomic and epig-enomic transformation (degradation/reconstruction) of chro-mosomes, to corroborate structural (such as chromatin domain, kinks/nodules, folds), epigenomic (TADs, regula-tory binding complexes, methylation patterns), and genomic (sequencing/mapping, Cis/trans-regulatory functional ele-ments, intro/exon boundaries, initiation, termination sites), in their native context, on the very same analytes from the same cell, same sample, or same individual/patient.

Clinical Samples are extremely complex, individualized and heterogeneous, at cellular and molecular levels. Large amounts of chromosomal lesions and rearrangements are well known large structural or numerical aberrations to affect biological functions and are associated with complex diseases such as developmental and mental disorders, rare & undiagnosed diseases, reproductive anomalies, blood and all cancers.

genomic and proteomic analysis technology should be able to detect and discern these differences and changes at individual cellular and subcellular level with structural, environmental, spatial, and chronological context, in real time. If these structural genomic lesions generated by such as exposure of ionizing radiations, or infectious agents such as retrovirus (8% of human genome are of viral nature via integration process such as retrotransposition) causing chro-mosomal rearrangements and worse, genomic instability, can result in changes ranging from simpler rearrangements such as inversion, translocation, to highly complex chro-moanagenesis, in somatic de novo fashion or permanently in germline. These would lead to cancer or genetic diseases, or failed gene therapy/editing or ineffective genetic engineer-ing/molecular breeding, if not monitored correctly.

In one application embodiments, the capability to pre-cisely identify in the genome through physically mapping, the location, type of de novo or inherited large changes intractable by sequencing alone, especially to pinpoint these variant loci influencing or altering the biological or patho-logical consequences, in the context of other existing func-tional, regulatory, or structural genomic content, is of para-mount diagnostic, prognostic or identifying actionable drug target for developing therapeutics. For example, with a translation like bcr/abl, to disrupt the sequence order and in frame coding to create a new fusion kinase oncogene to drive tumorigenesis, or an example of genomic repeat expansion or contraction (Fragile X or FSHD) related genetic disease, a top down visualization technology tool able to visualize the event is very useful to allow the further isolation and dissemination of the variant location, exact fusion point for diagnosis.

In some application embodiments, the capability to pre-cisely identify in the genome through physically mapping, the location, type of de novo or inherited large changes intractable by sequencing alone, especially to pinpoint these variant loci influencing or altering the biological or patho-logical consequences, in the context of other existing func-tional, regulatory, or structural genomic content, is of para-mount diagnostic, prognostic or identifying actionable drug target for developing therapeutics. For example, a retrovirus such as HIV, or a herpes virus such as EBV, could integrated into host genome in specific or random location or orienta-tion, to disrupt the sequence order, coding framing, distances of functional, a top down visualization technology tool able to visualize host genome sequence-foreign sequence ele-ments-host genome (new human-virus-human structure) is very useful to allow the further isolation and dissemination of the insertion location, orientation, exact boundary sequence/fusion point, to decide for example if it is an in frame coding or out of frame coding sequence, to cause early protein truncation, or a new fusion protein, or if a strong viral promoter were inserted to drive an oncogene previ-ously were expressed at lower level.

In another application embodiments, the capability to precisely identify in the genome through physically map-ping, the location, type of de novo or genetic targeted large changes intractable by sequencing alone, and especially to pinpoint the intended locus target for gene editing or gene therapy in methods such as viral vector delivery (AAV type) or CRISPR-type, if an off target integration or modification sites due to errant or non-optimal recombination sites or guide RNA sequence probe design, it might have unintended detrimental short or long term genetic consequences to the patient. It would be of great medical value to quality control and proof test the vector or probe design by assessing the off target rate, and locations in the context of whole genome and its consequential biological or pathological outcome. For example, a mock CRISPR experiment could be set up with intended RNA guide probe sequence, and an engineered deficient fluorescently labeled CAS complex that knocking out enzymatic editing function except binding and stabiliz-ing function, to be visualized, with the disclosed invention technology, the effectiveness and precision of the physical off target landing sites within host genome. A gene editing "drill" so to speak, before real and permanent damage is done.

In another application embodiments, the capability to precisely identify in the genome through physically map-ping, the location, type of de novo or genetic engineered large changes intractable by sequencing alone, and espe-cially to pinpoint the intended locus target for gene editing in methods such as genetic engineering. It would be of great utility value to be able to visualize and monitor the engi-neered modification such as transfection or knock-in/knock-out processes, in the context of whole genome and its consequential biological trait improvement in molecular breeding. For example, a desired trait locus could be enhanced by introducing a much more robust promotor/enhancer, in the right location and orientation to the target gene, to increase its expression level or but knocking out a suppressive regulatory mechanism in the genome.

INCORPORATION BY REFERENCE

All publications, patents, and patent applications men-tioned in this specification are herein incorporated by ref-erence to the same extent as if each individual publication, patent, or patent application was specifically and individu-ally indicated to be incorporated by reference.

BRIEF DESCRIPTION OF DRAWINGS

For all drawings, the use of roman numerals: i), ii), iii), iv) are to denote a passage of time.

DETAILED DESCRIPTION

Figure 1:
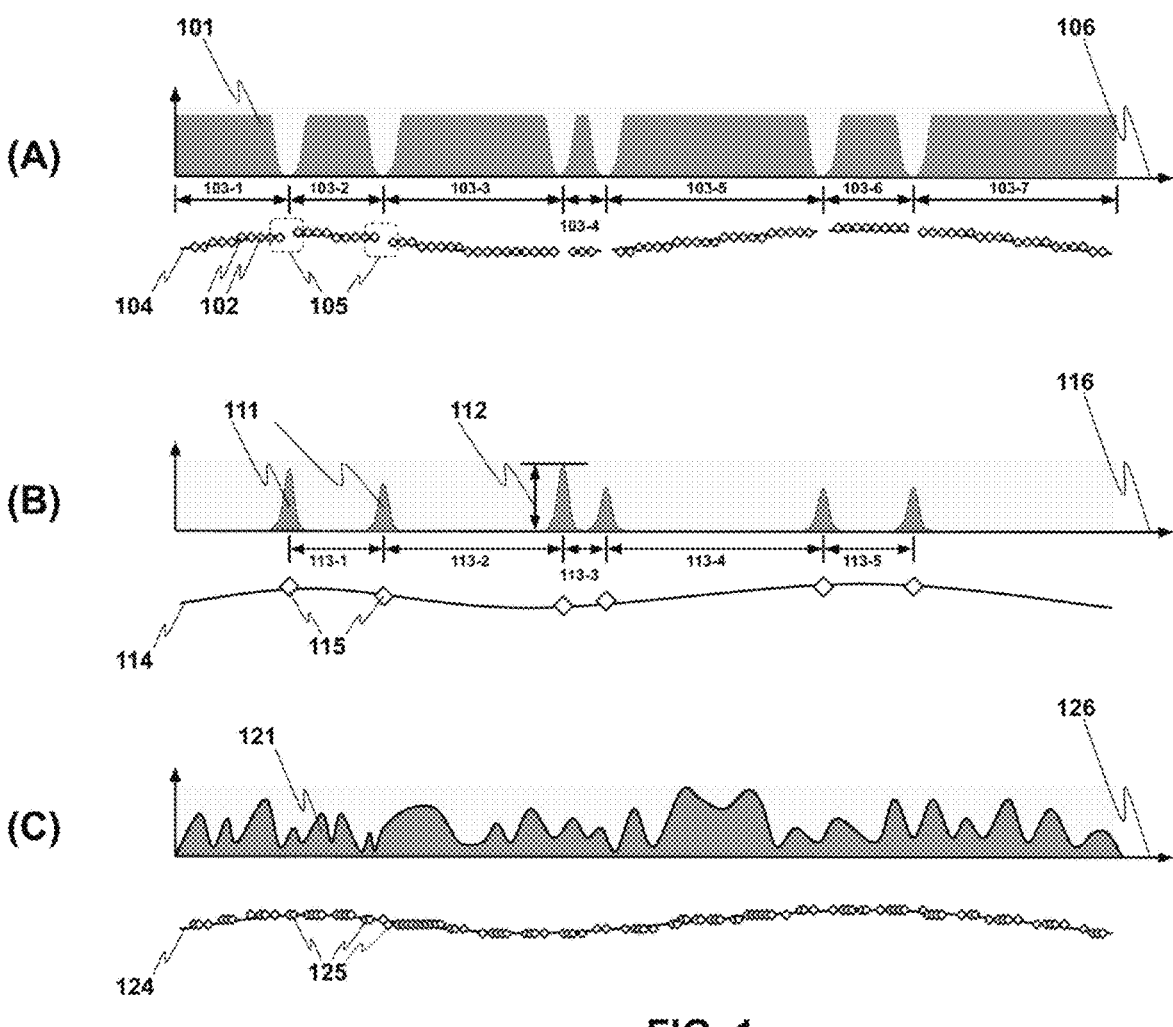
FIG. 1 demonstrates 3 different non-limiting embodi-ments of generating a physical map along the length of a long nucleic acid molecule. (A) is a physical map generated by cleaving the molecule at known recognition sites pro-ducing an ordered pattern of lengths. (B) is a physical map generated by attaching label bodies at known recognition sites producing an ordered pattern of segments. (C) is a physical map generated by attaching label bodies along the length of molecule in a manner such the density of the labeling bodies correlates with the underlying AT/CG ratio or other epigenomic patterns.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

The terms used in this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. It will be appreciated that way. Consequently, alternative language and synonyms may the same thing can typically be described in more than one be used for any one or more of the terms discussed here. Synonyms for certain terms are provided. However, a recital of one or more synonyms does not exclude the use of other synonyms, nor is any special significance to be placed upon whether or not a term is elaborated or discussed herein. All publications, patent applications, patents, and other references mentioned herein are incorporated by reference. In the case of conflict, the present specification, including definitions, will control. In addition, the materials, methods, and examples are illustrative only and are not intended to be limiting.

The invention is also described by means of particular examples. However, the use of such examples anywhere in the specification, including examples of any terms discussed herein, is illustrative only and in no way limits the scope and meaning of the invention or of any exemplified term. Likewise, the invention is not limited to any particular embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

As used herein, "about" or "approximately" in the context of a number shall refer to a range spanning+/−10% of the number, or in the context of a range shall refer to an extended range spanning from 10% below the lower limit of the listed range to 10% above the listed upper limit of the range.

The use of the term "or" in the claims is used to mean "and/or" unless explicitly indicated to refer to alternatives only or the alternatives are mutually exclusive, although the disclosure supports a definition that refers to only alternatives and "and/or."

The words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

The use of the term "combination" is used to mean a selection of items from a collection, such that the order of selection does not matter, and the selection of a null set (none), is also a valid selection when explicitly stated. For example, the unique combinations including the null of the set {A,B} that can be selected are: null, A, B, A and B.

The phrase "at least one selected from the list of A, B, and C" refers to sets comprising only, A and B, or A, B, and C, alone or in combination with other moieties. The phrase does not require that A, B, and C necessarily be present.

Sample. The term "sample," as used herein, generally refers to a biological sample of a subject which at least partially contains nucleic acid originating from said subject. The biological sample may comprise any number of macromolecules, for example, cellular long nucleic acid molecules. The sample may be a cell sample. The sample may be a cell line or cell culture sample. The sample may be a CTC (circulating tumor cells) or CFC (circulating fetal cells) sample. The sample can include one or more cells. The sample can include one or more microbes. The biological sample may be a nucleic acid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

Nucleic Acid. The terms "nucleic acid", "nucleic acid molecule", "oligonucleotide" and "polynucleotide", "nucleic acid polymer", "nucleic acid fragment", "polymer" are used interchangeably and refer to a polymeric form of nucleotides of any length, either deoxyribonucleotides or ribonucleotides, or analogs thereof. The terms encompass, e.g., DNA, RNA and modified forms thereof. Polynucleotides may have any three-dimensional structure, and may perform any function, known or unknown. Non-limiting examples of polynucleotides include a gene, a gene fragment, exons, introns, messenger RNAs (mRNA), transfer RNAs, ribosomal RNAs, lncRNAs (Long noncoding RNAs), lincRNAs (long intergenic noncoding RNAs), ribozymes, cDNA, ecDNAs (extrachromosomal DNAs), artificial minichromosomes, cfDNAs (circulating free DNAs), ctDNAs (circulating tumor DNAs), cffDNAs (cell free fetal DNAs), recombinant polynucleotides, branched polynucleotides, plasmids, vectors, isolated DNA of any sequence, control regions, isolated RNA of any sequence, nucleic acid probes, and primers. Unless specifically stated otherwise, the nucleic acid molecule can be single stranded, double stranded, or a mixture there-of. For example, there may be hairpin turns or loops.

Long nucleic acid molecule. Unless specifically stated otherwise, a "long nucleic acid fragment" or "long nucleic acid molecule" is double strand nucleic acid of at least 5 kbp in length, and is thus a kind of macromolecule, and can span to an entire chromosome. It can originate from any source, man-made or natural, including single cell, a population of cells, droplets, an amplification process, etc. It can include nucleic acids that have additional structure such as structural proteins histones, and thus includes chromatin. It can include nucleic acid that has additional bodies bound to it, for example labeling bodies, DNA binding proteins, RNA.

Labelling body. A "labelling body" used herein is a physical body that can bind to a nucleic acid molecule, which can be used to generate a signal that can be detected with interrogation, that differs from a detected signal (or lack there-of) that would be generated by said nucleic acid without said body. A labelling body may be a fluorescent intercalating dye that when bound to nucleic acid, can be used in a fluorescent imaging system to identify the presence of said nucleic acid. In another example, a labelling body may by a compound that binds specifically to methylated nucleotides, and gives a current blockade signal when transported through a nanopore, thus reporting a signal as to said molecule's methylation state. In another example, a fluorescent probe specifically hybridized to a sequence of a nucleic acid, thus providing confirmation with a fluorescent imaging system that the sequence is present on said nucleic acid. In some cases, the absence of the labelling body, is itself the signal. In some cases, the signal associated with the labeling body is an attenuation, blocking, displacement, quenching, or modification of a signal from another labeling body. Non-limiting examples include: binding of a dark labeling body to the nucleic acid to displace an existing bond fluorescent body: binding of a dark labeling body to the nucleic acid to block a fluorescent labeling body from binding: quenching a near-by fluorescent labeling body bond to a nucleic acid: directly, or indirectly, reacting with a fluorescent labeling body bond to a nucleic acid to reduce its fluorescence. In some cases, the labelling body is not physically attached to the nucleic molecule at the time of interrogating said nucleic molecule and labelling body. For example, a labelling body may be attached to a nucleic acid molecule via a cleavable linker. At the desired time, the linker is cleaved, releasing said labelling molecule which is then detected by interrogation.

Interrogation. "Interrogation" is a process of assessing the state of a labeling body on a nucleic acid by measuring a signal generated directly, or indirectly from the labeling body. It may be a binary assessment, such as the labeling body is present, or not. It may be quantitative such as how many labeling bodies are present on a molecule. It may be a trace of the density and/or physical count of labeling bodies along the length the molecule in relation to the molecule's physical structure. The signal may be fluorescent, electrical, magnetic, physical, chemical. The signal may be analog or digital in nature. For example, the signal may be an analog density profile of the labeling body along the length of the nucleic acid. Non exhaustive examples of different interrogation methods include fluorescent imaging, bright-field imaging, dark-field imaging, phase contrast imaging, super resolution imaging, current, voltage, power, capacitive, inductive, or reactive measurement, nanopore sensing (both column blockade through the pore, and tunneling across the pore), chemical sensing (eg: via a reaction), physical sensing (eg: interaction with a sensing probe), SEM, TEM, STM, SPM, AFM. In addition, combinations of different labeling bodies and interrogation methods are also possible. For example: fluorescent imaging of an intercalating dye on a nucleic acid, while translocating said nucleic acid through a nanopore and measuring the pore current.

Interrogation region. The "interrogation region" is the region in the device in which interrogation occurs.

Sequence. The term "sequence" or "nucleic acid sequence" or "oligonucleotide sequence" refers to a contiguous string of nucleotide bases and in particular contexts also refers to the particular placement of nucleotide bases in relation to each other as they appear in an oligonucleotide.

Sequencing can be performed by various systems currently available, such as, with limitation, a sequencing system by Illumina, Pacific Biosciences, Oxford Nanopore, Life Technologies (Ion Torrent), BGI.

Phasing. "Phasing" is the task or process of assigning genetic content to either the paternal or material chromosomes. The genetic content can be a nucleic acid molecule, a sequence, or a consensus from a set of sequences. The genetic content can be a single nucleic acid molecule whose sequence content may be known, unknown, or partially known. For example, it may be determined that a nucleic acid molecule originates from the mother, however the sequence content of said molecule is completely, or partially, unknown.

In some embodiments, within the context of this disclosure, phasing also refers to the identification that two separate genetic contents originate from the same maternal or paternal chromosome, however it may not be known to which; or that the two separate genetic contents originate from a different chromosome (one to the maternal, the other to the paternal), however again it may not be known to which. The said genomic content, in the concept of "genomic phasing", could be further expanded from separating the primary linear nucleic acid sequence information in the context of paternal, maternal, chromosomal, sister chromatids and extra-chromosomal entities, to include its native epigenomic information associated with the sequence, and to include the next level of secondary/tertiary/quaternary structures associated with the underlying sequence information, on maternal, paternal, chromosomal, sister-chromatids, large genomic regions and include but not limited to extra-chromosomal genomic entities, that were naturally occurring such as ecDNA or man-made artificial mini-chromosomes.

Structural Variation. As used herein, "structural variation" or "SV" is the variation in structure of an organism's chromosome with respect to a genomic reference. These variations include a wide variety of different variant events, including insertions, deletions, duplications, retrotransposition, translocations, inversions short and long tandem repeats, rearrangements and the like. These structural variations are of significant scientific interest, as they are believed to be associated with a range of diverse genetic diseases. In general, the operational range of structural variants includes events >50 bp, while the "large structural variations" typically denotes events >1,000 bp or more. The definition of structural variation does not imply anything about frequency or phenotypical effects.

Genomic Reference. A "genomic reference" or "reference" is any genomic data set that can be compared to another genomic data set. Any data formats may be employed, including but not limited to sequence data, karyotyping data, methylation data, genomic functional element data such as cis-regulatory element (CRE) map, primary level structural variant map data, higher order nucleic acid structure data, physical mapping data, genetic mapping data, optical mapping data, raw data, processed data, simulated data, signal profiles including those generated electronically or fluorescently. A genomic reference may include multiple data formats. A genomic reference may represent a consensus from multiple data sets, which may or may not originate from different data formats. The genomic reference may comprise a totality of genomic information of an organism or model, or a subset, or a representation. The genomic reference may be an incomplete representation of the genomic information it is representing.

The genomic reference may be derived from a genome that is indicative of an absence of a disease or disorder state or that is indicative of a disease or disorder state. Moreover, the genomic reference (e.g., having lengths of longer than 100 bp, longer than 1 kb, longer than 100 kb, longer than 10 Mb, longer than 1000 Mb) may be characterized in one or more respects, with non-limiting examples that include determining the presence (or absence) of a particular feature, a particular haplotype, one or more genetic variations, single nucleotide polymorphisms (SNPs), and combinations thereof, referring not only to being present or absent from the genomic reference in its entirety, but also from a particular region of genomic reference, as defined by the neighboring genomic content. Moreover, any suitable type and number of sequence characteristics of the genomic reference can be used to characterize the sequence of the sample nucleic acid, as derived (or not derived) from a nucleic acid indicative of the disorder or disease based upon whether or not it displays a similar character to the reference nucleic acid sequence.

In some cases, the genomic reference is a physical map. This can be generated in any number of ways, including but not limited to: raw single molecule data, processed single molecule data, an in-silico representation of a physical map generated from a sequence or simulation, an in-silico representation of a physical map generated by assembling and/or averaging multiple single molecule physical maps, or combination there-of. For example, based on a known, or partially known sequence, a simulated in-silico physical map can be generated based on the method of generating a physical map used. In an embodiment where-by the physical map comprises labelling bodies at known sequences, a discrete ordered set of segment lengths in base-pairs can be generated. In an embodiment where-by the physical map comprises a continuous analog signal of labeling signal density along the sequence length, in base-pairs based on simulated local hydrogen bonds dissociation kinetics between the double helices, in chemical moiety modification, regulatory factor association or structural folding patterns based on nucleotide sequence and predicted functional element database maps.

In some cases, the genomic reference is data obtained from microarrays (for example: DNA microarrays, MMChips, Protein microarrays, Peptide microarrays, Tissue microarrays, etc), or karyotypes, or FISH analysis. In some cases, the genomic reference is data obtained from 3D Mapping technologies.

In some cases, characterizations of the comparison with the genomic reference may be completed with the aid of a programmed computer processor. In some cases, such a programmed computer processor can be included in a computer control system.

Physical Mapping. "Physical mapping" or "mapping" of nucleic acid comprises a variety of methods of extracting genomic, epigenomic, functional, or structural information from a physical fragment of long nucleic acid molecule, in which the information extracted can be associated with a physical coordinate on the molecule. As a general rule, the information obtained is of a lower resolution than the actual underlying sequence information, but the two types of information are correlated (or anti-correlated) spatially within the molecule, and as such, the former often provides a 'map' for sequence content with respect to physical location along the nucleic acid. In some embodiments, the relationship between the map and the underlying sequence is direct, for example the map represents a density of AG content along the length of the molecule, or a frequency of a specific recognition sequence. In some embodiments, the relationship between the map the underlying sequence is indirect, for example the map represents the density of nucleic acid packed into structures with proteins, which in turn is at least partially a function of the underlying sequence. In some embodiments, the physical map is a linear physical map, in which the information extracted can be assigned along the length of an axis, for example, the AT/CG ratio along the major axis of long nucleic acid molecule. In the preferred embodiment, the linear (or 1D) physical map is generated by interrogating labeling bodies that are bound along an elongated portion of a long nucleic acid molecule's major axis. For clarity, a string occupying 3D space in a coiled state can be represented as straight line, and thus extracted values along the 3D coil, can be represented as binned values along a 1D representation of the string, and thus constitute a linear physical map. In some embodiments, the physical map is a 2D physical map, in which the information extracted can be assigned within a plane that comprises the molecule, for example: karyotyping. In some embodiments, the physical map is a 3D physical map, in which the information extracted can be assigned in 3D volume in which the molecule occupies. For example, tagging with super-resolution techniques to identify in (x,y, z) space the location of the tag within the chromosome as demonstrated with OligoFISSEQ [Nguyen, 2020], or in-situ genome sequencing [Payne, 2020].

The first and most widely used form of physical mapping is karyotyping, where-by metaphase chromosomes are treated with a stain process that preferentially binds to AT or CG regions, thus producing 'bands' that correlate with the underlying sequence as well as the structural and epigenomic patterns of the nucleic acid [Moore, 2001]. However, the resolution of such a process, in the sense of nucleotide sequences, is quite poor, about 5-10 Mbp, due to the condensed nature of nucleic acid being imaged. More recent methods using linear mapping of elongated interphase genomic DNA, have been generated by imaging nucleic acid digested at known restriction sites [Schwartz, 1988, U.S. Pat. No. 6,147,198] (eg: see FIG. 1(A)), imaging attached fluorescent probes at nicking sites [Xiao, 2007] (eg: see Figure, 01(B)), imaging the fluorescent signature of a nucleic acid molecule's methylation pattern [Sharim, 2019], imaging the fluorescent signature of a chromatin's histone [Riehn, 2011], electrical detection of bound probes to a nucleic acid through a sensor [Rose, 2013, 2014/0272954], and electrical detection of the methylation signature on a nucleic acid using a nanopore sensor [Rand, 2017]. Another method of linear physical mapping is to measure the AT/CG relative density or local melting temperature along the length of an elongated nucleic molecule (eg: see FIG. 1(C)). Such a signal can either be used to compare against other similar maps, or against a map generated in-silico from sequence data. There are many ways of generating such a signal. For example, the signal can be fluorescent or electrical in nature. Nucleic acid can be uniformly stained with an intercalating dye, and then partially melted resulting in the relative loss of dye in regions of rich AT content [Tegenfeldt, 2009, U.S. Pat. No. 10,434,512]. Another method is to expose double stranded nucleic acid to two different species that compete to bind to the nucleic acid. One species is non-fluorescent and preferentially binds to AT rich regions, while the other species is fluorescent and has no such bias [Nilsson, 2014]. Yet another method is to use two different color dyes that differentially label the AT and CG regions.

Mapping using such non-condensed interphase nucleic acid polymer strands has improved upon the resolution of the primary sequence information, however the maps were stripped of any native structural folding or bound supporting proteins information and are often extracted from bulk solution of pooled samples with many potentially heterogeneous cells. Recently, 3D physical maps have been demonstrated where-by fluorescent tags attached to chromosomes as specific locations are interrogated to determine their relative position within the chromosome in 3D space.

FIG. 1 demonstrates a variety of different embodiments for generating and interrogating a long nucleic acid molecule linear physical map. In FIG. 1(A), a physical map of a long nucleic acid molecule 104 is generated by cleaving the molecule at particular sequence sites (eg: recognition sites for restriction enzymes) thus resulting in gaps 105 where the cleaving event took place. Along the length of a molecule, a dye is attached non-specifically (eg: using an intercalating dye) such that child molecules from the originating the parent molecule can be interrogated to generate a signal 101 that follows the physical length (0106) of the parent molecule. The signal can then be used determined the lengths and order of the individual child molecules {103-x}, and thus generating the parent molecule's physical map. In most embodiments of this method, the parent molecule is combed onto a surface and then cleaved, so as to maintain physical proximity and relative order of the child molecules. However, such an embodiment could also be implemented in at least a partially elongated state within an elongating channel of a confined fluidic device such that the order of the child molecules can be interrogated [Ramsey, 2015, U.S. Pat. No. 10,106,848]. In some embodiments, a mixture of different cleaving sites may be used simultaneously.

In FIG. 1(B), a physical map of a long nucleic acid molecule 114 is generated by sparsely binding label bodies 115 along the length of the molecule, with the binding sites correlated (or anti-correlated) with a set of specific target(s). In some methods, the labeling body is bound directly to a sequence motif target. In some methods, the labeling body generating a signal is incorporated via a sequence specific nick site. The long nucleic acid molecule with labeling bodies is interrogated, generating signals 111 from the label bodies 115 along the physical length of the molecule 116. The distance between the signals, a collection of lengths and orders {113-x} then represents the molecule's physical map. In some embodiments, further information can be generated by also interpreting the relative magnitudes of the signals 112 from the various labeling sites. When fluorescent interrogation is used, different color labeling bodies can be used to represent different specific sites.

In FIG. 1(C), a physical map of a long nucleic acid molecule 124 is generated by densely binding labeling bodies 125 along the length of the molecule, such that the binding pattern correlates (or anti-correlates) with the underlying physical sequence content of the molecule. For example, the relative AT/CG content, or the relative melting temperature, or the relative density of methylated CGs. Due to the dense nature of the labeling bodies in this method, the physical map is not a collection of lengths and orders, but rather an analog signal 121 that varies in intensity along the physical length of the molecule 126.

The method of interrogation to generate a physical map is typically fluorescent imaging, however different embodiments are also possible, including a scanning probe along the length of a combed molecule on a surface, or a constriction device that measures the coulomb blockade current through or tunneling current across the constriction as the molecule translocate through.

Unless specifically stated otherwise, a physical map refers to any of the previously mentioned methods, including combinations there-of. For example, a long nucleic acid molecule may have a physical map generated from the AT/TC density with a fluorescent labelling body along the length of the molecule, and then also have a physical map generated from the methylation profile along the length of the molecule by constriction device as the molecule is transported through said constriction device.

Elongated Nucleic Acid. The majority of linear physical mapping methods that use fluorescent imaging or electronic signals to extract a signal related to the underlying genomic, structural, or epigenomic content employ some form of method to at least locally 'elongate' the long nucleic acid molecule such that the resolution of the physical mapping in the region of elongation can be improved, and disambiguates reduced. A long nucleic acid molecule in its natural state in a solution will form a random coil. Thus, a variety of methods have been developed to 'uncoil' and elongate the molecule.

By binding a portion of long nucleic acid molecules on a functionalized solid surface, the molecule is elongated by flowing a solution and ultimately pulled taut, coming into full contact with the substrate surface [Bensimon, 1997, U.S. Pat. No. 7,368,234], a technique typically called 'combing' DNA. Alternatively, there are other long polymer elongation methods such as fluid flow induced elongation with ends anchoring on surface [Gibb, 2012], aqueous solution hydrodynamic focusing by laminar flows [Chan, 1999, U.S. Pat. No. 6,696,022], or linearization by confining nanochannels [Tegenfeldt, 2005], long nucleic acid molecules in microfluidic device pulled by two angled opposing electric fields forces in a presence of physical obstacle features [Volkmuth, 1992], molecules hydrodynamically trapped in a fluidic device by simultaneously exposed to two opposing externally applied forces [Tanyeri, 2011]. Most of the time, the elongation state of at least a portion of the long nucleic acid molecule has to be sustained by an external force before otherwise returning to its natural random coiled state, unless at least a portion of the nucleic acid is retained in the elongated state by physical confinement without a sustaining external force [Dai, 2016].

Unless specifically stated otherwise, an 'elongated' or 'partially elongated' nucleic acid is a long nucleic acid fragment for which at least one segment of the major axis of the molecule comprising at least 1 kb can be projected against a 2D plane, and does not overlap with itself. For clarity, for embodiments where-by long nucleic acid includes additional structure, for example as when the nucleic acid is contained in chromatin, compacted with histones, the major axis refers to the larger chromatin molecule, not the nucleic acid strand itself. Therefore statements in this disclosure such as "along the length of the molecule" when referring to long nucleic acid molecules, refers to along the length of the major axis.

3D Mapping. In this document, "3D mapping" refers to protocols that involve capturing the proximity relationship of at least two strands of nucleic acid, either of the same chromosome or not. For reference [Kempfer, 2020], and [Szabo, 2019] reviews these various techniques, of which a non-exhaustive list includes the following: 3C, 4C, 5C, Hi-C, TCC, PLAC-seq, ChIA-PET, Capture-C, C-HiC, Single-Cell HiC, GAM, SPRITE, ChIA-Drop.

Bind. "Binding", "bound", "bind" as used herein generally refers to a covalent or non-covalent interaction between two entities (referred to herein as "binding partners", e.g., a substrate and an enzyme or an antibody and an epitope). Any chemical binding between two or more bodies is a bond, including but not limited to: covalent bonding, sigma bonding, pi ponding, ionic bonding, dipolar bonding, metalic bonding, intermolecular bonding, hydrogen bonding, Van der Waals bonding. As "binding" is a general term, the following are all examples of types of binding: "hybridization", hydrogen-binding, minor-groove-binding, major-groove-binding, click-binding, affinity-binding, specific and non-specific binding.

Immobilized. As used herein, the term "immobilized" when used in reference to a molecules in direct or indirect attachment to a substrate via covalent or non-covalent bond(s) or stationery state by physical confinement or held stationery by an external force. Indirect attached to the substrate may be via at least one additional intermediary molecule or body. In certain embodiments, covalent attachment can be used, but all that is required is that the molecules remain co-localized to the substrate under conditions in which it is intended to use. Non limiting examples include the entire molecule may be held stationary with respect to the substrate, or a portion of the molecule held stationary with respect to the substrate, while the remainder of the molecule has limited freedom of movement, or the molecule is indirectly attached to the substrate via an intermediary, and the entire molecule has some limited freedom of movement. For example, immobilization of an oligonucleotide to a substrate can occur via hybridization of said oligonucleotide to a secondary oligonucleotide, said secondary oligonucleotide at least partially containing a complementary sequence to the first, and itself immobilized to the substrate.

In certain embodiments, a molecule may be immobilized on a surface via physisorption.

In certain embodiments, molecules can include biomolecules, nucleic acid molecules, proteins, peptides, nucleotides, or any combination thereof.

Certain embodiments may make use of a substrate which has been functionalized, for example by application of a layer or coating of an intermediate material comprising reactive groups which permit covalent attachment to biomolecules, such as polynucleotides.

Exemplary bonding examples include click chemistry techniques, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary bonding mechanism is set forth in U.S. Pat. Nos. [Pieken, 1998, U.S. Pat. No. 6,737,236]: [Kozlov, 2003, U.S. Pat. No. 7,259, 258]: [Sharpless, 2002, U.S. Pat. No. 7,375,234] and [Pieken, 1998, U.S. Pat. No. 7,427,678]; and U.S. Pat. Pub. No. [Smith, 2004, 2011/0059865], each of which is incorporated herein by reference.

Surface Energy. Surface tension of a fluid is the energy parallel to the surface that opposes extending the surface. Surface tension and surface energy are often used interchangeably. Surface energy is defined here as the energy required to wet a surface. To achieve optimum wicking, wetting and spreading, the surface tension of a fluid is decreased and is less than the surface energy, of the surface to be wetted. The wicking movement of a fluid through the channels of a fluid device occurs via capillary flow. Capillary flow depends on cohesion forces between liquid molecules and forces of adhesion between liquid and walls of channel. The Young/Laplace Equation states that fluids will rise in a channel or column until the pressure differential between the weight of the fluid and the forces pushing it through channel are equal. [Moore, 1962] Walter J. Moore, Physical Chemistry 3rd edition, Prentice-Hall, 1962, p. 730.

$\Delta p = (2\gamma \cos \theta)/r$ where $\Delta p$ is the pressure differential across the surface, $\gamma$ is the surface tension of the liquid, $\theta$ is the contact angle between the liquid and the walls of the channel and r is the radius of the cylinder. If the capillary rise is h and p is the density of the liquid then the weight of the liquid in the column is $\pi r2ghp$ or the force per unit area balancing the pressure difference is ghp, therefore:

$(2\gamma \cos \theta)/r = ghp$. For maximum flow through capillary channels, the radius of the channel should be small, the contact angle $\theta$ should be small and $\gamma$ the surface tension of the fluid should be large. The theoretical explanation of this phenomenon can be described by the classical model know as Young's Equation: $\gamma SV = \gamma SL + \gamma LV \cos \theta$, which describes the relationship between the contact angle $\theta$ and surface tension of liquid-vapor interface $\gamma LV$, the surface tension of the solid-vapor interface $\gamma SV$, and surface tension of the liquid-vapor interface $\gamma SL$. When the contact angle $\theta$ between liquid and solid is zero or so close to 0, the liquid will spread over the solid. A Contact angle measurement test is used as an objective and simple method to measure the comparative surface tensions of solids. In general, a material is considered to be hydrophilic when the contact angle in this test is below 90°. If the contact angle is above 90°, the material is considered to be hydrophobic.

Molecular Combing. Defined herein, "molecular combing" or "combing" refers to the process of immobilizing at least a portion of a macromolecule, in particular nucleic acid molecules, to a substrate surface, or within a porous film on a substrate surface, such that at least a portion of the macromolecule is elongated in a plane that is substantially parallel to the surface of said substrate. The elongated portion can be fully immobilized to the substrate, or at least of portion of said portion have some degree of freedom. In some embodiments at least a portion of the molecule is elongated within a porous material film parallel to the surface of said substrate, or at least a portion of the molecule is elongated on top of a porous material film parallel to the surface of said substrate, or at least a portion of the molecule is elongated and suspended between two points. In some embodiments, the substrate surface is at least part of a fluidic device.

In one embodiment, a single nucleic acid molecule binds by one or both extremities (or regions proximal to one or both extremity) to a modified surface (e.g., silanised glass) and are then substantially uniformly stretched and aligned by a receding air/water interface. Schurra and Bensimon (2009) "Combing genomic DNA for structure and functional studies." Methods Mol. Biol. 464:71-90; See also U.S. Pat. No. [Bensimon, 1995, U.S. Pat. No. 7,122,647], both of which are herein incorporated by reference in their entirety.

The percentage of fully-stretched nucleic acid molecules depends on the length of the nucleic acid molecules and method used. Generally, the longer the nucleic acid molecules stretched on a surface, the easier it is to achieve a complete stretching. For example, according to [Conti, 2003], over 40% of a 10 kb DNA molecules could be routinely stretched with some conditions of capillary flow, while only 20% of a 4 kb molecules could be fully stretched using the same conditions. For shorter nucleic acid fragments, the stretching quality can be improved with the stronger flow induced by dropping coverslips onto the slides. However, this approach may shear longer nucleic acid fragments into shorter pieces and is therefore may not suitable for stretching longer molecules. See e.g., [Conti, 2003] Conti, et al. (2003) Current Protocols in Cytometry John Wiley & Sons, Inc. and [Gueroui, 2002] Gueroui, et al. (Apr. 30, 2002) "Observation by fluorescence microscopy of transcription on single combed DNA." PNAS 99 (9): 6005-6010, both of which are hereby incorporated by reference in their entirety. See also [Bensimon, 1994, U.S. Pat. No. 5,840,862], [Bensimon, 1995, WO 97/18326], [Bensimon, 1999, WO 00/73503], [Bensimon, 1995, U.S. Pat. No. 7,122,647] which are hereby incorporated by reference in their entirety. [Lebofsky, 2003] "Single DNA molecule analysis: applications of molecular combing." Brief Funct. Genomic Proteomic 1: 385-96, hereby incorporated by reference in its entirety.

In some embodiments, the long nucleic acid molecule is attached to a substrate at one end and is stretched by various weak forces (e.g., electric force, surface tension, or optical force). In this embodiment, one end of the nucleic acid molecule is first anchored to a surface. For example, the molecule can be attached to a hydrophobic surface (e.g., modified glass) by adsorption. The anchored nucleic acid molecules can be stretched by a receding meniscus, evaporation, or by nitrogen gas flow. See e.g., [Chan, 2006] "A simple DNA stretching method for fluorescence imaging of single DNA molecules." Nucleic Acids Research 34(17): e1-e6, herein incorporated by reference in it entirety.

In the general methods described herein where-by one end of the molecule is bound to a surface during stretching, the nucleic acids can be stretched by a factor of 1.5 times the crystallographic length of the nucleic acid. Without being bound by a particular theory, the ends of the nucleic acid molecule are believed to be frayed (e.g., open and exposing polar groups) that bind to ionisable groups coating a modified substrate (e.g., silanized glass plate) at a pH below the pKa of the ionisable groups (e.g., ensuring they are charged enough to interact with the ends of the nucleic acid molecule). The rest of the double-strand nucleic acid molecule cannot form these interactions. As the meniscus retracts, surface retention creates a force that acts on the nucleic acid molecule to retain it in the liquid phase: however this force is inferior to the strength of the nucleic acid molecule's attachment; the result is that the nucleic acid molecule is stretched as it enters the air phase: as the force acts in the locality of the air/liquid phase, it is invariant to different lengths or conformations of the nucleic acid molecule in solution, so the nucleic acid molecule of any length will be stretched the same as the meniscus retracts. As this stretching is constant along the length of a nucleic acid molecule, distance along the strand can be related to base content.

Another embodiment, the nucleic acid molecule is stretched by dissolving the long nucleic acid molecules in a drop of buffer and running down the substrate. In a further embodiment, the long nucleic acid molecules are embedded in agarose, or other gel. The agarose comprising the nucleic acid is then melted and combed along the substrate.

In another embodiment, the molecule is attached to the substrate at least one specific point, allowing the remainder of the molecule a substantial amount of degree of freedom, such that portion of elongation in the molecule is obtained by the application of an external force on the molecule in a direction that is substantially parallel to the surface of the substrate. Examples of such embodiments include "DNA curtains" [Gibb, 2012] where-by the point of attachment is a controlled process, or the point of attachment can be random via interactions of the molecule with fluidic features, for example pillars as shown by [Craighead, 2011, U.S. Pat. No. 9,926,552].

Figure 2:
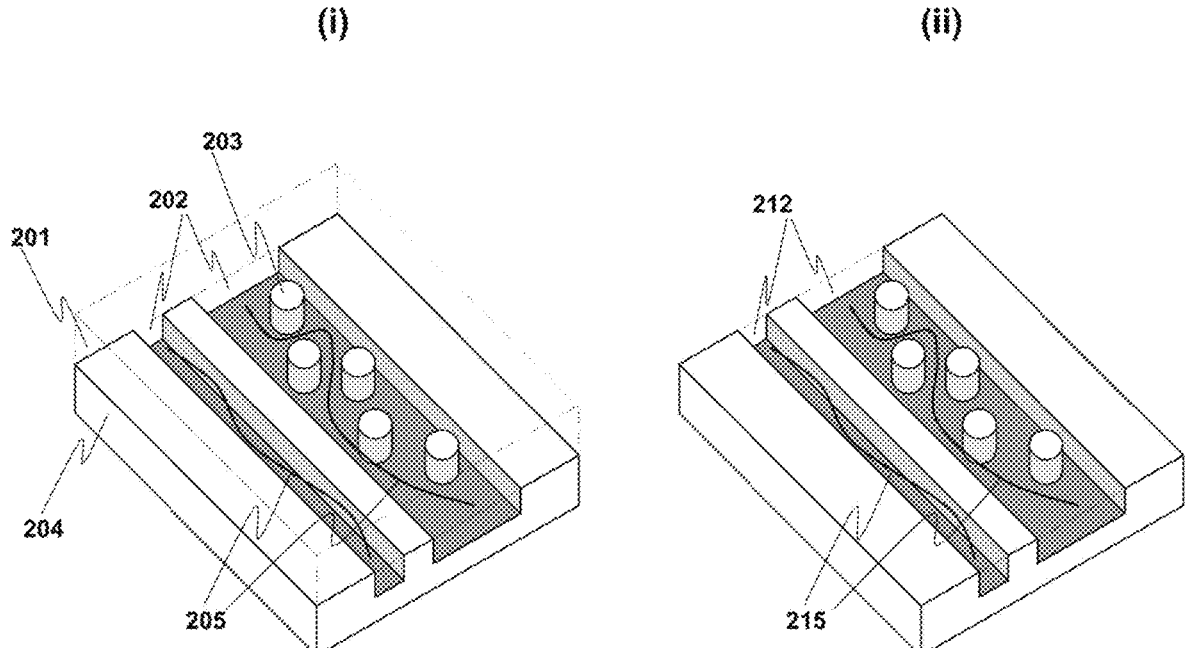
FIG. 2 demonstrates an enclosed fluidic device and method for generating combed linearly elongated nucleic acid molecule in parallel fashion, with (i) showing the molecules being flown into an enclosed channel, and with (ii) showing said molecules after the roof is removed from the channel.

In some embodiments, molecular combing can be done with fluid flow generated by elongating the molecule in a fluidic device such that after elongation in the device, the molecule is presented in an elongated state on the surface of the device, or within a porous film on the surface of the device. In one embodiment, the molecule is elongated via an elongation channel that can elongate the molecule via methods described elsewhere in this disclosure, including confining dimensions, external force, interaction with physical obstacles, interaction with a functionalized surface, or combination there-of. In some embodiments, the fluidic channels of the device not fully confined, such that after evaporation of the transporting solution, the molecules are at least partially immobilized on the surface of the device in an elongated state. Preferably, in some embodiments, the cross section of fluidic channels of the device is of triangular tapered shape, with wider opening at the top and infinitely narrower bottom, substantially enclosed or not fully enclosed, such that after evaporation of the transporting solution, the suspended molecules are drawn down towards increasingly confining narrower bottom to be increasingly elongated, at least confined in a small volume of solution or partially immobilized on the surface of the device in a linearized state. Preferably, in such embodiments with the cross section of fluidic channels of the device is of triangular tapered shape, with wider opening at the top and infinitely narrower bottom, the suspended molecules drawn down towards increasingly confining narrower bottom to be increasingly elongated and linearized, in ultra-confined small volume of solution or immobilized on the surface of the device, would be compatible with ultrahigh or super resolution imaging or interrogation. In some embodiments, as shown in in FIG. 2, a molecule 205 is elongated in a confined elongation channel of a microfluidic device (204), here with channel dimensions (202) that provide a confining environment and/or physical obstacles (203) that aid in promoting elongation. A gelling material within the solution that surrounds the molecule within the microfluidic device is then gelled. Finally, the molecules (215) are made accessible to the surface of the device via removal of the roof (201) while maintain the molecules within the gel film, or by using a porous roof material.

Microfluidic Device. The term "microfluidic device" or "fluidic device" as used herein generally refers to a device configured for fluid transport and/or transport of bodies through a fluid, and having a fluidic channel in which fluid can flow with at least one minimum dimension of no greater than about 100 microns. The minimum dimension can be any of length, width, height, radius, or cross-sectional axis. A microfluidic device can also include a plurality of fluidic channels. The dimension(s) of a given fluidic channel of a microfluidic device may vary depending, for example, on the particular configuration of the channel and/or channels and other features also included in the device.

Microfluidic devices described herein can also include any additional components that can, for example, aid in regulating fluid flow, such as a fluid flow regulator (e.g., a pump, a source of pressure, etc.), features that aid in preventing clogging of fluidic channels (e.g., funnel features in channels: reservoirs positioned between channels, reservoirs that provide fluids to fluidic channels, etc.) and/or removing debris from fluid streams, such as, for example, filters. Moreover, microfluidic devices may be configured as a fluidic chip that includes one or more reservoirs that supply fluids to an arrangement of microfluidic channels and also includes one or more reservoirs that receive fluids that have passed through the microfluidic device. In addition, microfluidic devices may be constructed of any suitable material(s), including polymer species and glass, or channels and cavities formed by multi-phase immiscible medium encapsulation. Microfluidic devices can contain a number of microchannels, valves, pumps, reactor, mixers and other components for producing the droplets. Microfluidic devices may contain active and/or passive sensors, electronic and/or magnetic devices, integrated optics, or functionalized surfaces. The physical substrates that define the microfluidic device channels can be solid or flexible, permeable or impermeable, or combinations there-of that can change with location and/or time. Microfluidic devices may be composed of materials that are at least partially transparent to at least one wavelength of light, and/or at least partially opaque to at least one wavelength of light.

A microfluidic device is typically designed and operated to manipulate a sample contained in a solution in order to achieve some desired outcome. The sample may be loaded into the device manually, for example using a pipette, or in an automated fashion, for example via an automated liquid handling system. In addition, various other solutions including buffers and reagents may be added simultaneously with the sample input, or separately, at different input ports and/or different time points. In some cases, the microfluidic device is manufactured with liquids and reagents contained within.

A microfluidic device can be fully independent with all the necessary functionality to operate on the desired sample contained within. The operation may be completely passive, such as with the use of capillary pressure to manipulate fluid flows [Juncker, 2002], or may contain an internally power supply such as a battery. Alternatively, the fluidic device may operate with the assistance of an external device that can provide any combination of power, voltage, electrical current, magnetic field, pressure, vacuum, light, heat, cooling, sensing, imaging, digital communications, encapsulation, environmental conditions, etc. The external device may be a mobile device such as a smart phone, or a larger desk-top device.

Figure 3:
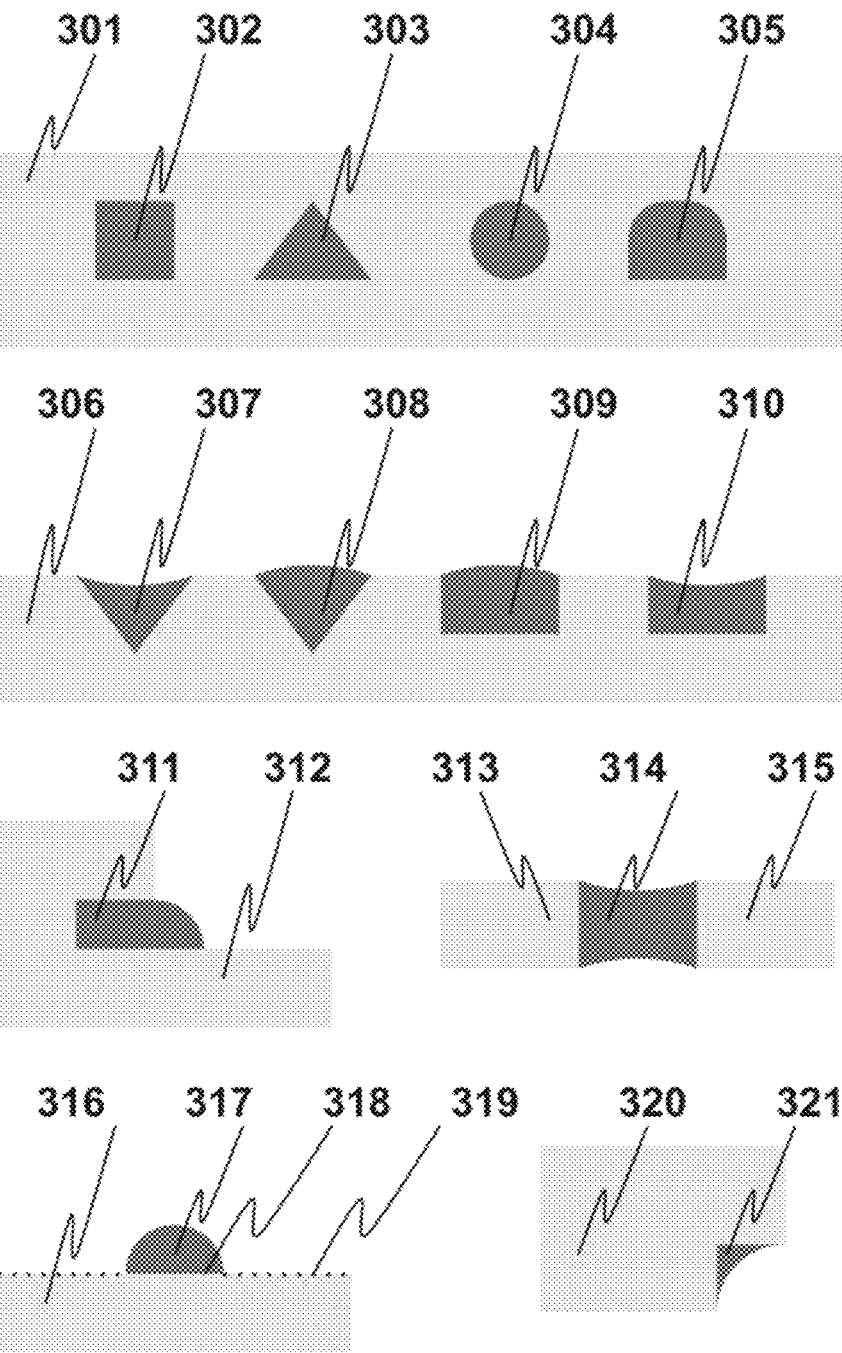
FIG. 3 demonstrates different, non-limiting embodiments of confined and non-confined channel types within a fluidic device.

The containment of the fluid within a channel can be by any means in which the fluid can be maintained within or on features defined within or on the fluidic device for a period of time. In most embodiments, the fluid is contained by the solid or semi-solid physical boundaries of the channel walls. FIG. 3 shows an example where-by channel walls with cross-sections such as rectangles (302), triangles (303), ovals (304), and mixed geometry (305) are all defined within a fluidic device (301). In other embodiments, fluidic containment within the fluidic device may be at least partially contained via solid physical features in combination with surface energy features [Casavant, 2013], or an immiscible fluid [Li, 2020]. Examples of a fluid being at least partially confined within physical boundaries include various channels physically defined on the surface of a fluidic device (306) such as grooves (307, 308) and rectangles (309, 310), all of which are filled with liquid of sufficiently minimal quantity, that surface tension allows for the liquid to be physically maintained within the channels, and not overflow. In other embodiments, the channel (311) could be a defined by a groove in a corner (312) of a fluidic device, or the channel (314) could be defined by two physically separated boundaries (313 and 315) of a fluidic device, or the channel (321) could be defined by a corner (320) of a fluidic device. In other embodiments, the channel (317) is defined by a hydrophilic section (318) on the surface of a fluidic device (316) where-by the hydrophilic section is bounded by hydrophobic sections (319) on the surface of the fluidic device. In all cases, these embodiments are non-limiting examples.

In some embodiments, the fluidic device includes an "electrowetting device" or "droplet microactuator", which is a type of microfluidic device capable of controlled droplet operations within the fluidic device via specific application of local electric fields. Non limiting examples of such devices include a liquid droplet surrounded by air on an open surface, and a liquid droplet surrounded by oil sandwiched between two surfaces. A detailed review of the various configurations of use, and physics of droplet control are provided by [Mugele, 2005] and [Zhao, 2013], both of which are provided here for reference.

It should be understood that some of the principles and design features described herein can be scaled to larger devices and systems including devices and systems employing channels and features reaching the millimeter or even centimeter scale channel cross-sections. Thus, when describing some devices and systems as "microfluidic," it is intended that the description apply equally, in certain embodiments, to some larger scale devices. In addition, it should be understood that some of the principles and design features described herein can be scaled to smaller devices and systems including devices and systems employing channels and features that are 100s of nanometers, or even 10s of nanometers, or even single nanometers in scale channel cross-sections. Thus, when describing some devices and systems as "microfluidic," it is intended that the description apply equally, in certain embodiments, to some smaller scale devices. As an example, a device may have input wells to accommodate liquid loading from a pipette that are millimeters in diameter, which are in fluidic connection with channels that are centimeters in length, 100s of microns wide, and 100s of nm deep, which are then in fluidic connection with nanopore constriction devices that are 0.1-10 nm in diameter.

A variety of materials and methods, according to certain aspects of the invention, can be used to form articles or components such as those described herein, e.g., channels such as microfluidic channels, chambers, etc. For example, various articles or components can be formed from solid materials, in which the channels can be formed via micromachining, film deposition processes such as spin coating and chemical vapor deposition, laser fabrication, photolithographic techniques, bonding techniques, deposition techniques, lamination techniques, molding techniques, etching methods including wet chemical or plasma processes, multiphase immiscible medium encapsulation and the like. For patterning, a variety of methods may be employed, including but not limited to: photolithography, electron-beam lithography, nanoimprint lithography, AFM lithography, STM lithography, focused ion-beam lithography, stamping, embossing, molding, and dip pen lithography. For bonding, a variety of methods may be employed, including but not limited to: thermal bonding, adhesive bonding, surface activated bonding, fusion bonding, anodic bonding, plasma activated bonding, laser bonding, and ultra sonic bonding.

In one set of embodiments, various structures or components of the articles described herein can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques [Xia, 1998, Whitesides, 2001].

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material. The device may be formed from glass, silicon, silicon nitride, silicon oxide, quartz. The device may be formed from a combination of different materials that are mixed, bonded, laminated, layered, joined, merged, or combination there-of.

Feature. Unless specifically stated otherwise, a "feature" is a region within or on the fluidic device defined by at least one boundary. In some embodiments, a boundary is defined by patterning. In some embodiments, a boundary may be a change in a physical topology, for example: a corner, a curve, an edge, a point, a depression, an inflection, a hill. Thus, for example, a feature may be channel, a wall, a pit, a hole, a pillar, a well, a floor, a roof. In some embodiments, a boundary may be a change in material composition or property, for example: a conductive material interfacing an insulating material, or a silicon nitride material interfacing with a silicon oxide material. Thus, a feature may be magnetic cube embedded in PMMA, or a polystyrene bead on glass surface. In some embodiments, a boundary may be change in a surface property, for example: a boundary may be a hydrophobic surface interfacing with a hydrophilic surface, or a non-functionalized surface interfacing with a functionalized surface. Thus, a feature may be a hydrophobic path on a hydrophilic COC surface, functionalized cell adhesion patterns among nonfunctionalized surface, or a circle functionalized with photo-cleavable barcodes on the surface of a silicon oxide substrate.

Physical Obstacle. Unless specifically stated otherwise, a "physical obstacle" is a physical feature within a fluidic device in which a long nucleic acid molecule, in the presence of an applied force, physically interacts with, such that the molecule's physical conformation or location is different than had said physical obstacle not been present. Non-limiting examples include: pillars, corners, pits, traps, barriers, walls, bumps, constrictions, expansions. The physical obstacles need not be physically continuous with the fluidic channel, but may also be additive to the device, with non-limiting examples including: beads, gels, particles.

Entropic barriers, entropic slopes, and entropic traps. A specific region of a nano or microfluidic device shall be defined as an "entropic barrier" if (a) the geometric shape of the device contains uneven features on the order of the size of the analyte of interest or less and (b) the diffusion or flow of the analyte around or through the features is significantly impeded or retarded in a manner that depends on the aggregate size, extended shape or conformation of the analyte. Furthermore, an "entropic trap" will be defined as region in a fluidic device where-by all fluidic connections are immediately through an entropic barrier such that if left at rest, the analyte of interest will remain in the trap, as the object occupying the trap is in a localized lowest energy state. The definition of Entropic Traps will be restricted to traps that are passive in nature in that they do not require a continuous supply of energy to hold an item or block its progression through a device, but do require energy to release it or cause it to pass through a barrier. The definition is further restricted to traps that are created by fabricating features such as pockets, constrictions, confinements, and physical obstacles into a fluidic device, and they can be partly or wholly defined by their geometry, and in turn lithographic artwork and processing parameters.

Entropic Traps allow for the spatial retention and positioning of packages, long polymer chain molecules and even subregions of long polymer chain molecules of interest. For brevity, all of these objects will be referred to as deformable objects in that their physical conformation can alter when in a confining fluidic device element, and they share many similarities governing their general behavior with respect to entropic traps and barriers. However, when their similarities diverge, or a particular feature of interest related to specific object is desired to reference, the specific object will be mentioned in the text.

Deformable objects can stay put in a trap, or against a barrier when buffer or surrounding fluid is flowed past at low velocity, permitting a change in chemical environment for reactions or the like. Further, traps can be designed to affect a change in the physical conformation of the deformable objects trapped within. While the geometry of various traps can look deceptively similar, their operating principles can vary significantly based on the size and composition of the trap and the deformable object to be trapped, as well as the chemical and local environment of the fluidic device that surrounds them. The methods of operation vary accordingly. The precise mechanisms of trap operation are a rich and ongoing area of physical investigation, but in most cases it is possible to enjoy the benefits of traps defined by geometry and method of use, without detailed understanding of the multiscale physical phenomena that underlie their use. Larger traps, such as traps for restraining intact cells or droplets, rely on elastic deformation of the object to be trapped, but are still referred to as Entropic Traps for consistency in this disclosure, as such objects similarly have a localized energy minimum when occupying a trap, and there exists a minimum applied force above which the deformable object can pass through any particular entropic barrier. This not entirely contrived: elasticity is a macro-scopic manifestation of entropic forces amongst others. Likewise, in the context of an oil/water droplet system an Entropic Trap can be used to manipulate the motion and behavior of water droplets and is understood to be driven by minimization of surface tension energy.

Entropic Traps and barriers form a broad family of building blocks that can be arranged to create a fluidic device for the manipulation deformable objects. They are complementary to other building blocks such as channels, which move the deformable object and various reagents, manifolds which combine or split channels and interrogation regions which facilitate observation of the deformable object. They are also complementary to stationary phase materials as understood in the field of chromatography, which employ chemical attraction between the deformable object and the surface of a fluidic device or surface of a mechanically constrained accessory such as chromatography resin or bead, and function to retard the flow of the deformable object in mobile phase passing through a device. Entropic Traps and barriers are often found that the intersection of channels and/or interrogation areas and can be placed inside or adjacent to channels and interrogation areas, regions with defined surface chemistry or other building blocks. A specific part of a fluidic device can have qualities of an Entropic Trap or barrier and as well as qualities of another type of building block.

The confinement energy of an Entropic Trap is classically understood as the difference in free energy exhibited by a specific example, not meant to be limiting, of a long polymer as it occupies various physical conformations throughout the structure. A long polymer that undergoes random thermal motion in the presence of an entropic trap will move to the portion of the trap with the lowest free energy. Free energy has two parts, first a temperature-invariant enthalpic component such as the energy of a chemical state, stretched or constrained chemical bonds, electrostatic attraction or repulsion etc. Second there is an entropic component that lowers free energy in a manner proportional to both the temperature and the entropy of a long polymer in that part of the device, which is the number of ways in which the long polymer can conform inside the device. The analysis of Entropic Traps typically only considers the entropic component of free energy and neglects the enthalpic portion. Comparing two regions of an entropic trap, it is necessary to count the number of ways in which a random coiled polymer can occupy the trap. For example, a tight cylindrical pipe that is only slightly greater than the polymer's outer diameter will only allow a linear molecule to fit in two ways: forwards or backwards. In contrast, a large open volume will allow a combinatorial number of random runs, kinks and conformations. As there are more states in the latter case, the entropy of that geometry is higher, and the free energy of the long polymer in that area is correspondingly lower.

As the deformable objects move within a fluidic device to minimize free energy, they are said to fall into and occupy an Entropic Trap when they occupy a region of the device that allows for a localized lowest energy state. A deformable object that is entirely confined within a portion of a device with uniform geometry, but which does not extend into a neighboring trap will not spontaneously move into the trap, but will instead freely diffuse and move in response to external forces. However, when a portion of the deformable object diffuses into or is moved into region of the fluidic device which constitutes an entropic barrier from the reverse perspective, such fluidic element is an entropic slope, as the molecule will be drawn through the slope. Put in other terms, without an external force, a deformable object in certain physical conformation and location A within a fluidic device can lower its total energy by passing through an Entropic Slope to a new physical conformation and location B. However, the reverse is not possible without the addition of a minimum external applied force that allows the object to transfer through the entropic barrier from B to A.

A deformable object is freed from a trap when the difference in free energy from the trapped state to the liberated state is changed such that the free state now has a lower energy. For long polymers, this is typically accomplished by modulating the enthalpic portion of free energy by subjecting the molecule to an external force such as hydrodynamic drag from fluid flow or the application of an electric field to a molecule with net charge such as DNA.

The strength of the trap is understood in a probabilistic sense, in that the probability of escape from the trap decreases with increased trap energy. A well balanced trap will retain an item until displaced by means of an external force on the item, or by manipulation or modulation of the intrinsic trap itself.

The behavior of smaller traps that trap long polymers are influenced by, and can be modulated by, the chemical character of the long polymer, which can in turn be modulated by buffer conditions and the local chemical environment. On shorter length scales, the direction of extension of one segment of a polymer depends on the direction of the segments preceding it and is quantified by the intrinsic parameter known as the persistence length of the long polymer. A conformation that requires a long polymer to bend sharply relative to the persistence length will incur a spring energy. Self-avoidance dominates longer length scales, as when a polymer loops around it cannot overlap with prior segments. This loss of entropy is described by an excluded volume energy that is proportional to the molecule's diameter and net electrostatic charge.

In some embodiments, the deformable object is able to overcome entropic barriers at least partially due to a change in environmental conditions (for example temperature, pH, pressure) which act to reduce, or completely remove, the entropic barrier. For example, a long nucleic acid molecule can have it's radius of gyration altered by modifying the ionic concentration of the solution, thus allowing entropic barrier energy height to manipulated [Dai, 2016].

A long polymer chain (such as nucleic acid) left at rest in a solution will form a random coil configuration with outer boundaries that can be approximated as a sphere, and whose radius is governed by the properties of the solution and the molecule itself. This is the lowest energy state of polymer in a solution, and it will naturally return to this state if left unperturbed within the solution. However, when the polymer is in the presence of physical features and/or external forces that limit the polymer's ability to occupy a random coil conformation, the polymer chain will be physically manipulated into a higher energy state. Conversely, when physical boundaries and/or external forces are removed, the polymer chain will return to the spherical random coil configuration [Reisner, 2005] [Han, 2007] [Dai, 2016].

The interaction of long nucleic acid fragments with entropic traps and barriers in a fluidic environment was previously demonstrated [Craighead, 1999, U.S. Pat. No. 6,635,163]. Here the entropic barrier is an increase in physical confinement such that when a nucleic acid fragment transitions into the region of higher confinement, the nucleic acid's overall energy state increases. The amount of energy state change depends on the physical feature dimensions, the solution composition, and the polymer's physical properties. The energy increase provides a barrier, such that without a sufficiently large externally applied force, the long nucleic acid fragment will not move into the higher energy state. However, by applying a sufficiently large external force, the long nucleic acid molecule can be made to occupy the more confined region [Craighead, 1999, U.S. Pat. No. 6,635,163].

Similarly, a long nucleic acid molecule in an entropic trap will not escape, unless a sufficiently large external force is applied. Furthermore, a long nucleic acid fragment that is brought into physical contact with said trap, for example via an external force or Brownian motion, will relax into the trap. A long nucleic acid molecule will relax into the trap until its total energy state is minimized. As such, if the trap's physical dimensions are sufficiently small, only a portion of the long nucleic acid fragment may occupy the trap. This was demonstrated previously where-by small 'pits' (traps) were employed to capture sub-units of the long nucleic acid molecule in deformable objects composed of random coils in each trap, with the objects interconnected to each other by elongated portions of the molecule forming a "pearls on string" configuration [Reisner, 2009].

In addition to long nucleic acids molecules (long polymers), droplets (and in some cases cells) are also deformable objects that can be manipulated by entropic barriers, slopes, and traps. A droplet flowing in a channel will stop at a constriction (entropic barrier), and will not pass unless a sufficiently large force is applied on said drop (eg: pressure). Furthermore, a droplet can be trapped between two constriction points, and thus in an entropic trap, again until a sufficiently large external force (eg: pressure) is applied to release the droplet from the trap. [Tan, 2004 [Fraden, 2007, U.S. Pat. No. 8,592,221] [Baroud, 2010]. Another example of an entropic trap is demonstrated by [Abbyad, 2011] in which droplets are "pinned" ("trapped") along a rail, as the droplet has a localized lower energy state by relaxing into the rail structure.

Figure 4:
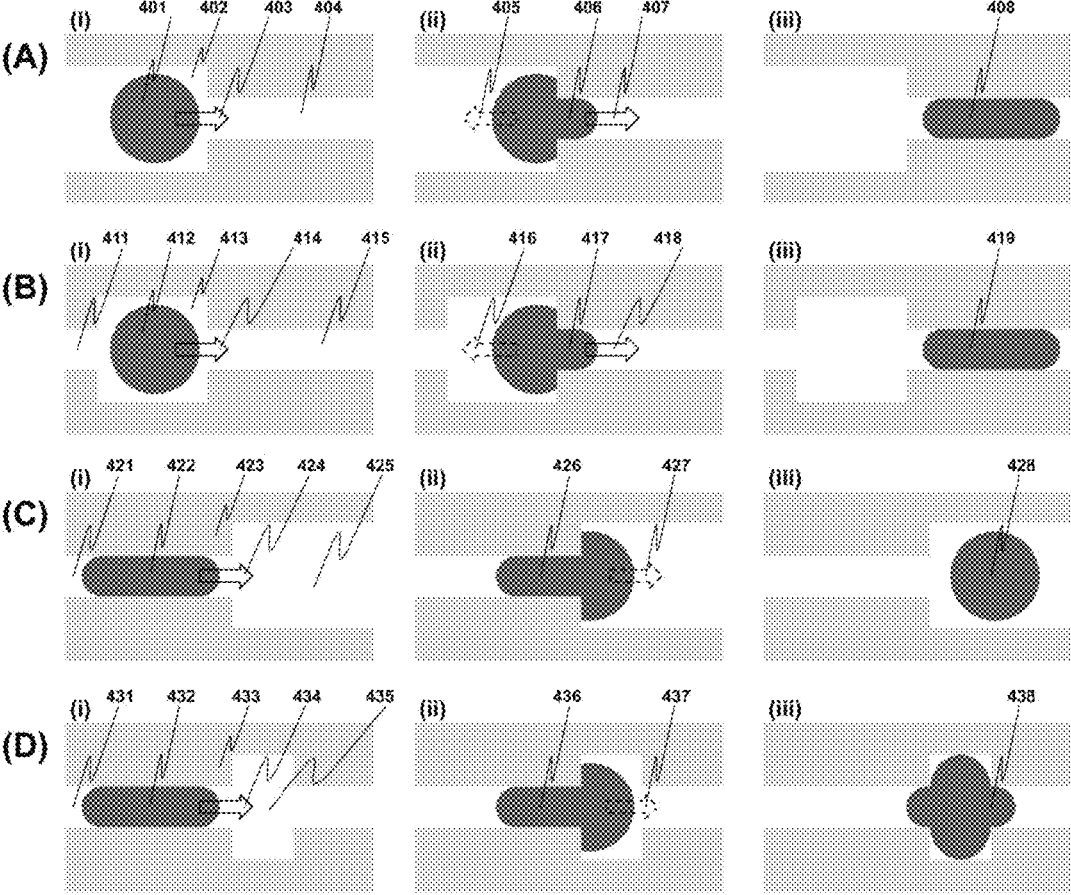
FIG. 4 demonstrates various fluid device embodiments of a deformable object encountering entropic barriers, slopes and traps. (A) an object encounters an entropic barrier. (B) an object escapes from an entropic trap. (C) an object encounters an entropic slope. (D) an object encounters an entropic trap.
Figure 5:
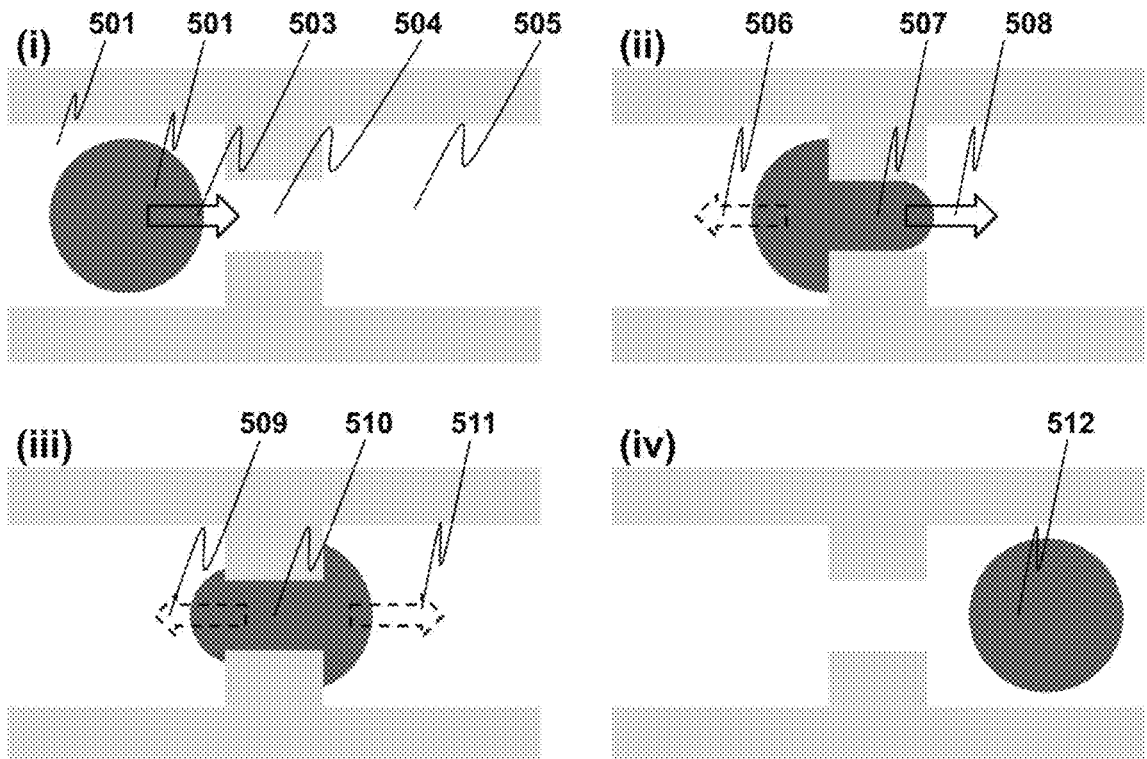
FIG. 5 demonstrates a deformable object encountering an entropic barrier.

FIGS. 4 and 5 demonstrates some non-limiting examples of the interaction of entropic barriers, slopes, and traps with a deformable object when an external force is applied. All examples in FIGS. 4 and 5 are descriptive only, not wishing to be bound by any particular theory, and neglect secondary forces such as friction, Brownian motion, or pressure variation due to fluid displacement. In addition, the following examples described in FIGS. 4 and 5, an entropic barrier and/or slope are formed by the intersection of a wider channel with a narrower channel. In the Figures, the deformable object in its lowest energy conformation is described as a sphere which is reasonably accurate geometric approximation for a water-in-oil droplet. However for more complicated deformable objects that are composed of a non-homogenous material, long polymer chains, or structural asymmetries (eg: metaphase chromosomes), the lowest energy state conformation will be different. These non-limiting physical examples of an entropic barriers and slopes are purely for illustrative purposes and are meant to be simple demonstrations.

FIG. 4(A)(i,ii,iii) shows an example of a deformable object (401) in proximity to an entropic barrier, here identified as the intersection of the larger channel (402) with the narrower channel (404). With no external force applied, the object (401) will not enter the narrower channel (404), as doing so would require increasing the object's energy state. As such an external force (403) must be applied on the object otherwise it will remain within the larger channel (402). With an external force applied (407), the object will approach the entropic barrier and begin to deform (406) into a higher energy state. While the object is at least partially localized within the entropic barrier, a relaxing force (405)

will pull the object back into larger channel. The magnitude of the relaxing force is dependent upon many factors, including the degree of deformation of the object, and how much of the object remains within the entropic barrier. If the external force (407) is sufficiently large to overcome the relaxing force (405), the object will overcome the entropic barrier. With no part of the object remaining within the barrier, the object to remain at rest at a higher energy state (408).

FIG. 4(B)(i,ii,iii) shows an example of a deformable object (412) in an entropic trap (413), in that all fluidic connections of the larger channel (413) are through one of two entropic barriers. The first entropic barrier being located at the interface of the larger channel (412) and narrower channel (415), and the second entropic barrier being located at the interface of the larger channel (412) and the narrower channel (411). With no external force applied, the object will remain in the trap indefinitely. However, by applying an external force (414), the object can be brought towards one of the entropic barriers, here the interface of 413 and 415. With an external force applied (418), the object will approach the narrow channel and begin to deform (417) into a higher energy state. While the object is at least partially localized within the entropic barrier, a relaxing force (416) will pull the object back into larger channel. The magnitude of the relaxing force is dependent upon many factors, including the degree of deformation of the object, and how much of the object remains within the entropic barrier. If the external force (418) is sufficiently large to overcome the relaxing force (416), then the object will overcome the entropic barrier, with no part of the object remaining within the barrier, allowing the object to remain at rest at a higher energy state (419).

FIG. 4(C)(i,ii,iii) shows an example of a deformable object (422) at rest in a deformed shape within a narrower channel (421), which is fluidically connected to a larger channel (425). The narrower channel (421) and larger channel (425) interface identifies an entropic slope with respect to the object's current state (422). An application of an external force (424) can bring the object into the presence of the entropic slope. When at least a part of the object has entered the slope, a relaxing force (427) will act to relax the object to lower energy state (426), moving the object into the larger channel. Once the object has exited the slope, the object will be at rest at a lower energy state (428) on the other side of the slope.

FIG. 4(D)(i,ii,iii) shows an example of a deformable object (432) at rest in a deformed shape within a narrow channel (431), which is fluidically connected to a larger channel (435). The narrower channel (431) and larger channel (435) interface identifies an entropic slope with respect to the object's current state (432). An application of an external force (434) can bring the object into the presence of the entropic slope. When at least a part of the object has entered the slope, a relaxing force (437) will act to relax the object to lower energy state (436), moving the object into the larger channel. In this example, the larger channel is insufficiently large to allow the object the freedom to completely relax to its lowest possible free energy state, however the final energy state of the object (438) is lower than the original state of the object (432), thus the object is now in an entropic trap (438).

FIG. 5 (i,ii,iii,iv) shows an example of a deformable object (501) in proximity to an entropic barrier, here identified as the intersection of the larger channel (501) with the narrower channel (504). With no external force applied, the object (501) will not enter the narrower channel (504), as doing so would require increasing the object's energy state. As such an external force (503) must be applied on the object otherwise it will remain within the larger channel (502). With an external force applied (508), the object will approach the entropic barrier and begin to deform (507) into a higher energy state. While the object is at least partially localized within the entropic barrier, a relaxing force (506) will pull the object back into larger channel. The magnitude of the relaxing force (506) is dependent upon many factors, including the degree of deformation of the object, and how much of the object remains within the entropic barrier. Provided the external force (508) is large enough to overcome the relaxing force (506), in this example the object is introduced to an entropic slope defined as the interface of the narrow channel (504) with the larger channel (505). Once in the presence of this entropic slope, an additional relaxing force (511) will act on the object in the direction of the larger channel (505). Again, the magnitude of the second relaxing force is a function of several parameters, including the physical position of the object within the slope. With the external force (508) still applied, at a certain point the secondary relaxing force (511) will overcome the first relaxing force (509), thus moving the object into the larger channel (512), with or without the external applied force.

For all embodiments, the physical confining dimensions of the entropic barrier and traps will be a function of the deformable objects in which the barrier and traps are designed to interact with. For example, a 300 nm nano-pit is appropriately sized to capture a 10 kbp segment of a 500 kbp long nucleic acid molecule, where-as a 20 micron constriction is appropriately sized to be a barrier for a 1 nL water-in-oil droplet.

Package. A "package" is any body capable of holding contents within the defined boundary of the body. In some embodiments, the boundary is defined by a physical barrier such as a lipid bilayer or a surfactant. In some embodiments there is no barrier, such as a droplet formed by mixing two immiscible fluids. A non-exhaustive list of packages include: cells, nucleus, vesicles, exosomes, mitochondria, organelles, bacteria, virus, bubble, artificial membrane package, water-in-oil droplets, oil-in-water droplets, water-oil-water droplets, oil-water-oil droplets. In all cases, the package can be lysed (or ruptured) by various means to release the contents.

Lysing. "Lysing" (or "Rupturing") is the process of weakening the package boundary such that the contents can more easily be released from the package. In some embodiments, the package boundary is non-recoverably destroyed with the contents released. In some embodiments, the package boundary is disrupted, and whose integrity may be recovered. In some embodiments, the package boundary is permanently or temporarily made more permeable. Examples of different lysing methods include chemical, enzymatic, electro-chemical, physical, mechanical, acoustic, electroporation and focused photons. Suitable lysing agents include, for example, enzymes (e.g., protease, glycosidases, nucleases). Exemplary enzymes include lysostaphin, pepsin, glucosidase, galactosidase, lysozyme, achromopeptidase, endopeptidases, N-acetylmuramyl-L-alanine amidase, endo-beta-N-acethylglucosaminidase, ALE-1, DNase, and RNase. Other lysing agents include salts (e.g., chaotrophic salts), solubilizing agents (e.g., detergents), reducing agents (e.g., beta-mercaptoethanol (BME), dithiothreitol (DTT), dithio-erythritol (DTE), tris(2-carboxyethyl) phosphine hydrochloride (TCEP: Pierce Chemical Company, Rockford, Ill.), cysteine, n-acetyl cysteine), acids (e.g., HCl), and bases (e.g., NaOH). Various combinations of lysing agents and/or methods can be used if desired.

Focused photos to lyse packages, or "optical lysis", has been demonstrated previously [Baeummer, 2001, U.S. Pat. No. 6,815,209] by using a laser light of wavelength from 500 nm to 3500 nm to lyse cells in solution, or by short pulses [Allbritton, 1998, U.S. Pat. No. 6,156,576]. A review of various methods for focused light lysing of cells was reported by [Islam, 2017] in which optically induced dielectrophoresis (ODEP) is a process by-which a focused laser pulse at the cell-solution interface creates a cavitation bubble that lyses the cell. Focused laser lysing was further demonstrated [Meldrum, 2014, U.S. Pat. No. 10,221,443] as an effective means of lysing specific individual cells within a cluster of cells, typically a tissue sample.

Gel and gelling agent. "Gels" are defined as a substantially dilute or porous system composed of a "gelling agent" that has been cross-linked ("gelled"). Non-limiting examples of gels include agarose, polyacrylamide, hydrogels [Caló, 2015], DNA gels [Gačanin, 2020]. In the context of this document, a gel and a semi-gel are equivalent, where-by a semi-gel is a gel with incomplete cross-linking and/or low concentration of the gelling agent.

External Force. An "external force" is any applied force on a body such that the force that can perturb the body from a state of rest. Non-limiting examples include hydrodynamic drag exerted by a fluid flow [Larson, 1999] (which can be imitated by a pressure differential, gravity, capillary action, electro-osmotic), an electric field, electric-kinetic force, electrophoretic force, pulsed electrophoretic force, magnetic force, dielectric-force, centrifugal acceleration or combinations there-of. In addition, the external force may be applied indirectly, for example if bead is bound to the body, and then the bead is subjected to an external force such a magnetic field, or optical teasers.

Retarding Force. A "retarding force" is any force that retards a body's movement in the presence of an external force. Non-limiting examples include any of the following, or combination there-of: an entropic barrier, shear force, Van der Waals force, a physical obstruction, binding to surface (such as a substrate or bead), a gel, an artificial gel. It should be noted that the retarding force need not keep the body motionless, or maintain a zero-average velocity. In some cases, the retarding force may itself be an external force, such that two external forces counter-act each other, one acting to retard the body's movement in the direction of the first external force.

Dispensing System. Used herein, a "dispensing system" or "dispenser" is an instrument, or a component of an instrument that is capable of dispensing a volume of liquid from a dispensing tip, nozzle, or orifice (herein, collectively referred to as "tip") at a desired location in (x,y,z) space. In some embodiments the liquid is dispensed as a continuous stream. In some embodiments, the liquid is dispensed as a series of drops. The drop size may be 100 micro liters or less, 10 micro liters or less, 1 micro liters or less, 100 pico liters or less, 10 pico liters or less, 1 pico liters or less, 100 femto liters or less, 10 femto liters or less, 1 femto liter or less, 100 atto liters or less, 10 atto liters or less. In some embodiments, the tip is composed of a consumable pipette tip. In some embodiments, the dispenser tip is also capable of extracting solution from a target solution in (x,y,z) space, and so the dispenser is also an "extractor". In some embodiments, the dispensing and extraction tips are different tips. In some embodiments, they are the same. In some embodiments, the tip is a micro-syringe, or the end of a capillary tube, or a nozzle. In some embodiments, the dispensing of liquid is controlled by air-displacement via a pressured air-line, or a syringe-pump moved via an electrical-mechanical system, such as a stepper motor.

In some embodiments, inkjet dispensers may be used. Inkjet printing includes continuous jet (CJ) and drop-on-demand jet (DODJ). The CJ based on the transducer, charging electrode and electric field can produce the droplet continuously, and the droplet location on a substrate can be determined by its charging density. There are several kinds of actuators for the DODJ device, including piezoelectric, thermal, solenoid, pneumatic, magnetostrictive and acoustic actuators. There are two actuation modes for the piezoelectric micro-jet devices in particular, including single actuation mode and hybrid actuation mode. The single actuation mode includes shear mode, squeeze mode, bend mode, push mode and needle-collision mode, while the hybrid actuation mode refers to electrohydrodynamic (EHD) assistant actuation. A detailed review of different inkjet technologies is provided by [Li, 2019], and included here for reference in its entirety.

In some embodiments the dispenser consists of a contact probe capable of transporting and depositing a drop of solution by contact wetting. In some embodiments, extraction of drop from a surface is done by a contact probe making contact with said drop, and wetting the contact probe.

Contact Probe System. Used herein, a "contact probe" system is an instrument, or a component within an instrument that is capable of positioning the point of a contact probe within the desired location in (x,y,z) space, preferably with nanometer position accuracy or better. In the preferred embodiments, the contact probe is capable of generating a signal based on its interaction with a physical object. In the preferred embodiments, the contact probe is a surface scanning probe, capable of generating a signal while the probe is physically moved in space by the instrument. Different types of probes include SPM (Scanning Probe Microscopy), AFM (Atomic Force Microscopy), STM (Scanning Tunneling Microscopy), SPE (Scanning Probe Electrochemistry). For a review of different Scanning Probe Microscopy systems, refer to [Takahashi, 2017]. In some embodiments, the contact probe can operate in a dry environment, or a humid environment, or a liquid environment. In some embodiments, the point of the contact probe can be functionalized with chemical moieties, biological bodies, or affinity groups to enable biochemical interaction with the physical object being probed. For a review of various functionalization that have been demonstrated on contact probes, refer to [Ebner, 2019]. In some embodiments, the point of the contact probe may include a carbon nanotube, a nanorod, or a nanospike.

Passive Microfluidic Device for Cytogenetic Analysis

In this set of embodiments, we disclose devices and methods for a fluidic device consumable that enables the positioning ("spread") of nucleic acid material for interrogation in a manner that improves the data quality via the controlled physical arrangement of the long nucleic acid molecules within the interrogation region of the device in a passive fashion, such that no internal or external power source is required to control the movement and positioning of the packages and nucleic acid molecules after the input sample is dispensed into the device, except the movement are driven by forces including but not limiting to surface energy, entropic differential, phase, temperature or pressure differential, gravity, capillary action, electro-osmotic or micro-convection flow.

Some device and method embodiments described herein are designed for the generation of large nucleic acid molecule spreads in such a manner that the large nucleic acid molecules originating from a single package are co-located and substantially non-overlapping on the surface of the fluidic device, providing higher yields and improved data quality compared over a standard microscope slide using common chromosome preparation methods [Grubb, 2015] in which the chromosomes are positioned randomly on the surface of a microscope slide. In some embodiments, the nucleic acid molecule spreads consist of long nucleic acid molecules immobilized on the surface of the fluidic device. Some device and method embodiments described herein are designed for the generation of elongated long nucleic acid fragments on the surface of the microfluidic device, providing reduced variability in stretch and molecule overlapping compared to common fiber-FISH and DNA-combing protocols.

A critical parameter in preparation of chromosome spreads for cytogenetic analysis is the density and dispersal of cells on the surface such that genetic information can be interrogated with minimum ambiguity. The primary goal of chromosome spreading is to achieve uniform dispersal of chromosomes within a discrete area that represents the genetic content of one cell, with chromosomes elongated and avoiding overlap as much as possible. In this series of embodiments, the patterned surface features on the fluidic device allows for designed fluid flows driven by capillary or micro-convention forces that allows for more improved adherence of the individual cells, efficient ruptures of cell membranes, and more optimized arrangement of chromosomes for interrogation, including more controlled separation, alignment, elongation, and drying, when compared to similar conventional random chromosome spreads. Here, in this set of embodiments, the molecules are completely confined and isolated in microgrooves, pillar posts or entropic traps within the enclosed microfluidic system minimizing their physical overlapping, thus the interrogation of the target molecules and chromosomes are contained in limited area around the patterned regions. Unlike conventional slides configuration, where-by the cell suspension begins to dry as the fixative evaporates in random uncontrolled manner, leading to uneven spreading, and often yielding a "broken" or lost metaphase preparation.

In one preferred embodiment, the fluidic device is preferably compatible with any of the existing infrastructure of cytogenetic labs including reagents, sample preparation, sample dispensing, liquid dispensing, automated handling, imaging systems, or analysis software. In one preferred embodiment, the form-factor of the device is compatible with standard microscope slide 25 mm by 75 mm in size. In some embodiments, the device is composed of an optically transparent fluidic device, for example plastic, glass, or quartz. In some embodiments, the device is composed of COC, PMMA, PC, Silicon, or a non-transparent glass. In some embodiments, a coverslip is added by the user, while in other embodiments, the coverslip is incorporated into the device.

Sample inputs, reagents and dye addition, washing can all be done via manual or automated dispensing or dipping steps which are similar in fashion to that normally performed for preparing spread chromosomes on standard microscope slides. In some embodiments the microfluidic device can include fiducial markers or alignment markers that can be used to enable visual alignment of the device either manually or with automated imaging systems. In some embodiments, there are multiple zones on the fluidic device, with each zone designed to physically isolate different cells or samples. In some embodiments, there are fiducial markers on the device that guide the user or automated dispensing system where on the device to dispense the solution. In some embodiments there are fiducial markings or physical reference points on or in the device that guide the user or automated data acquisition imaging system as to the orientation of the device or interrogation region(s). In some embodiments, there are fiducial markers on the device that guide the user or automated dispensing system where on the device to dispense the solution. Physical reference points could include notched or rounded corner(s). In some embodiments at least one well or topologically recessed regions is integrated onto the surface of the device to aid in solution containment during dispensing, or to provide guidance.

In one preferred embodiment of the device and methods, long nucleic acid molecule spreads are generated on the device surface from an input sample solution of suspended packages. Once the solution is dispensed into or on the device, fluidic forces inherent from solution's interaction with the device's physical interface and surrounding environment, along with associated methods, enable the consistent positioning of package's large nucleic acid molecules in the interrogation region of the device such that the probability of said molecules overlapping or self-folding is reduced when compared to a standard slide preparation. The spreads of large nucleic acid molecules are physically co-located with other molecules from the same package, and sufficiently separated from an adjacent package's molecules to enable grouping identification via imaging. In one preferred embodiment, the package is a cell in a hypotonic state, and the large nucleic acid molecules are chromosomes in one of the more condensed phases such as prophase or metaphase.

In addition to condensed pro- or metaphase chromosomes, chromosomes of different phases are also possible. For example, deposition of interphase chromosomes for use with FISH applications. Furthermore, the nucleic acid being deposited may be a portion of a chromosome such as extra-chromosomal DNA (ecDNA), or nucleic acid originating from a source other than chromosomes such as mitochondrial DNA, an artificial mini-chromosomes, or microbial originated DNA. The nucleic acid may be in chromatin form. The nucleic acid may be a long nucleic fragment, thus enabling fiber-FISH applications. Much like DNA-combing methods, long nucleic fragments will be aligned and elongated onto a surface to enable cytogenetic applications. However here, due to the patterned surface features or differential entropic energies, the long nucleic acid fragments will be aligned, arranged or elongated in a controlled manner rather than a purely random process. In addition, unlike combing that requires dipping a slide into a pool of sample, here the input sample can be dispensed via a pipette or probe in small quantities of 10s of microliters or less, and thus the input sample volume requirements are considerably less.

Described within are a multitude of different device embodiments. However, most embodiments share some basic functionality. First, an input sample comprising of suspended packages is introduced into the device. Second, the package contents of long nucleic acid molecules are spread within the interrogation region of the device. Third, the long nucleic acid molecules are prepared for interrogation, typically via exchange or reagent solutions and rinses and additional processing. Forth, the long nucleic acid molecules are optically or electronically interrogated while in the interrogation region.

The reagent materials and solutions include any commonly used by someone trained in the art of performing cytogenetic analysis. These reagents include various stains, dyes, fixatives, and solvents. Additional reagents may include various dyes for physical mapping, FISH-probes, labelling bodies, methylation dyes, non-methylation dyes.

In some embodiments, prior to dispensing onto the fluidic device, or after dispensing onto the fluidic device, long nucleic acid molecules are labelled with a labelling body to generate a physical map. In some embodiments, the physical map is a karyotype. In some embodiments, the physical map is a linear physical map. In the preferred embodiment, the physical map is an AT/CG density linear physical map.

In some embodiments, the surface of at least one of the boundary walls of the fluidic device that constitutes the interrogation region are modified to change the surface energy or add functionalization to promote nucleic acid molecule immobilization with the said surface. In some embodiments, a specific region of functionalization on the device surface is designed to immobilize a specific target of macromolecule. In some embodiments, the specific target is a type of chromosome. In some embodiments, the functionalization is designed to promote cell lysing or rupture, such as chip surface treated with chemical or enzymatic coating activated upon wetting or by co-factors in sample loading to be in contact with target cells or molecules.

In addition to traditional cytogenetic methods and procedures where-by once spread on a slide, the main method of interrogation is via optical imaging, this set of embodiment devices and methods in which the nucleic acid molecules are arranged in a more controlled manner on the device surface is highly amendable to other forms of interrogation and processing, either separately from optical imaging, or in conjunction with optical imaging. In one preferred embodiment, the optical imaging is used to select specific long nucleic acid molecules for specific additional interrogation and processing. Non limiting examples of interrogation and processing methods that can be performed on the macromolecules include: interrogation with a contact probe system, an Atomic Force Microscopy (AFM), a Scanning Tunnelling Microscopy (STM), a Scanning Probe Microscopy (SPM), a Transmission Electron Microscopy (TEM), a Scanning Electron Microscopy (SEM), capture and removal from the surface with a contact probe system, or submergence in solution dispensed from a dispending system, PCR amplification or Sequencing. In a further extension of the embodiment, the at least one nucleic acid molecule in a drop of solution could be resuspended into the drop solution, and in another additional embodiment, said drop containing the at least one molecule can be extracted from the surface.

Long Nucleic Acid Spreads Via Interaction with a Patterned or Modified Surface on a Microfluidic Device In this set of embodiments, the long nucleic acid molecule spreads are generated via the interaction of the molecules with patterned surface features of a microfluidic device consisting of physical geometries or surface energy changes that are of the length scale of the nucleic acid in question. In the preferred embodiment, the length scales are sufficiently large to accommodate a single large nucleic acid molecule along one dimension. For example, the patterned features may consist of channels that are patterned of size to accommodate a single or multiple human chromosomes in a single-file fashion, and are thus preferably approximately 1-5 microns in width. Alternatively, the patterned features may consist of channels that are patterned of size to accommodate a long nucleic acid molecule in an elongated state, and thus preferably 5-1000 nm in width. The patterned features may have variable widths or variable depths, that change randomly, or due to some design intent over the surface of the fluidic device. The patterned features may have a regular period or pattern, or random in their arrangement on the fluidic device surface. The patterned features can consist of any shape or dimension that is within the physical length scale of the molecule interrogated, or may include the following non-limiting examples: channels (isolated, connected, networked), pits, pillars, corners, chevrons, branches, forks, or intersections. The patterned features may include physical obstacles.

Figure 6:
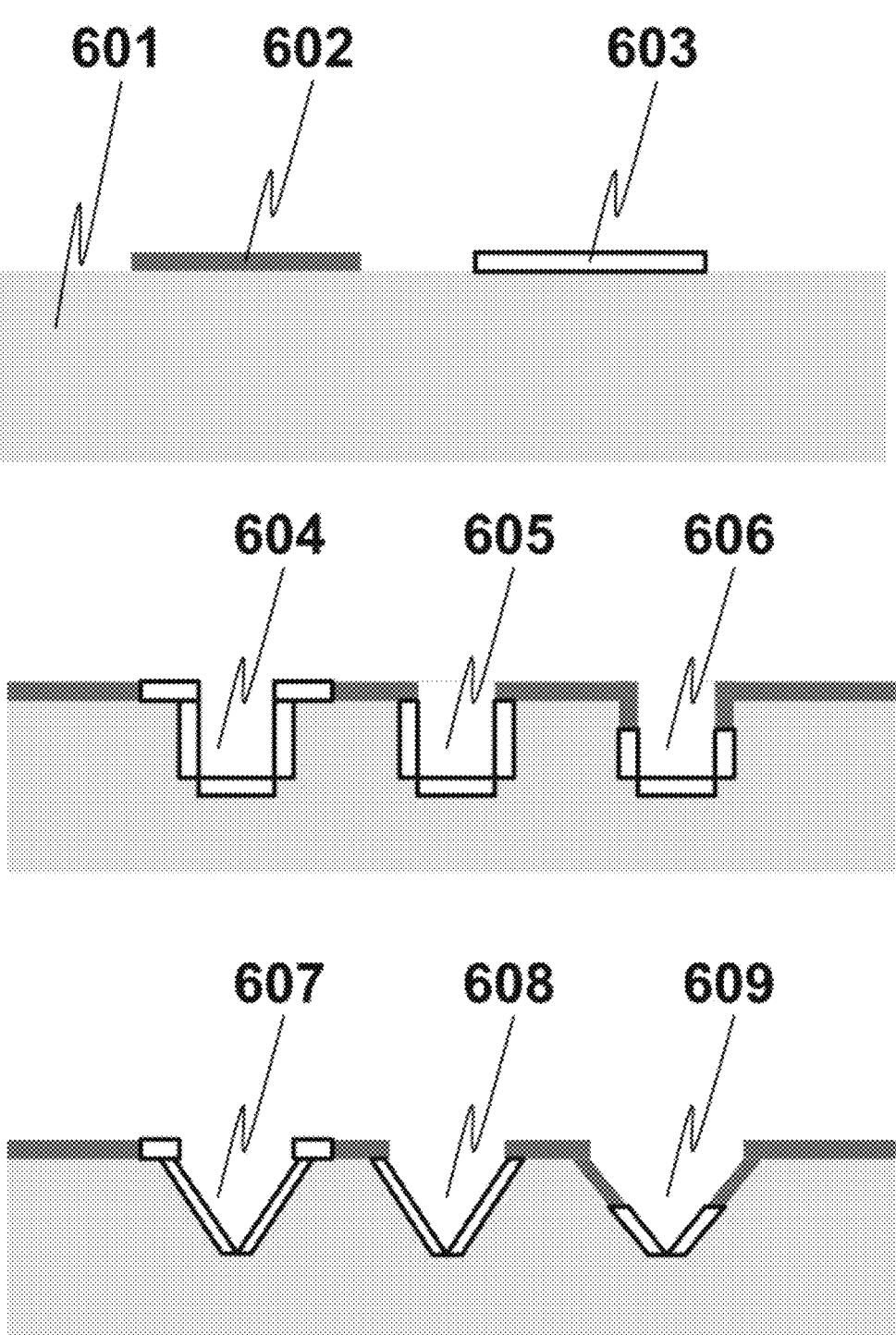
FIG. 6 demonstrates various cross-section of channels patterned on the surface of a fluidic device, that are at least partially, defined by hydrophobic and hydrophilic surfaces.

In order to promote the wicking, wetting, or maintaining of the nucleic acid into the channels such that they can be orderly positioned within, the top surface of the fluidic device can be made hydrophobic, except certain areas. For example, by contact transfer stamping of a hydrophobic molecule to the glass fluidic device surface via transfer stamping [Smith, 2004], and leaving the naturally hydrophilic channels defined on the fluidic device surface unmodified. A multitude of different hydrophilic patterns designs are possible. In the preferred embodiment, the solution can be contained within said pattern using a hydrophobic barrier on either side. Non limiting variations are shown in FIG. 6 in which the surface of a fluidic device (601) can be selectively patterned with a hydrophobic surface (602) or a hydrophilic surface (603). In some embodiments, the fluidic device surface is naturally hydrophobic, so that hydrophobic regions can be patterned by the absence of any hydrophilic patterning. Alternatively, in some embodiments, the fluidic device surface is naturally hydrophilic, so that hydrophilic regions can be patterned by the absence of any hydrophobic patterning. The patterns defined on the surface of the fluidic device may take on any geometric shape including channels, pits, holes, hills, mounts, troughs, pillars, or the like. In some embodiments, the cross-section of the patterns may be rectangular in shape (604, 605, 606). In the preferred embodiment, there exists a hydrophobic surface region between the channels, and there exists a hydrophilic region within the channels, as demonstrated with 604, 605, 606. In some embodiments, the patterned features may have a triangular cross-section (607, 608, 609), or oval cross-section. In some embodiments, the patterned region may consist only of surface energy features on the surface of the fluidic device.

In some embodiments, the channels are separated from adjacent and substantially parallel channels with a distance that can range from 0.2 to 100 microns. In some embodiments, the channels are patterned at fixed period. In some embodiments, the channels are patterned randomly. In some embodiments, the patterned features are at least partially comprising of pits or pillars. In some embodiments, the depth of the patterned features, or the height of the patterned features can range from 0 nm to 10 microns. (0 depth for embodiments where-by the channel is defined only by surface energy features.) In some embodiments, the patterned features are grouped in sets, in which they are physically co-located on the surface of the fluidic device. In some embodiments, the sets of features are defined to physically accommodate all of the long nucleic acid molecules that originate from at least one package. In some embodiments, the sets of features are defined to physically accommodate all of the long nucleic acid molecules that originate from only one package. In some embodiments, the sets are physically separated from each other sufficiently far that a single package cannot physically contact two adjacent sets. In some embodiments the physical distance between sets varies from 2 to 500 microns.

Receding Meniscus Generation of Long Nucleic Acid Spreads

In this sub-set of embodiments, the fluidic devices and methods are capable of generating spreads of large nucleic acid molecules on the surface of the device via the deposition of the molecules into an interrogation region, where-by the deposition process is via a receding meniscus over patterned features. The spread molecules are physically co-located with other molecules from the same package, and sufficiently separated from adjacent package's molecules to enable grouping identification via imaging. In some embodiments, imaging of the molecules is enabled by incorporating a transparent viewing material, typically glass or plastic, of sufficiently similar optical properties and thickness of a standard glass coverslip over the sample such that existing microscope systems with objectives designed for viewing traditional cytogenetic samples through glass coverslips can be employed. In some embodiments, the coverslip glass is integrated into the device, in other embodiments the coverslip glass can be added by the user in a process similar to standard cytogenetic protocols.

In some embodiments the receding meniscus is generated by a drop of solution that moves largely due to the force of gravity [Oshige, 2010]. In one embodiment, demonstrated in FIG. 7, the microfluidic device is comprising of a microfluidic device with patterned surface features (712), where in this example, the patterned surface features are comprised of patterned channels that are substantially exposed to the environment. The channels (708) are patterned on the surface such that the physical boundary walls within the channels are substantially hydrophilic. In such a manner, a receding meniscus of solution composed of bodies will deposit said bodies into the channels. The specificity of body deposition into the channels, and not between the channels, can be enhanced by including a hydrophobic surface on the regions between adjacent channels (711).

In one preferred embodiment for generating large nucleic acid molecule spreads the device is maintained at an angle (710), either manually or with the use of a jig, between 0 and 90 degrees, preferably between 20 and 70 degrees, more preferably between 30 and 60 degrees, and a sample dispensing tool (701) dispenses a sample solution (702) containing packages of long nucleic acid molecules (703). After the solution makes contact with the device, the solution (707) flows down the surface of the device via the force of gravity (709), resulting in the formation of a receding meniscus (705). In some embodiments the packages are already substantially ruptured via the collision force of dropping the solution onto the device. In other embodiments, the packages survive the collision largely un-ruptured, but then the packages (706) lyse upon deposition of the chromosomes into the channel by the receding meniscus, leaving a trail of nucleic acid molecules (704) in the channels. Prior art [Park, 2006] has demonstrated that receding meniscus of a solution containing cells on a patterned surface is an effective means of ordering the placement of said cells into the surface patterns.

In some embodiments the receding meniscus is generated by a drop of solution that moves largely due to a capillary force. A capillary force can be generated by fluidic structures in a microfluidic device that are designed to take advantage of the structure's surface energy features and physical features to promote the asymmetric wetting, such that a fluid will flow preferentially from one region to another (see definition section on surface energy). Generally, all other things being equal, a solution will more preferentially wet a smaller dimensioned confinement region over a larger dimensioned confinement region.

Figure 8:
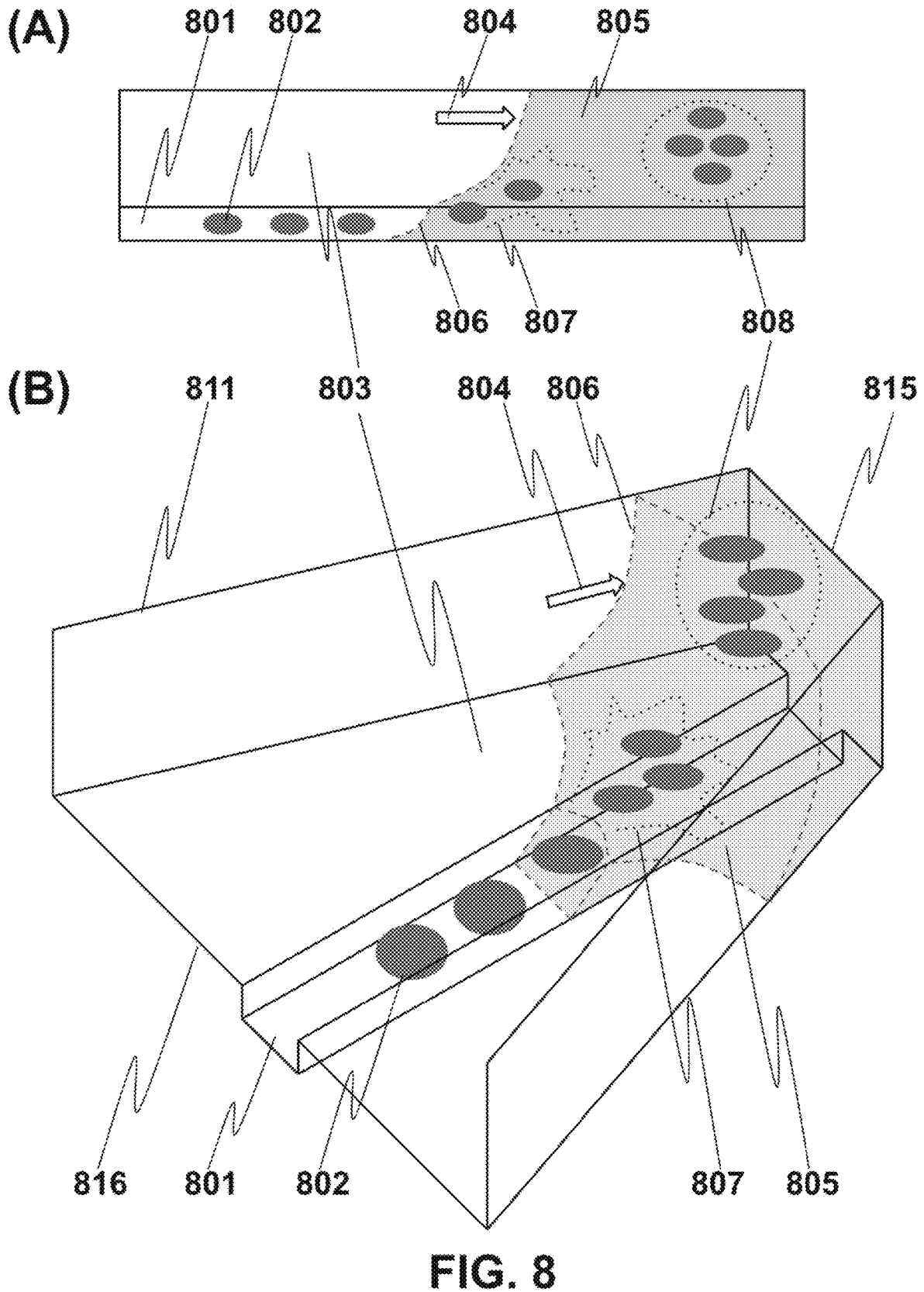
FIG. 8(A) illustrates a side view of a cytogenetic fluidic device used for generating chromosome spreads for genomic analysis, where-by a solution of packages containing nucleic acid molecules are deposited onto the patterned surface features of the device, via the receding meniscus of the solution.
FIG. 8(B) illustrates an isometric view of a cytogenetic fluidic device shown in FIG. 8(A), where-by the receding meniscus is generated via the combination of capillary force and evaporation of water from the solution.

Capillary forces can be used to implement a number of different embodiments. In one embodiment described in FIGS. 8(A) and 8(B), a containing channel (803) defined by channel walls (811) that are formed on a microfluidic device surface (816) patterned with features (801) on the surface, is designed such that fluid will flow due to capillary forces or micro-convection flow in substantially one direction (804) over the patterned features. In this particular embodiment, the patterned features on the surface of the device are channels. In one embodiment, the containing channels are designed such that an evaporation of the water from the solution (805) preferentially collects via surface tension the remaining solution in the region of highest wetting attraction in the containing channel via or micro-convection flow (815). This produces a receding meniscus (806) that moves (804) to the region of higher wetting attraction within the containing channel (815). In the example shown in FIG. 8, the region of higher wetting attraction is defined by a containing channel with monotonically reducing cross section, creating large surface area to volume ratio, such that the solution will preferentially wet the narrower section of the containing channel (815). This movement of solution from one end of the containing channel to the other results in a receding meniscus moving along the bottom of the channel in a controlled direction over the patterned features. The speed and direction of the meniscus movement can be tuned by the physical and dimensional properties of the narrowing channel (for example: surface energy, depth, angle of narrowing, height, to name a few), and environmental properties (for example: temperature, humidity, pressure, to name a few). In some embodiments, the containing channel depth can range from 1 micron to 1000 microns, or from 10 microns to 500 microns. In some embodiments, the width of the containing channel can vary from 1000 microns to 1 micron. In the preferred embodiment, the containing channel is in fluidic contact with a well region in which the sample solution is loaded into the device. In some embodiments, there are multiple containing channels connected to the well region.

In another device embodiment, the direction and speed of the receding meniscus over the patterned features is at least partially influenced by a capillary pump or microconvection force caused by local evaporation. In some embodiments, a capillary pump is in fluidic connection with the containing channel such that once wetted, the capillary pump will draw the solution out of the containing channel into the pump, and thus produce a receding meniscus over the patterned features in the containing channel.

In some device embodiments, the direction and speed of the receding meniscus over the patterned features is at least partially controlled by a combination of capillary, micro-convection force and gravitational forces, either constructively, or in opposition to each other.

The exact positioning of the patterned features within the confinement channel is not critical. In one preferred embodiment, the major axis of the patterned features is substantially parallel to the direction of the receding meniscus.

Capillary Flow Generation of Long Nucleic Acid Spreads

In another set of embodiments of the device, the large nucleic acid molecules are positioned within patterned features on the surface of the fluidic device via solution capillary flow in which the patterned features form at least a portion of the interrogation region, and form part of a fluidic channel network that act to contain the solution, while a capillary pump pulls the solution through said features. While being flowed through said features, the long nucleic acid molecules become arranged within the features. Once sufficiently arranged, the solution is evaporated, leaving the nucleic acid molecules on the surface in an arranged state, ready for subsequent cytogenetic processing and optical interrogation.

In some embodiments, the solution originates from at least a single well that is fluidically connected to the patterned features upon wetting of the well with input sample solution. In some embodiments, the patterned features are comprising at least a portion of the capillary pump. In some embodiments, the capillary pump is fluidically connected to the patterned features.

Figure 9:
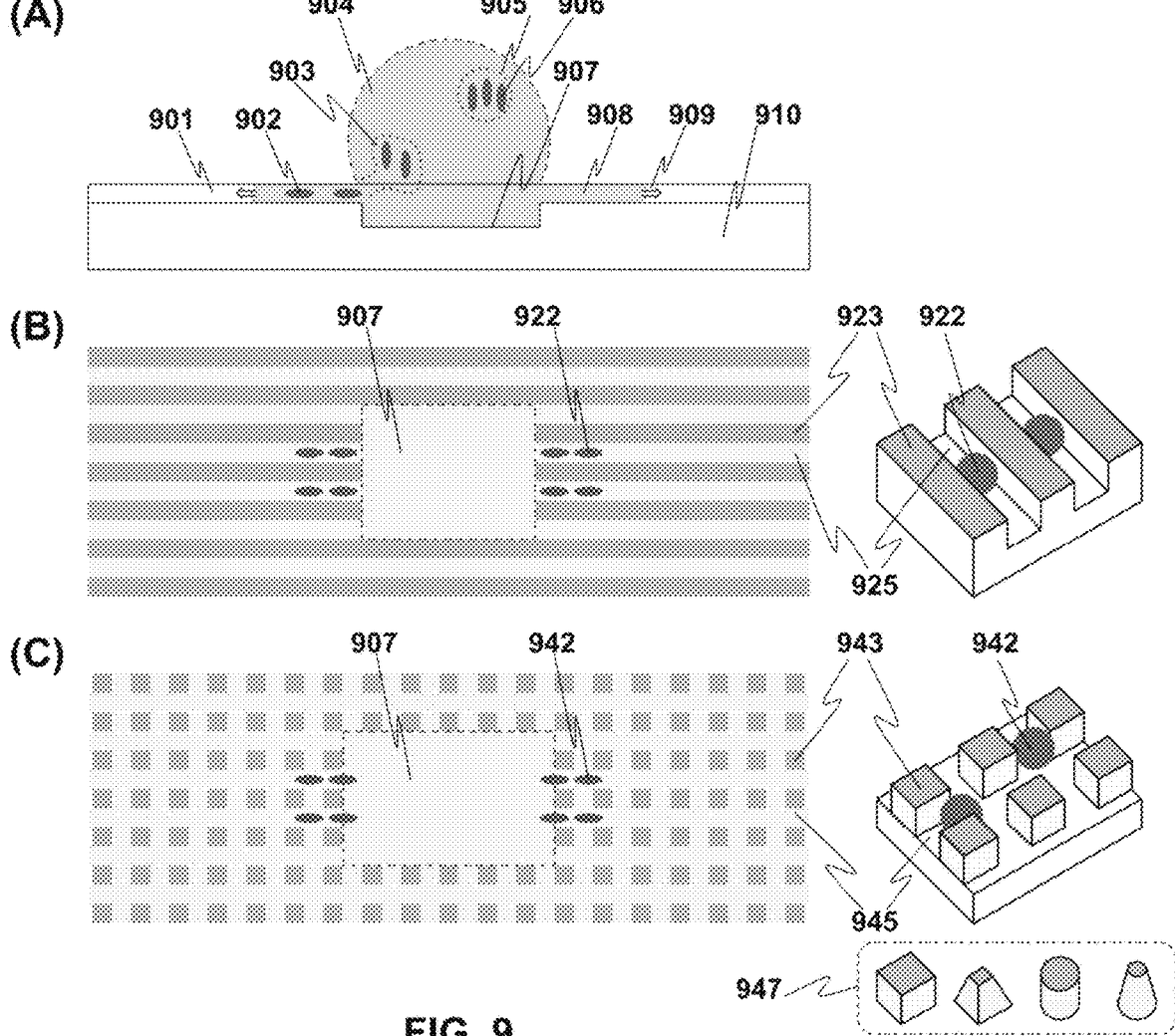
FIG. 9(A) illustrates a side view of a cytogenetic fluidic device used for generating chromosome spreads for genomic analysis, where-by the a solution of packages containing nucleic acid molecules are flowed into a collection of patterned features on the surface of the device via capillary force, and the solution originates from a central droplet largely contained by patterned surface features, where in this example, a well containing the solution is integrated on the surface of the device.
FIG. 9(B) illustrates a top and isometric view of one example type of the fluidic device shown in FIG. 9(A), where-by the patterned features include channels.
FIG. 9(C) illustrates a top and isometric view of one example type of the fluidic device shown in FIG. 9(A), where-by the patterned features include pillars.

One embodiment is demonstrated in FIG. 9(A). Here, an input sample solution (904) containing packages (905) of long nucleic acid molecules (906) is loaded onto a microfluidic device (910) that includes a patterned well (907) to contain the input solution. The patterned well is defined by physical features and surface energy features. The well is in fluidic connection with patterned features on the surface of the fluidic device (901), such that upon loading the input sample solution into the well, the solution (908) wets via capillary force (909) the connecting patterned features. The shear force of the capillary flow into fluidic features or coupled with a local physically sharp structure, ruptures the packages (903) allowing the long nucleic acid molecules to enter features in an ordered fashion (902).

FIG. 9(B) demonstrates a further refined embodiment of FIG. 9(A), here the patterned features on the surface of the fluidic device are largely parallel channels (925) in which the bottom region of the channel are largely hydrophilic, and the region between the channels is largely hydrophobic (923). The long nucleic acid molecules (922) are then flowed by capillary force into said channels, and deposited within the patterned features (925). In this embodiment, the bottom of the well (907) is physically lower than the interconnecting channels (925), and fluid confinement within the well is at least partially controlled by the hydrophobic regions between the channels (923).

FIG. 9(C) demonstrates another further refined embodiment of FIG. 9(A), here the patterned features on the surface of the fluidic device are largely interconnected channels (945) in which the bottom regions of the channels are largely hydrophilic. The network of interconnected channels is separated from each other by a collection of pillars (943) with largely hydrophobic tops. In this embodiment, the bottom of the well (907) is physically lower than the interconnecting channels (945), and fluid confinement within the well is at least partially controlled by the hydrophobic regions between the channels (943). After an input solution has been introduced into the well, the solution wets the connected interconnecting channels and deposits the long nucleic acid molecules (942) within the patterned features (945). The shape of the pillars that separate the adjacent channels can take on a variety of forms. Non-limiting examples (947) include rectangles, polygons, cylinders, and cones.

Figure 10:
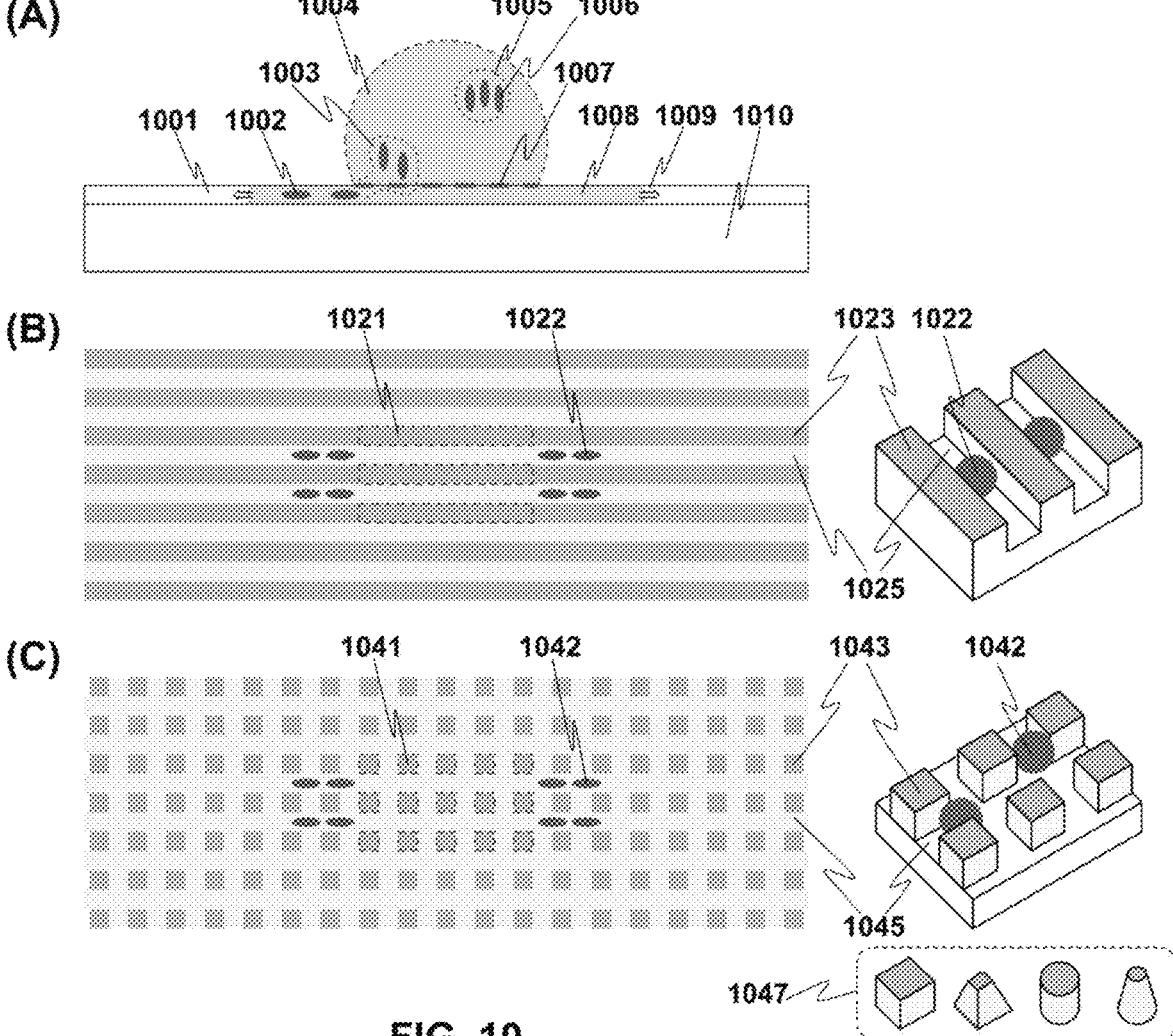
FIG. 10(A) illustrates a side view of a cytogenetic fluidic device used for generating chromosome spreads for genomic analysis, where-by a solution of packages containing nucleic acid molecules are flowed into a collection of patterned features on the surface of the device via capillary force, and the solution originates from a central drop largely contained by patterned surface energy features.
FIG. 10(B) illustrates a top and isometric view of one example type of the fluidic device shown in FIG. 10(A), where-by the patterned features include channels.
FIG. 10(C) illustrates a top and isometric view of one example type of the fluidic device shown in FIG. 10(A), where-by the patterned features include pillars.

An additional embodiment of this device is demonstrated in FIG. 10(A). Here, an input sample solution (1004) containing packages (1005) of long nucleic acid molecules (1006) is loaded onto a microfluidic device (1010) that includes a patterned well (1007) to contain the input solution. The patterned well is defined by surface energy features where-by there is a hydrophilic region that is surrounded by a hydrophobic region, and the hydrophilic region is in connection with patterned features on the surface of the fluidic device (1001), such that upon loading the input sample solution into the well, the solution (1008) wets via capillary force (1009) the connecting patterned features. The shear force of the capillary flow into fluidic features ruptures the packages (1003) allowing the long nucleic acid molecules to enter features in an ordered fashion (1002).

FIG. 10(B) demonstrates a further refined embodiment of FIG. 10(A), here the patterned features on the surface of the fluidic device are largely parallel channels (1025) in which the bottom regions of the channel are largely hydrophilic, and the region between the channels is largely hydrophobic (1023). The long nucleic acid molecules (1022) are then flowed by capillary force into said channels, and deposited within the patterned features (1025). In this embodiment, the bottom of the well interfaces with the interconnecting channels (1025), the regions between the channels are hydrophilic (1021) within the well region, and hydrophobic (1023) outside of the well region. Fluid confinement within the well is at least partially controlled by the hydrophobic regions between the channels (1023) outside of the well region.

FIG. 10(C) demonstrates another further refined embodiment of FIG. 10(A), here the patterned features on the surface of the fluidic device are largely interconnected channels (1045) in which the bottom regions of the channels are largely hydrophilic. The network of interconnected channels is separated from each other by a collection of pillars (1043) with largely hydrophobic tops. In this embodiment, the bottom of the well interfaces with the interconnecting channels (1045), the regions between the channels are hydrophilic (1041) within the well region, and hydrophobic (1043) outside of the well region. Fluid confinement within the well is at least partially controlled by the hydrophobic regions between the channels (1043) outside of the well region. After an input solution has been introduced into the well, the solution wets the connected interconnecting channels and deposits the long nucleic acid molecules (1042) within the patterned features (1045). The shape of the pillars that separate the adjacent channels can take on a variety of forms. Non-limiting examples (1047) include rectangles, polygons, cylinders, and cones.

Figure 11:
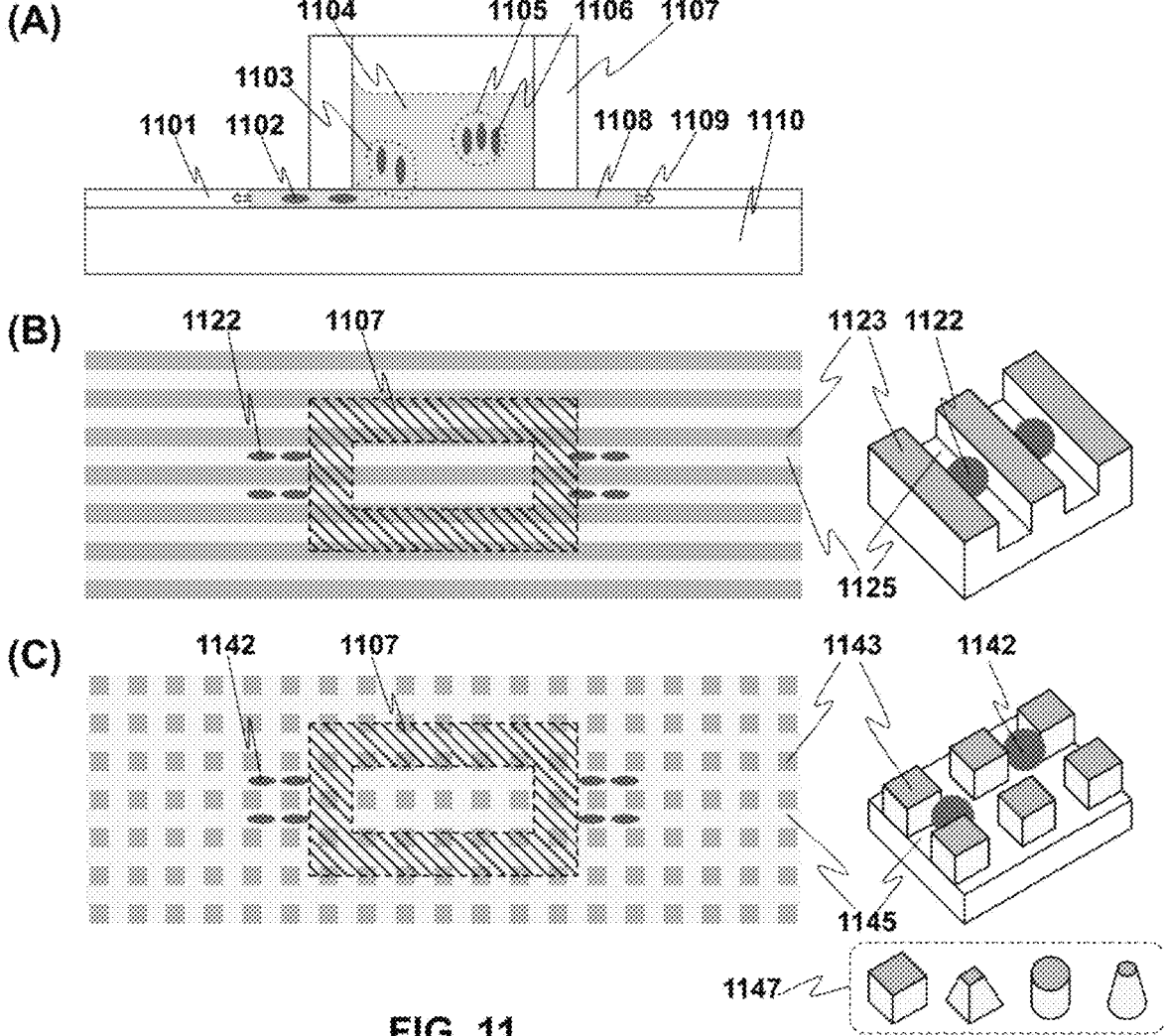
FIG. 11(A) illustrates a side view of a cytogenetic fluidic device used for generating chromosome spreads for genomic analysis, where-by a solution of packages containing nucleic acid molecules are flowed into a collection of patterned features on the surface of the device via capillary force, and the solution originates from a central droplet largely contained by a well.
FIG. 11(B) illustrates a top and isometric view of one example type of the fluidic device shown in FIG. 11(A), where-by the patterned features include channels.
FIG. 11(C) illustrates a top and isometric view of one example type of the fluidic device shown in FIG. 11(A), where-by the patterned features include pillars.

An additional embodiment of this device is demonstrated in FIG. 11(A). Here, an input sample solution (1104) containing packages (1105) of long nucleic acid molecules (1106) is loaded onto a microfluidic device (1110) that includes an integrated well (1107) that contains the input solution and interfaces to the patterned features. The integrated well is defined by physical boundaries. The well is in fluidic connection with patterned features on the surface of the fluidic device (1101), such that upon loading the input sample solution into the well, the solution (1108) wets via capillary force (1109) the connecting patterned features (1101). The shear force of the capillary flow into fluidic features ruptures the packages (1103) allowing the long nucleic acid molecules to enter features in an ordered fashion (1102).

FIG. 11(B) demonstrates an example refined embodiment of FIG. 11(A), here the patterned features on the surface of the fluidic device are largely parallel channels (1125) in which the bottom regions of the channel are largely hydrophilic, and the region between the channels is largely hydrophobic (1123). The long nucleic acid molecules (1122) are then flowed by capillary force into said channels, and deposited within the channels (1125). In this embodiment, the bottom of the integrated well (1107) is in fluidic contact with the interconnecting channels (1125), and fluid confinement within the well is controlled by the well's physical boundaries.

FIG. 11(C) demonstrates another example refined embodiment of FIG. 11(A), here the patterned features on the surface of the fluidic device are largely interconnected channels (1145) in which the bottom regions of the channels are largely hydrophilic. The network of interconnected channels is separated from each other by a collection of pillars (1143) with largely hydrophobic tops. In this embodiment, the bottom of the integrated well (1107) is in fluidic contact with the interconnecting channels (1145), and fluid confinement within the well is controlled by the well's physical boundaries. After an input solution has been introduced into the well, the solution wets the connected interconnecting channels and deposits the long nucleic acid molecules (1142) within the channels (1145). The shape of the pillars that separate the adjacent channels can take on a variety of forms. Non-limiting examples (1147) include rectangles, polygons, cylinders, and cones.

In some embodiments, the integrated well can be separated from the fluidic device by the user after flowing the input sample. Removal of the well may allow for improved integration of the device with existing cytogenetic systems designed to accommodate such slides of fixed geometry. In addition, removal of the integrated well may improve access to the nucleic acid molecules in the patterned features to various reagents, for example karyotyping or FISH protocols. Finally, removal of the integrated well may allow for improved application of a coverslip by the user over the long nucleic acid molecules.

In some embodiments, the integrated well can be attached to the device prior to application of the input sample to the device by the user.

In some embodiments the fluidic interface from the sample inlet well to the patterned features comprising the interrogation region may include additional patterned features to aid the process of loading and elongating the long nucleic acid molecules into the interrogation region. In one embodiment, the interrogation region is composed of channels of triangular shape with wider opening at the top and tapered towards the infinitive narrower bottom, the capillary force favoring the smaller bottom to generate a capillary flow differential creating a downward drag as well as forward flow along the longitudinal narrow seam line of the channel, promoting the alignment and elongation of the chromosomal and DNA molecules along their long axis.

Long Nucleic Acid Spreads Via Physical Confinement within a Microfluidic Device

In this set of embodiments, packages of long nucleic acid molecules are ruptured within an enclosed interrogation region of the microfluidic device via an increased pressure differential between the inside of the package and the solution outside of the package, while the package is maintained within an interrogation region that confines the packages. In certain embodiments, the pressure differential is generated by a reagent exchange such that cells become hypotonic. In certain embodiments, the pressure differential is generated by modifying the physical boundaries of the region of the fluidic device in which the package is contained. In certain embodiments, a combination of both reagent exchange and physical boundary modification are used.

In some embodiments, at least one boundary wall of the confinement region has substantially similar optical properties as a standard microscope coverslip. In one preferred embodiment, the boundary wall is approximately 170 microns thick, and has an optical index of refraction of approximately 1.52. In one preferred embodiment, the boundary wall is composed of borofloat glass.

After the packages have been ruptured in the device, in certain embodiments the package contents of long nucleic acid molecules can be prepared for interrogation by fluid exchange of reagents in the channels. In other embodiments, at least one physical channel wall of the microfluidic device that contains the long nucleic acid molecule can be removed such that the long nucleic acid molecules are now contained within an exposed surface microfluidic device, thus facilitating regent exchange.

Figure 12:
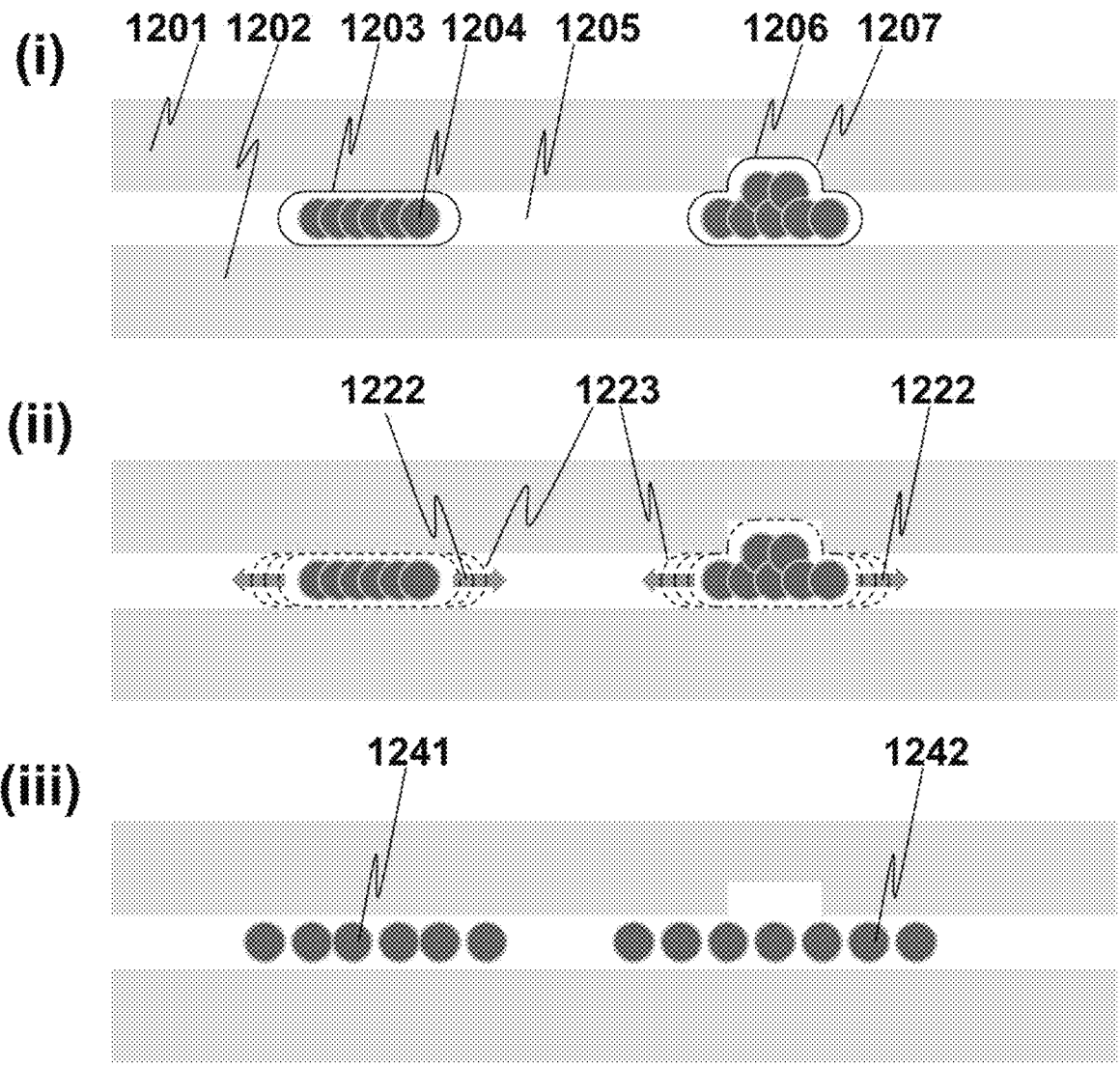
FIG. 12 illustrates a fluidic device where-by packages containing nucleic acid molecules are confined between two parallel substrates, where-by the i) the packages are confined, ii) the packages expand in the unconfined dimension due to pressure, and iii) the package contents are released.

In one particular embodiment shown in FIG. 12 packages (1203, 1206) of long nucleic acid molecules (1204) are loaded into an enclosed channel serving as an interrogation region (1205) of a fluidic device (1202) such that the packages are physically confined along at least one dimension and thus may be considered "squished". In some embodiments, there is no preferential location along the channel in which the package (1203) may occupy. In other embodiments, the fluidic device has at least one pit (1207) that serves as an entropic trap to preferentially localize the package (1206) at the location of the pit.

In this particular embodiment, a hypotonic solution is then introduced (ii) into the interrogation region such that the packages swell (1223) from the pressure differential (1222), and ultimately rupture (iii), releasing the long nucleic acid molecules (1241, 1242). The height of the interrogation region confines the molecules along at least one dimension, preventing the molecules from overlapping vertically on one-another in an energetically unfavorable state. With the nucleic acid molecules now spread within the device, additional reagents and solvents can then sequentially added into the interrogation region in the desired manner of sequence and timing. In certain embodiments, the introduction of reagents into the interrogation region is assisted via capillary force. In some embodiments the capillary force is at least partially provided by a capillary pump. In some other embodiments the capillary force is at least partially maintained and provided by a local micro-convection flow caused by temperature, osmotic or surface energy gradient or evaporation force. In some embodiments, the exchange of reagents is performed by diffusion of reagents into the interrogation region.

In some embodiments the rupture of the packages in the microfluidic device is at least partially assisted by reducing the confinement region in which the package is held.

Figure 13:
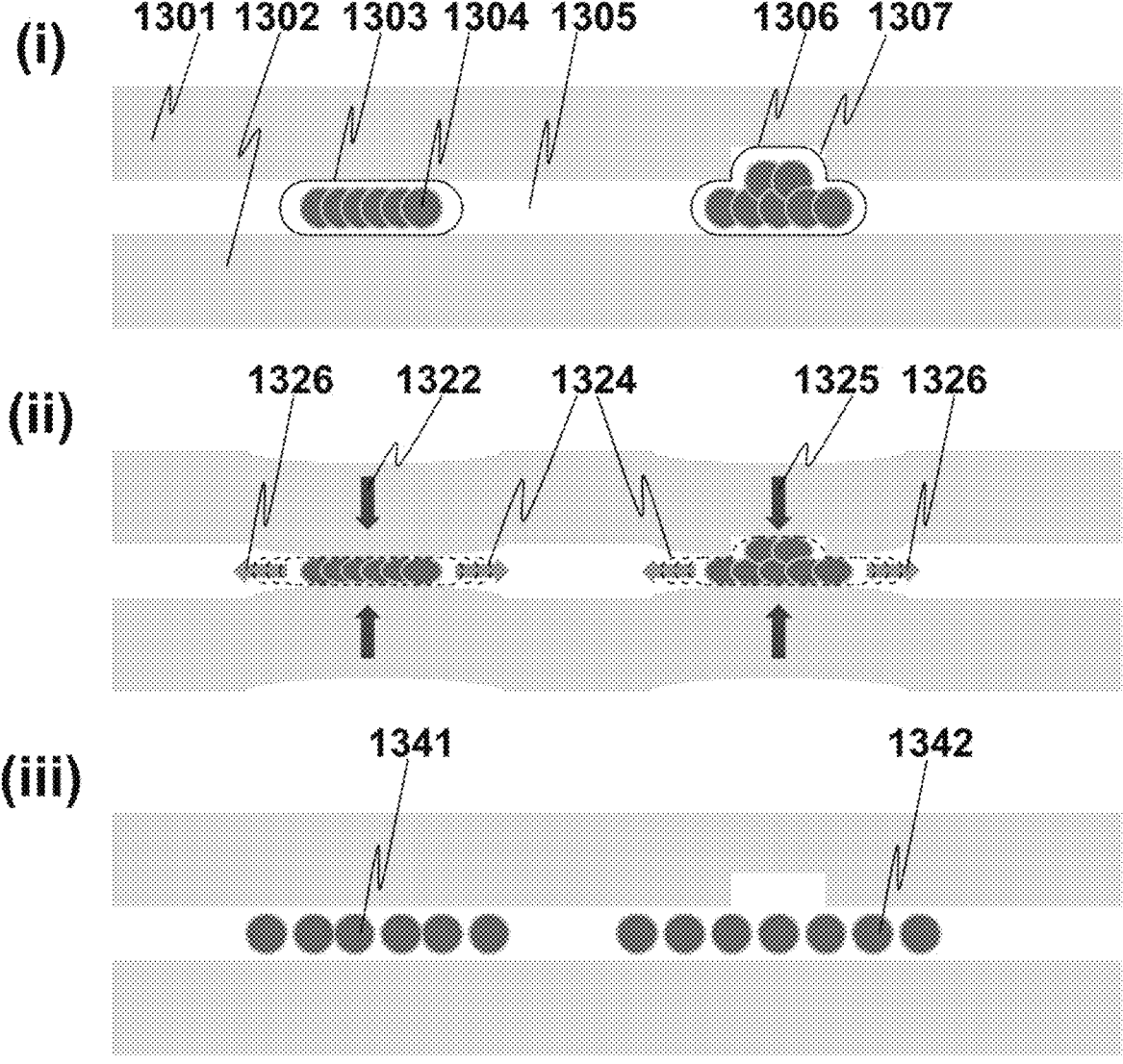
FIG. 13 illustrates a fluidic device where-by packages containing nucleic acid molecules are confined between two parallel boundaries, where-by the i) the packages are confined, ii) the packages expand in the unconfined dimension due to pressure, and iii) the package contents are released.

In one particular embodiment shown in FIG. 13 packages (1303, 1306) of long nucleic acid molecules (1304) are loaded into an enclosed channel serving as an interrogation region (1305) of a device (1302) such that the packages are physically confined along at least one dimension and thus may be considered "squished". In some embodiments, there is no preferential location along the channel in which the package may occupy (1303). In other embodiments, the fluidic device has at least one pit (1307) that serves as an entropic trap to preferentially localize the package (1306) at the location of the pit.

In this particular embodiment, the confinement region in which the packages are occupying undergoes an increase in confinement (1322, 1325) in at least one dimension (a decrease in the confining dimension) such that the pressure in the packages increases relative to the solution external to the packages (ii). The increase in confinement is due to a compressive force applied on the boundaries of the microfluidic channel within the device (1322, 1325), for example by pressing down on the device with a probe, or applying pressure with a press. For methods where-by the force is locally applied, the location of the applied force applied can be coordinated with the location of the pits 1307. The compressive force results in the packages to swelling (1324) in the non-confining dimension from a pressure differential (1323, 1326), rupturing, releasing the long nucleic acid molecules (iii). In some embodiments, this process is done with the packages in a hypotonic state. The height of the interrogation region confines the molecules along at least one dimension, preventing them from overlapping vertically on one-another (1341, 1342) in an energetically unfavorable state. With the nucleic acid molecules now spread within the device, additional reagents and solvents can then sequentially added into the interrogation region in the desired manner of sequence and timing. In certain embodiments, the introduction of reagents into the interrogation region is assisted via capillary force. In some embodiments the capillary force is at least partially provided by a capillary pump. In some embodiments, the in the exchange of reagents is performed by diffusion of reagents into the interrogation region.

In the preferred embodiment, the depth of the channel (1305, 1205) is the confining dimension (or one of the confining dimensions), such that the unconfined dimension(s) in which the package can expands in response to the confinement is substantially parallel to a plane that is substantially normal to the optical axis of inspection. In the preferred embodiment, the depth of the channel is appropriately defined for the package dimensions, such that the channel depth is approximately the diameter of the package or less, or more preferably approximately 75% of the diameter or less. The diameter can range considerably depending on the type of package used. For example, a blood cell may be 5-15 microns, while a water-oil-water droplet may be as large as several 100 microns. Similarly, in the preferred embodiment, the size of the pit (1207, 1307) should be appropriately sized to capture a single package, more preferably only a single package. Thus, preferably, the pit volume should be less than 200% the volume of a package, or more preferably less than 150% the volume of the package.

In some embodiment devices, a capillary retention valve (CRV) and a capillary pump [Juncker, 2002] are incorporated into the device to allow for multiple, and controlled, introduction of solutions and reagents into the interrogation region. By integrating such a CRV and pump into the device, multiple sequential dispensing of different reagent solutions and rinses can be added to the inlet, thus exposing the long nucleic acid molecules to said reagents for desired intervals of time.

In some device embodiments, various physical obstacles can be included in the interrogation region. These physical obstacles limit the mobility of the packages and long nucleic acid molecules, and can be used to physically maintain the packages or long nucleic acid molecules within the interrogation region during fluid flows.

In some device embodiments where-by reagent and solution exchange is at least partially facilitated by diffusion into and out of the interrogation region, the interrogation region is physically positioned within the device such that it is in fluidic connection with a large reservoir well such that the fluidic contents of the reservoir well can be efficiently exchanged via submerging the reservoir well in the desired solution, and allowing diffusion to exchange solutions between the interrogation region and the reservoir well. Typically diffusion limited solution exchanges processes are extremely slow in microfluidic device environments. In one embodiment device, the diffusion process is expedited by designing the device such that parts of the interrogation region are within 1000 microns of the reservoir well, or preferably within 500 microns of the reservoir well, or even more preferably within 250 microns of the reservoir well.

In some device embodiments, at least one boundary wall comprising the interrogation region is itself part of a deformable or removable lid. In some embodiments, the lid can be removed by user using a tab which is incorporated into the lid.

Active Microfluidic Device for Cytogenetic Analysis

In this set of embodiments, we disclose devices and methods for a fluidic device consumable that enables the positioning of nucleic acid material for interrogation in a manner that improves the data quality via the controlled physical arrangement of the long nucleic acid molecules within the interrogation region of the device in an active fashion, such that the fluidic device is operated by a control instrument.

Some fluidic device and method embodiments described herein are designed for the generation of large nucleic acid molecule spreads in such a manner that the large nucleic acid molecules originating from a single package are co-located and substantially non-overlapping within the interrogation region of the fluidic device, providing higher yields and improved data quality over a standard microscope slide using common chromosome preparation methods in which the chromosomes are positioned randomly on the surface of a microscope slide. Some device and design embodiments are designed to physically manipulate the physical conformation of a macromolecule via interaction of reagents such as enzymes or physical interaction with patterned features, allowing for improved resolution of distinct features within the macromolecule. Some device and method embodiments described herein are designed for the generation of elongated long nucleic acid fragments within elongation channels of the microfluidic device, providing reduced variability in stretch and molecule overlapping compared to common fiber-FISH and DNA-combing protocols.

After loading the device with an input solution containing suspended packages of macromolecules, the packages are individually captured at various capture sites, designed to accommodate only a single package [Wheeler, 2003], [Lee, 2006], [Voldman, 2008, U.S. Pat. No. 9,201,060], [Le Gac, 2009], [Chung, 2001]. Once captured, the package in its entirety, or the long nucleic acid molecule contents there-in, are fluidically flowed into a reaction chamber. Excluding the fluidic connection from a capture site, the reaction chamber is designed such all-other fluidic connections are through an entropic barrier. In some embodiments the fluidic connection to the capture site may also have an entropic barrier, thus the reaction chamber becomes an entropic trap. In some embodiments, there can be a single reaction chamber associated with a single capture site. In some embodiments, a reaction chamber may accommodate multiple capture sites. In some embodiments the package is lysed or ruptured in the capture site. In some embodiments, the package can be lysed or ruptured in the reaction chamber.

The reaction chamber is fluidically connected to at least one fluidic channel via an entropic barrier, such that there exists a minimal external force that allows for fluid exchange within the chamber, through the connecting channel, but insufficiently large that the macromolecule can overcome said barrier. With such a device, the macromolecule(s) will remain contained within the reaction chamber while being exposed to a series of solution exchanges of desired composition, time, pressure, and temperature. In some embodiments, the macromolecules are entire human chromosomes, and the reactions prepare said molecules for FISH or physical mapping interrogation within the interrogation region of the device. In some device embodiment configurations, the reaction chamber and the interrogation region are the same. In other device embodiment configurations, these are fluidically connected, but separate chambers.

The entropic barriers of the reaction chamber are designed to physically contain the large macromolecules, however smaller molecules, for example those contained within the package, and released upon lysing of the package, will easily pass through said barriers. As a consequence, this provides an opportunity to collect the smaller molecules for additional down-stream analysis. In some embodiments, the molecules collected include proteins, enzymes, RNA, mRNA, sRNA, tRNA, snRNA, nucleic acid molecules, nucleic acid barcodes, antibodies, viruses.

In one preferred embodiment of the device, the input sample solution and any associated reagent solutions required to operate the device, can be loaded via manual pipette dispensing or automated liquid handling systems. In one preferred embodiment of the microfluidic device, the operation of the device may be controlled by at least one control instrument, which in turn, may be controlled by a program or a person(s). Operation of the device by the control instrument can include manipulating the physical position and conformation of the package or macromolecule via the application of external forces on said bodies, exposing the package or macromolecule to various reagent compositions and concentrations for various time periods and temperatures, optically interrogating the package or macromolecule to facilitate analysis of its composition or as part of a feedback system to control the operation of the device, or extracting desired macromolecules or portions of macromolecules from the device. The microfluidic device and control instrument can interface in a number of ways. A non-exhaustive list includes: fluidic ports (both open and sealed), electrical terminals, optical windows, mechanical pads, heat pipes or sinks, inductance coils. A non-exhaustive list of potential functions the control instrument may perform on the device include: temperature monitoring, applying heat, removing heat, applying pressure or vacuum to ports, measuring vacuum, measuring pressure, applying a voltage, measuring a voltage, applying a current, measuring a current, applying electrical power, measuring electrical power, exposing the device to focused and/or unfocused light, collecting the light generated or reflected from the device.

In one embodiment, confirmation of the presence of the macromolecule and control over its physical position within the device is controlled by the control instrument using a feedback controller system. Detection of the macromolecule is via detection of a at least one optical or electronic signal. In the preferred embodiment, the signal is an optical signal originating from a labelling body bound to said macromolecule.

In one embodiment, the control instrument feedback control system at least in part utilizes the identification of certain regions of interest within the molecule, or absence of certain regions of interest within the molecule. Various regions of interest may be associated with phenotypes, diseases, originating cell type, physical map pattern.

The control instrument may be centrally located, or have different parts distributed for different or redundant functions.

In order to run the operation software on the control instrument, and perform analysis for feedback control or interrogation data collection, a non-exhaustive list of potential options include: localized processing within the control instrument, adjacent processing via a direct communication connection, external processing via a network connection, or combination there-of. Various examples of processing modules include: a PC, a micro-controller, an application specific integrated micro-chip (ASIC), a field-programmable gate array (FPGA), a CPU, a GPU, a network server, cloud computing service, or combinations there-of.

The control instrument may include an imaging system, which may include any of the following types of imaging, or combinations there-of: fluorescent, epi-florescent, total internal reflection fluorescence, dark field, bright field, confocal.

The control instrument may be able to fire multiple light sources simultaneously, or in series, and be able to image multiple colors simultaneously, or in series. If imaging multiple colors simultaneously, this may be done on different cameras, on a single camera but different regions of the sensor array, or on the same sensor of the same camera. In some embodiments, the wavelength of light fired by the control instrument is chosen so as to interact with the sample, the sample labeling body, or a functionalized surface in some way. Non limiting examples include: photo-cleaving of the nucleic acid, photo-cleaving photo-cleavable linkers, manipulating optical tweezers, activating photo-activated reactions.

The control instrument may have at least one photosensitive sensor, of which non-limiting examples include: CMOS camera, SCMOS camera, CCD camera, photomultiplier tube (PMT), Time Delay & Integration (TDI) sensor, photodiode, light dependent resistor, photoconductive cell, photo-junction device, photo-voltaic cell.

The control instrument may have at least on xy-stage, allowing for the imaging system to image different regions of the device, or other devices in the control instrument.

The control instrument may have 1 or more motors capable of adjusting the device's interrogation region relative the control instrument's optical path, including z, tip, and tilt, based on an auto-focus feedback system, software analysis of image quality, device accessibility requirements, user access, or combination there-of.

The control instrument may capable of robotic transport of one or more devices to different parts of the control instrument.

In some embodiments the microfluidic device can include fiducial markers or alignment markers that can be used to enable visual alignment of the device either manually or with the control instrument's program. In some embodiments, there are multiple zones on the fluidic device, with each zone designed to physically isolate different input samples. In some embodiments, there are fiducial markers on the device that guide the user or automated dispensing system where on the device to dispense solution.

Once the input sample solution is dispensed into or on the device, external forces on the package or macromolecule under the control of the control instrument, enable the consistent positioning of package's large nucleic acid molecules in the interrogation region of the device such that the probability of said molecules overlapping or self-folding is reduced when compared to a standard slide preparation. Furthermore, under control of the control instrument, while within the fluidic device, the macromolecule is exposed to a series of reagent compositions and concentrations for desired time periods and temperatures to prepare the macromolecules for interrogation. The spreads of large nucleic acid molecules are physically co-located with other molecules from the same package, and sufficiently separated from an adjacent package's molecules to enable grouping identification via imaging.

In one preferred embodiment, the package is a cell in a hypotonic state, and the large nucleic acid molecules are chromosomes in metaphase. In addition to metaphase chromosomes, chromosomes of different phases are also possible. For example, deposition of interphase chromosomes for use with FISH applications. Furthermore, the nucleic acid being deposited may be a portion of a chromosome, or nucleic acid originating from a source other than chromosomes such as mitochondria DNA. The nucleic acid may still be chromatin form. The nucleic acid may be a long nucleic fragment, thus enabling fiber-FISH applications. Much like DNA-combing methods, long nucleic fragments will be elongated onto a surface to enable cytogenetic applications. However here, due to the manipulation of the long nucleic acid molecule in the device by the control instrument, the long nucleic acid fragments will be elongated in a controlled manner rather than a purely random process. In addition, unlike combing that requires dipping a slide into a pool of sample, here the acquired interrogation data can be generated from the nucleic acid of a single package.

In one embodiment, the optical resolution of the physical map or FISH probes on the macromolecule is improved by physically expanding and/or elongating the macromolecule within at least one plane that is substantially normal to the optical axis used for interrogation. In some embodiments, this expansion is at least partially achieved via a timed exposure of the molecule to reagents (for example: enzyme that digest proteins and/or the nucleic acid) of controlled concentration, thus partially or fully releasing the nucleic acid strands from the chromatin structure. In some embodiments, this is at least partially achieved via the application of an external force on the macromolecule in the presence of physical obstacles, a porous medium, gel, or localized entropic traps within the reaction chamber that provide a retarding force, such that the largely counter-opposing retarding force and external force on the macromolecule act to elongate it. In some embodiments, the retarding force is a second external force. In some embodiments, this is at least partially achieved by introducing the macromolecule to a fluidic environment within the device that increases the molecule's physical confinement within at least one dimension, causing the macromolecule to physically expand within non-confining dimension(s). In some embodiments, the molecule is transferred into a region of greater physical confinement. In other embodiments the fluidic environment in which the molecule occupies can be adjusted to become more confining to the molecule, for example with a channel wall that can be modulated by applying pressure or a vacuum to a neighboring channel that interface via a flexible wall [Unger, 1999, U.S. Pat. No. 6,899,137], or with a flexible roof that encloses the channel [Yao, 2015, 2019/0217295], or a flexible roof with an external force [Leslie, 2017, 2020/0240898], [Mahshid, 2015], [Cohen, 2011, U.S. Pat. No. 10,048,193], or having a flexible channel walls comprising of, or are adjacent to, phase-change materials that can alter their shape to some stimulus [Hilber, 2016], or having channel walls attracted to each other via electrostatic attraction via the application of an alternating electric field [Sounart, 2005], [Sounart, 2010]. In some embodiments, the macromolecule experiences a compressive force with the application of a dielectrophoretic (DEP) force [Mashid, 2018, U.S. Pat. No. 10,307,769]. In some embodiments, a combination of any or all of these embodiment devices and methods are used to physically expand the macromolecule, with any or all of these embodiment device methods under control of the control instrument, preferably using a feedback control system. In some embodiments, a physical mapping labelling method is used that allows for both the generation of karyotyping bands, and the generation of a linear physical map along the length of a nucleic acid molecule. In this way, traditional karyotyping bands within the macromolecule can be obtained, and then through manipulation of said macromolecule via reagent exposures and/or physical confinement, portions of long nucleic acid molecules originating from the macromolecule can be elongated, interrogated, and compared to a reference. In some embodiments, the elongated portions of long nucleic acid molecules remain connected to the originating macromolecule during interrogation. In some embodiments, the portions are cleaved from the originating macromolecule. In the preferred embodiment, the origination position within the macromolecule from which the elongated portion of long nucleic acid molecule originates from is monitored and recorded by the control instrument. In some embodiments, the originating position is selected, in preferred embodiments selected due to an analysis of a physical map on the originating macromolecule. In some embodiments, the originating package or macromolecule is manipulated by an electrowetting device integrated in the device. Manipulation can include physical movement of molecule, introduction of reagents or rinse solvents, physical separation of macromolecules, physical co-localization of macromolecules.

The reagent materials and solutions that may be used include any that may be commonly be used by someone trained in the art of performing cytogenetic analysis on chromosomes. These reagents include various stains, fixatives, dyes, and solvents. Additional reagents may include various dyes specifically for physical mapping, linear physically mapping, FISH-probes, labelling bodies, methylation dyes, non-methylation dyes. In some embodiments, the flow of various reagents may be in one direction. In other embodiments, the fluid flow may alternate. In some embodiments, there may be mixture of external forces, for example a pressure driven reagent flow and an applied electrical field to manipulate the charged long nucleic acid molecule.

In some embodiments devices and methods, it is desired to interrogate the macromolecule with labeled bodies bound to it that provide a signal similar to or equivalent to a karyotyping banding profile. In some embodiments, the banding profile is generated by exposing the macromolecules to various reagent compositions and concentrations, for various temperature and time periods. In some embodiments, reagent compositions can be chosen to produce banding patterns well recognized by those in the cytogenetics industry, including R band, Q bands, C bands, and G bands. To improve signal contrast, some embodiments will also include a counterstain. For a review of commonly used cytogenetic karyotyping dyes and bandings please refer to [Moore, 2001]. In addition to the traditional karyotyping dyes, in some embodiment devices and methods, it is desirable to generate banding patterns that are compatible with elongated single molecule mapping applications, such as the previously mentioned physical mapping methods, in particular the linear physical mapping methods. Furthermore, in some embodiments, the process of generating the bands can be controlled by the control instrument, using a feedback control system to monitor the process, and optimize the banding contrast for the desired application.

In some embodiments, the surface of at least one of the boundary walls of the fluidic device that constitutes the interrogation region are modified to change the surface energy or add functionalization to promote nucleic acid molecule immobilization with the said surface. In some embodiments, a specific region of functionalization on the device surface is designed to immobilize a specific target of macromolecule. In some embodiments, the specific target is a type of chromosome.

For all embodiments "prepare for interrogation" refers to the process of physically, chemically, or enzymatically manipulating the long nucleic acid molecule's conformation or structure and/or the bonding of labeling bodies to the molecule to enable interrogation of said molecule via a series of different reagent solution exposures of desired concentrations, times, and temperatures, via any of the device and method embodiments previously discussed. In the preferred embodiment, the labeling bodies on the long nucleic acid molecule are comprising a physical map and/or FISH probes. In some embodiments, some of these preparations are performed beforehand, and thus "prepare for interrogation" in this context refers to the final steps necessary to enable interrogation of the molecules, as some steps have already been completed. For example, the package captured in the capture site may be a droplet, in which the contents of the droplet is a single cell that previously underwent processing inside the droplet, including: lysing, enzymatic digestion of proteins, and nucleic acid labeling of fluorescent labelling bodies to enable physical mapping. In some embodiments, at least some of the processes that define "prepare for interrogation" are done during interrogation, in some embodiments, as part of a feedback system. For example, it may be determined during interrogation that additional elongation is required, or a different physical conformation is desired, or the labeling bodies on the macromolecule needs to be modified in some way (for example, add a new label of a different fluorescent color), or combinations there-of.

Described within are a multitude of different active device embodiments. However, most embodiments share some basic functionality. First, an input sample comprising of suspended packages is introduced into the device. Second, packages are individually captured at capture sites. Third, the package contents consisting of long nucleic acid molecules are introduced into a reaction chamber. Forth, the long nucleic acid molecules are "prepared for interrogation" via physical positioning of, and the bonding of labeling bodies to, said molecules. Fifth, the control instrument optically interrogates said molecules while in the interrogation region of the device. In some device embodiments the reaction chamber and interrogation region are the same. In some embodiments, the interrogation region may also include an elongation channel. In some embodiments, the elongation and interrogation chamber are separated, although interrogation of the nucleic acid molecule within the elongation channel may still occur, depending on the embodiment. In some embodiments, the "preparation for interrogation" may have been at least partially performed before entering the reaction channel. In some embodiments, the "preparation for interrogation" may have been at least partially performed outside of the device prior to loading into the device.

The following embodiments represent various aspects of the invention and are not a complete list of all possible embodiments. In particular, the following embodiments describe specific features of the device and methods of use. Embodiments thus also include all feasible combinations and permutations of the various features the following embodiments. In addition, unless stated explicitly otherwise, in the embodiments given, the reaction chamber and interrogation chamber are the same fluidic component within the fluidic device. However, in certain embodiments, these may be different components within the device. In addition, the elongation channel is physically separate device region from the interrogation region, however under certain circumstances, at least a portion of the long nucleic acid molecule can also be interrogated within the elongation channel.

For all the device and method embodiments described, unless stated explicitly in the text, the dimension of the various features will depend upon what physical body the feature is intended to interact with, and the method of interaction. For example, a capture site should be suitably sized to capture at least one, preferably only one, package, and thus should preferably be sized approximately 175% of the package volume or less, or more preferably 150% of the package volume or less. The package size may vary from a human blood cell of 2-10 microns in diameter, to a water-oil-water droplet that can be as large as 500 microns. Similarly, a device embodiment with a entropic barrier preferably should have a confining dimension sized 95% of the package diameter or less, or more preferably 75% of the package diameter or less.

Note, the following terminology will be used to describe various physical components of the device embodiments:

fluidic connection points (defined in embodiments)
    sample loading channel (defined in embodiments)
    capture site (defined in embodiments)
    laminar flow port (defined in embodiments)
    narrowing connection (defined in embodiments)
    reaction chamber (defined in embodiments)
    interrogation region (defined in definitions)
    entropic barrier, entropic trap (defined in definitions)
    elongation channel (defined in embodiments)
    connection points (defined in embodiments)

After the long nucleic acid molecules have been interrogated, based on the analysis of the interrogation, the molecules may then be exposed to additional reagent exposure and/or physical manipulation. For example, based on some decision criterion from the interrogation results, the molecules may then be exposed to any of the following: FISH probes, PCR primers, barcodes, primers with barcodes, MDA primers, labeling bodies, physical mapping labelling bodies. In some embodiments, the molecules can then be collected for further analysis, performed on the device, or external to the device via extraction of the molecules. Additional analysis can include, but not limited to: mapping, sequencing, array-CGH, SNP-arrays, 3D Mapping, amplification (PCR), or additional cytogenetic methods, such as hybridizing FISH probes.

Active Microfluidic Device for Single Package Capture and Interrogation

One embodiment of the device is described in FIG. 14(A). The main fluidic features of the device include an input sample loading channel (1410), a single package capture site (1408), a reaction chamber (1411), which also serves as an interrogation region for this embodiment, and an entropic barrier (1415). The fluidic connection points (1401, 1402, 1403) in this figure, and all subsequent figures, represent a fluidic connection to some other microfluidic device component within the device, for example an inlet or outlet port to the outside of the device, a channel, a well, a mixer, a droplet generator, a droplet injector. In this embodiment, the input sample of suspended packages (1404) enters the sample loading channel via 1401 and under an external force, the packages flow towards 1402. During the transit from 1401 to 1402 the package will encounter at least one capture site (1408). A variety of different capture sites geometries have been previously demonstrated [Wheeler, 2003] [Le Gac, 2009] where-by laminar flow fluid lines (1407) guide the package into the capture site in which there is an opening large enough to allow fluid flow to exit from the capture site (thus allowing flow into the capture site), but too small for the package to transit through the flow port (1409) under the operationally applied force. In all cases, the capture site opening and chamber are sized just large enough to accommodate a single desired package, such that once occupied with a package, the occupying package excludes other occupying packages. In some device embodiments, fluidic features (1406) are included in the sample loading channel that act to modify the laminar fluid flow lines so as to improve the probability of package capture in the capture site. In addition, there is a third egress point, the narrowing connection (1413) that connects the capture site (1408) to the reaction chamber (1412). As with 1409, the narrowing connection (1413) is sized to be too small for the package to pass through under the operationally applied external force.

After the package has been captured, it is now desired to transfer the contents (1412) of the package into the reaction chamber (1411). In this embodiment device, there are at least two different methods of transfer. In the first method, the package is lysed while inside the capture site by any of the lysing methods described in the definitions. If the lysing is to be done by a lysate agent, the lysate agent may be flowed from fluidic connection point 1401 to fluidic connection point 1402, or more preferably, flowed from fluidic connection point 1401 to fluidic connection point 1403. Once lysed the released macro molecules from the packages are transferred into the reaction chamber, via the narrowing connection, by an applied external force. In the second possible method, the package is directly transferred into the reaction chamber via an applied external force of sufficient magnitude to pass the package through the narrowing connection, and once inside the reaction chamber, the package is lysed by any of the lysing methods described in the definitions. In some embodiments, the operational steps of capturing the packages in the capture site, lysing the package, and transferring the package contents into the reaction chamber may be monitored by the controlling instrument using any means available to it. In some embodiments, the controlling instrument may use the monitored data as part of a feedback system to adjust, restart, or halt the process.

In all embodiments, the reaction chamber (1411), is defined as an enclosed fluidic chamber within the fluidic device such that excluding the fluidic connection from the capture site (1408), the reaction chamber is designed such all fluidic connections are through an entropic barrier. In FIG. 14(A) this is demonstrated by the entropic barrier (1415) that separates the reaction chamber (1412) with the fluidic connection 1403, where-by in this embodiment, the entropic barrier comprising of pillars (1414). In the preferred embodiments the fluidic connection from the capture site to the reaction chamber also contains an entropic barrier, for example: if the narrowing connection (1413) presents an entropic barrier to a large nucleic acid molecule (1412) in the reaction chamber. As described in definitions, when all fluidic connections out of a fluidic chamber are through an entropic barrier, the fluidic chamber is an entropic trap to the deformable object occupying said fluidic chamber. The reaction chamber is designed such that various solutions containing different reagent compositions and concentrations may be flowed through the reaction chamber, while maintaining packages and/or long nucleic acid molecules within said reaction chamber, so as to prepare the molecules for interrogation. In the preferred embodiment, the fluidic device is designed and operated such that at any single point of time, only long nucleic acid molecules from a single originating package may occupy the reaction chamber. In this embodiment shown in FIG. 14(A), the reaction chamber and the interrogation region are the same fluidic feature (1411).

In some embodiments, before or during the interrogation of the long nucleic acid molecules (1412), the molecules are to be positioned within the chamber in such way that the molecules are substantially not in physical contact with each other in order to aid identification of the individual molecules during interrogation. In some embodiments, before or during the interrogation of the long nucleic acid molecules, the molecules are "prepared for interrogation" using devices and methods previously described.

In some embodiments, the interrogation region can be used to analyze multiple packages in a serial manner. When desired, the long nucleic acid molecules can be flushed from the interrogation region through the entropic barrier (1415) via application of sufficiently large external force. In some embodiments, the process of flushing is assisted by adding cleaving agents or photocleaving processes to reduce the physical size of the molecules in the chamber, and thus reduce the minimum force necessary for the molecules to overcome the barrier. In some embodiments, the chamber is also flushed with solutions, including solutions containing various reagents. In some embodiments the process of flushing the molecules from the interrogation chamber is monitored and controlled by the control instrument to ensure the flush is complete. Once the chamber has been flushed, the process previously described for package capture and long nucleic acid molecule interrogation can be repeated.

FIG. 14(B) represents a device and method embodiment with many similar features and functions as demonstrated in FIG. 14(A), but with additional functionality to capture, prepare, and interrogate two packages simultaneously or in series. Referring the to the previous description for FIG. 14(A) 1425 are packages suspended in solution (similar to 1404), 1426 are laminar flow lines (similar to 1405), 1427 is a fluidic feature to manipulate fluidic flow lines (similar to 1427), 1428 is the laminar flow line that guides the a package into a capture site, 1429 is a single package capture site (similar to 1408), 1430 is the laminar flow port (similar to 1409), 1431 is the Sample Loading Channel (similar to 1410), and 1401 and 1402 are the fluidic connection ports to the Sample Loading Channel (respectively similar to 1401 and 1410).

In this embodiment device and method, there is a second capture site (1433) which is capable of capturing a second package (1432). There are many different modes of operation for this device. In one preferred embodiment, a solution of suspended packages is flown from 1421 to 1422 until both capture sites 1429 and 1433 have captured packages. Capture statistics may be determined and confirmed by control instrument. Once both sites have captured packages, their respective contents of long nucleic acid molecules may then be transported into their respective interrogation regions using any of the processes similar to that previously described for the embodiment 14(A). Here, capture site 1429 is fluidically connected through a narrowing connection 1437 which is then fluidically connected to its respective interrogation region/reaction chamber 1436. Similarly, capture site 1433 is fluidically connected through a narrowing connection which is then fluidically connected to its respective interrogation region/reaction chamber 1441. Key to the successful operation of the device is the ability to maintain physical separation of the long nucleic acid molecules that originate from different packages. Failure to maintain separation may compromise the device's ability to facilitate single-cell analysis without ambiguity. This is achieved by an entropic barrier 1440 that separates the two interrogation regions, which in this embodiment, is comprising of pillars 1439. In addition, in this embodiment, the two interrogation regions are in fluidic connection to fluidic connection ports 1423 and 1424, through respective entropic barriers 1434 and 1443. In this one preferred embodiment, once the molecules are in their respective interrogation regions, solutions containing reagents of various compositions can be flowed between 1423 and 1424, so as to expose the molecules in the interrogation regions to said reagents, while maintaining single package separation. This is highly advantageous, as it allows for multiple package (in this embodiment: two) processing simultaneously. All the previously described device features and methods in FIG. 14(A) used for preparing the molecule for interrogation, and interrogation itself, can also be implemented in this embodiment on the two packages. This embodiment can be expanded to any number of capture site-interrogation region pairs, so that large number of packages may have their contents "prepared for interrogation", and interrogated simultaneously or serially, all while maintaining physical separation of the contents that originate from separate packages. In some embodiments the device may have more than 5 capture site-interrogation region pairs, more than 10 capture site-interrogation region pairs, more than 50 capture site-interrogation region pairs, more than 100 capture site-interrogation region pairs, more than 500 capture site-interrogation region pairs, more than 1000 capture site-interrogation region pairs, more than 5000 capture site-interrogation region pairs, more than 10000 capture site-interrogation region pairs.

In a further embodiment of FIG. 14(B), there may be situations where the device is operated without all capture sites fully occupied, for example if the sample concentration is very low. In a further embodiment, there may be situations where it is advantageous to only interrogate a selected sub-set of captured packages. The sub-set of selected captured packages may be based on some criteria. For example: a desired statistical sampling number, or a desired package shape, physical conformation, form, type, phenotype or marker. For example, the desired package may represent a particular cell of interest, a particular cell type of interest, have an association with a particular disease of interest, be a circulating cancer cell, a tumor cell, have a bound marker that identifies it, originate from a particular tissue of interest. In order to select a sub-set of captured packages, photo lysing can be employed by the control instrument, targeting focused photons on the package of interest.

Figure 14:
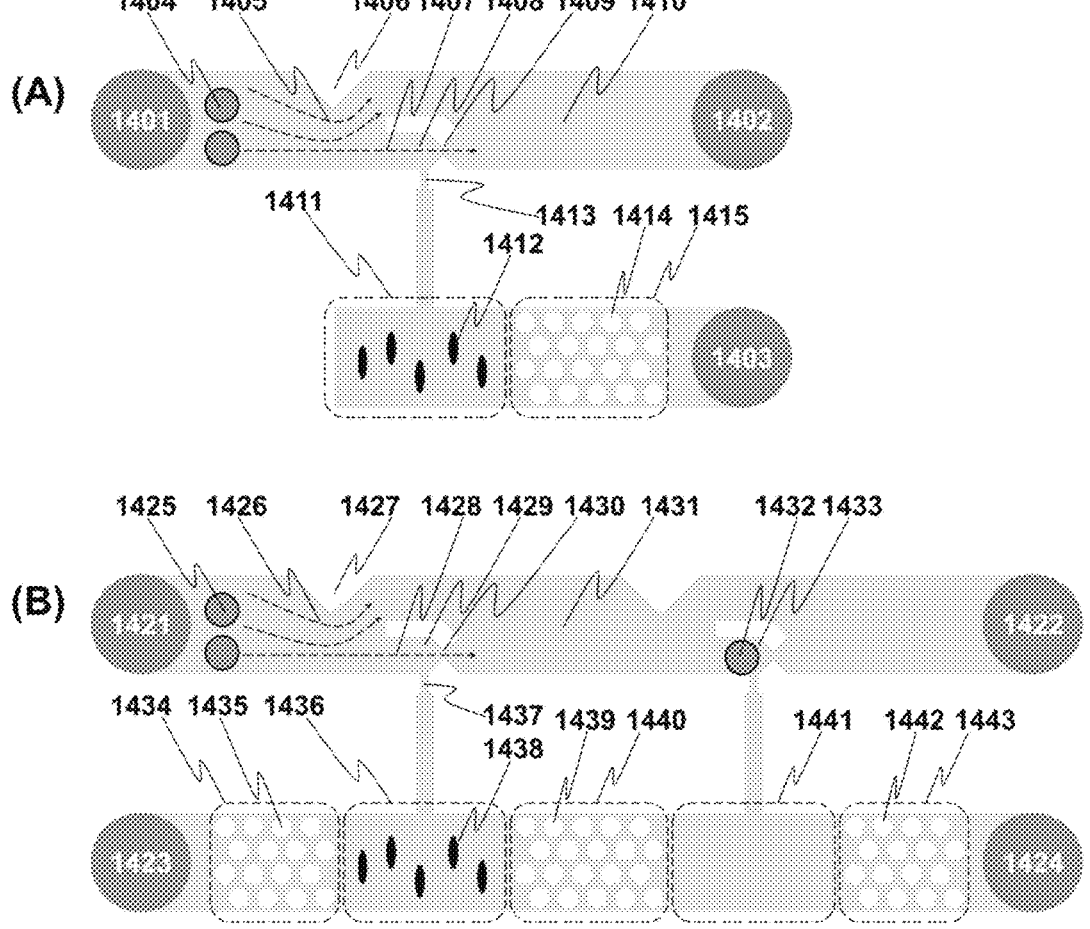
FIG. 14(A) illustrates a fluidic device for capturing a single package, such that the package contents of nucleic acid molecules can be interrogated in an interrogation region (reaction chamber).
FIG. 14(B) illustrates a fluidic device for capturing two single packages in parallel, with each single package respective contents of nucleic acid molecules interrogated in a distinct interrogation region (reaction chamber), where-by two interrogation regions are fluidically connected via an entropic barrier.
Figure 15:
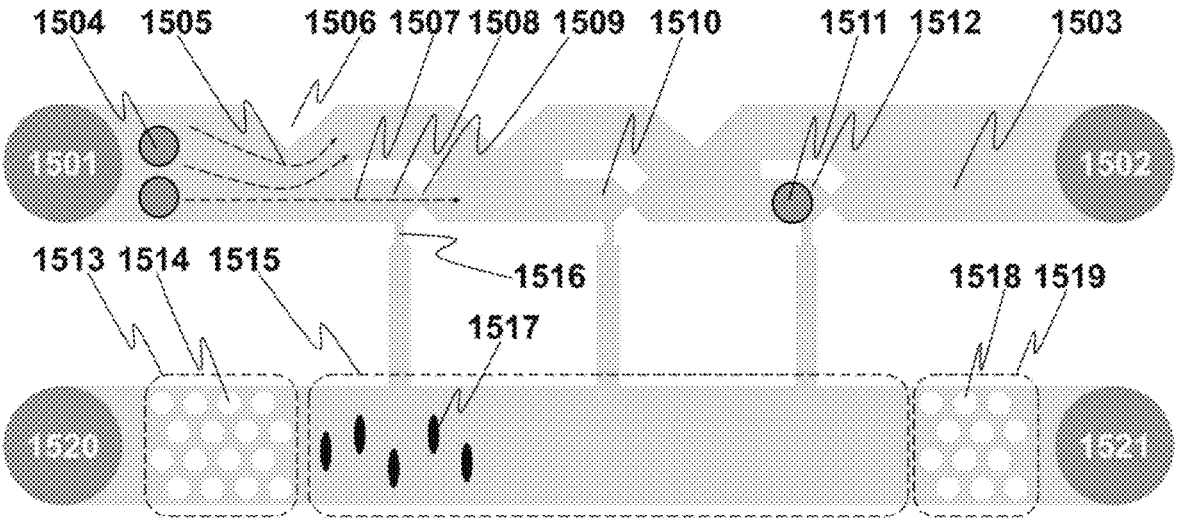
FIG. 15 illustrates a fluidic device for capturing three packages in parallel, such that each package's respective contents of nucleic acid molecules can be interrogated in a shared interrogation region (reaction chamber), and the interrogation region has two fluidically connected channels with an entropic barrier.

Active Microfluidic Device for Selective Single Package Capture and Interrogation FIG. 15 represents a device and method embodiment with many similar features and functions as demonstrated in FIG. 14(A), but with additional functionality to capture, prepare, and interrogate three packages in series. Referring the to the previous description for FIG. 14(A) 1504 are packages suspended in solution (similar to 1404), 1505 are laminar flow lines (similar to 1405), 1506 is a fluidic feature to manipulate fluidic flow lines (similar to 1427), 1507 is the laminar flow line that guides the package into a capture site, 1508 is a single package capture site (similar to 1408), 1509 is the laminar flow port (similar to 1409), 1503 is the Sample Loading Channel (similar to 1410), and 1501 and

1502 are the fluidic connection ports to the Sample Loading Channel (respectively similar to 1401 and 1410).

In this embodiment device and method, a single interrogation region/reaction chamber (1515) shares three connecting package capture sites (1508, 1510, and 1512). In addition, the interrogation region is fluidically connected to fluidic connection ports 1520 and 1521 through entropic barriers 1513 and 1519 respectively. In this embodiment device, transferring the package contents from more than one capture site simultaneously via a process described for embodiment in FIG. 14(A) would result in package contents that originated from different packages occupying the same interrogation region. There may be certain embodiments of the device operation where-by mixing of package contents in a single interrogation region is manageable, acceptable, or desirable. For example, the instrument controller can monitor and record the progress of the package lysing and large nucleic acid molecule release, and thus keep track of each molecule individually with respect to their originating package. In another example, the contents of each package may already be pre-labeled with an identifying label, marker, barcode, or the like that can be used to distinguish the contents of each package from each other. In such an embodiment, an interrogation region where-by there is substantial physical confinement to reduce overlapping of the molecules is helpful in allowing the control instrument to maintain track of which molecule is which as the molecules dynamically move within the fluidic environment. Alternatively, in some embodiments, the mixing of long nucleic acid molecules from multiple package origins may not matter, for example if the packages are expected to be largely homogeneous in nature, and the identification of a long nucleic acid molecule in a certain state, regardless of which originating package is sufficient. An example would be identification of a fragile X syndrome on an X chromosome.

In the preferred embodiment method of operation of the device shown in FIG. 15, long nucleic acid molecules 1517 from only a single package are allowed to enter the interrogation region 1515 at a single point in time. This may be achieved by the instrument controller ensuring that only a single package is captured in all the available capture sites. Alternatively, by the instrument controller selectively lysing a single captured package in a capture site, for example by focused photons, potentially based on some decision-making criteria, as discussed previously. Such a device and method embodiment may be highly advantageous if the desired package is a rare package within a collection of packages, as such a device embodiment design may be more efficient in terms of manufacturing cost and improved capture probability. For example, if the desired package is a circulating tumor cell (CTC) suspended in solution that also contains a large number non-CTC cells.

This embodiment can be expanded to any number of capture sites associated with a single interrogation region (reaction chamber), so that large number of packages may be captured, and then depending on the desired operation, have their contents transferred into the interrogation region in a serial manner, parallel manner, or desired combinations. In some embodiments the device may have more than 5 capture sites associated with a single interrogation region, more than 10 capture sites, more than 50 capture sites, more than 100 capture sites, more than 500 capture sites, more than 1000 capture sites, more than 5000 capture sites, more than 10000 capture sites, more than 50000 capture sites.

Figure 16:
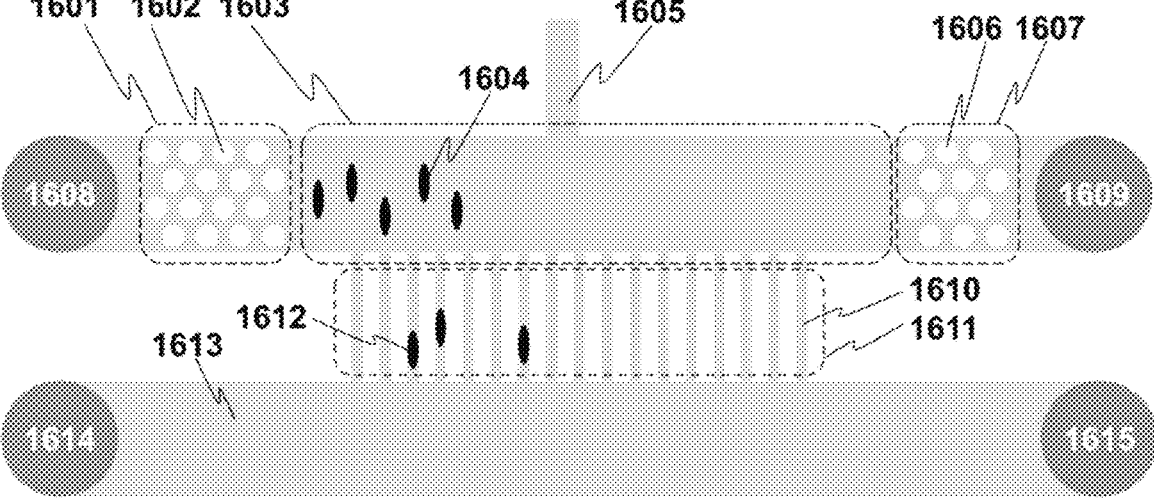
FIG. 16 illustrates a fluidic device with an interrogation region (reaction chamber) that includes elongation channels.

Active Microfluidic Device for Selective Single Package Capture and Interrogation in an Elongation Channel FIG. 16 represents a device and method embodiment with many similar features and functions as demonstrated in FIG. 15, but here in this embodiment, the interrogation region (reaction chamber) 1603, is fluidically connected to at least one capture site (not shown) via a channel 1605, and the interrogation region is in fluidic connection with at least one elongation channel 1610. In the embodiment shown in FIG. 16, there is an array of elongation channels 1611. The interrogation region is fluidically connected to fluidic connection ports 1608 and 1609 through entropic barriers 1601 and 1607 respectively.

Elongation channels are a type of interrogation region, but with a defined purpose of interrogating long nucleic acid molecules in at least a portion of an elongated state. This is achieved by having at least one confining dimension within the channel, preferably a dimension parallel to the optical axis of the interrogation system (ie: depth), less than 200 nm. More preferably less than 100 nm. Even more preferably less than 50 nm.

In the preferred embodiment of the device and method, large nucleic acid molecules 1604 in the are at least partially "prepared for interrogation" within the interrogation region, before a portion of the long nucleic acid molecule 1612 enters the elongation channel. In the described embodiment, the elongation channels are then in fluidic contact with a collection channel 1613 which itself is in connection with fluidic connection ports 1614 and 1615.

Preparation of the Macromolecule for Interrogation

Figure 17:
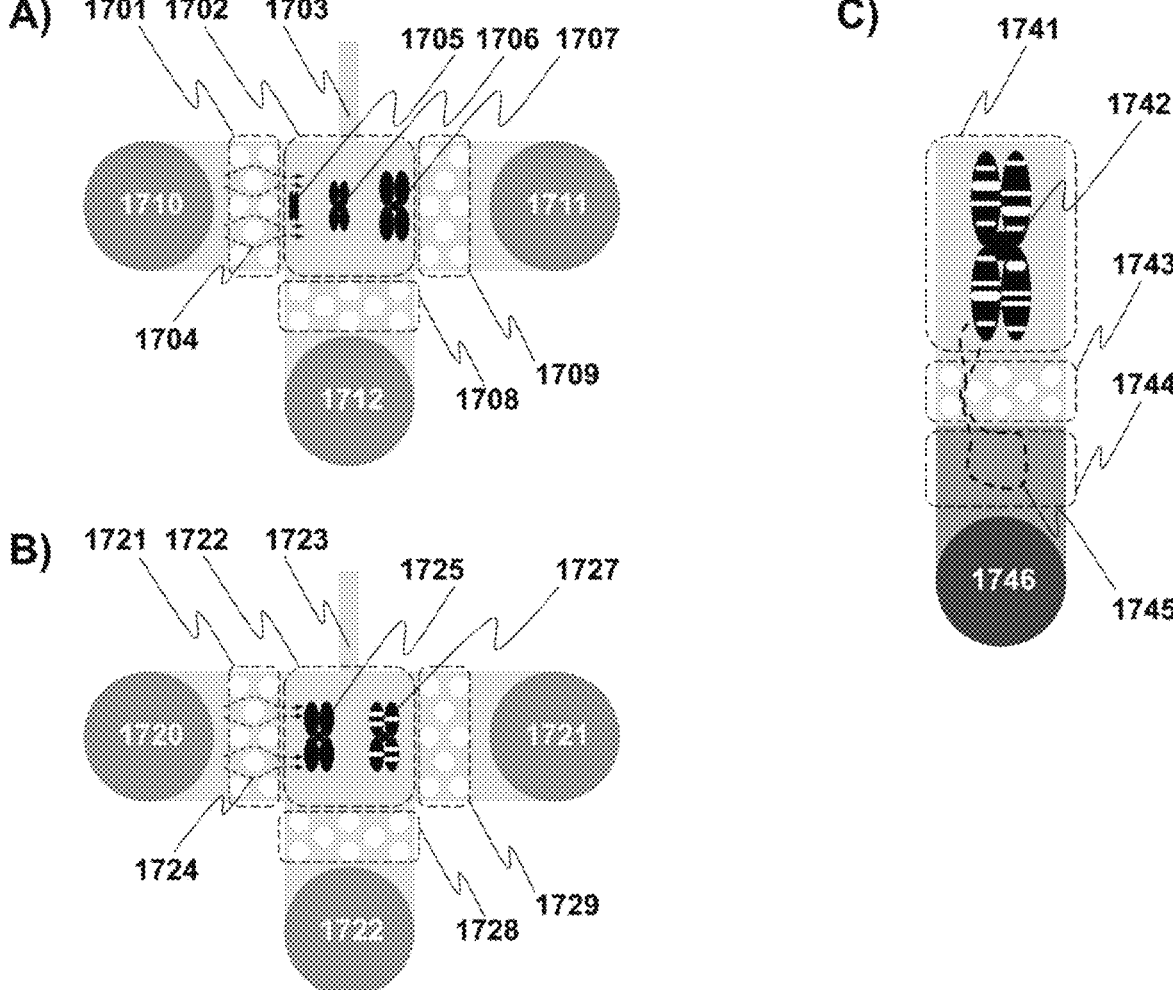
FIG. 17(A) illustrates a top down view of a nucleic acid molecule in a reaction chamber of a fluidic device, at three time points, undergoing physical expansion with the exposure to protein digestion enzymes.
FIG. 17(B) illustrates a top down view of a nucleic acid molecule in a reaction chamber in a fluidic device, at two time points, undergoing generation of physical map via reagent exchanges.
FIG. 17(C) illustrates a top down view of a long nucleic acid molecule in an interrogation region of a fluidic device from which a connected portion of a nucleic acid molecule originates, and said portion is in at least a partial elongated state in an elongated channel.

FIG. 17 demonstrates a collection of embodiment devices and methods for manipulating long nucleic acid molecules in a reaction chamber comprising at least in part, the "preparation for interrogation". FIG. 17(A) demonstrates a device and method of exposing a long nucleic acid molecule to a reagent that digests compounds (eg: DNA binding proteins) that bind the long nucleic acid molecule together, thus releasing the long nucleic acid molecule from a physical confirmation restricted by said compounds. In FIG. 17(A), a reaction chamber (interrogation region) 1702 is in fluidic connection 1703 with at least one capture site (not shown), and three fluidic connection ports (1710, 1711, 1712) respectively through three entropic barriers (1701, 1709, 1708). In this embodiment device and method, a long nucleic acid molecule (here a chromosome in metaphase) is exposed to a solution flow 1704 originating from 1710 that includes enzymes for digesting proteins, preferably protease K, to digest the histones and chaperone proteins that bind together the long nucleic acid molecule into the chromosome structure. Once digested and freed of the binding proteins, a metaphase chromosome will universally swell within a fluidic environment. Such swelling provides an excellent opportunity to interrogate the features within the chromosome at higher resolution. For example, separate karyotyping bands previously not optically distinguishable could now be resolved. Alternatively, two FISH probes of the same color that previously would overlap, now become physically separated from each other. 1705, 1706, and 1707 represent the same long nucleic acid molecule over progressive time points as the molecule swells in the presence of protein digestion enzymes. In some embodiments, the labelling body (for example, the karyotyping stain) is applied to the molecule before exposure to protein digestion enzymes. In some embodiments, the labelling body is applied to the molecule after exposure to protein digestion. In some embodiments, the labelling body is applied to the molecule during the exposure to the protein digestion. In some embodiments, the bodies that bind the long nucleic acid molecule into a forced physical configuration are cleavable entities. In some embodiments, they are photo-cleavable entities, such that the long nucleic acid molecule can be allowed to swell in solution after photo-cleaving the entities via exposure of an appropriate wavelength of light.

FIG. 17(B) demonstrates a device and method of exposing a long nucleic acid molecule to a reagent that binds to the molecule to generate a physical map, in this embodiment, a karyotype banding pattern. A reaction chamber/interrogation region 1722 is in fluidic connection 1723 with at least one capture site (not shown), and three fluidic connection ports (1720, 1721, 1722) respectively through three entropic barriers (1732, 1729, 1728). In this embodiment device and method, a long nucleic acid molecule (here a chromosome in metaphase) is exposed to a solution flow 1724 originating from 1720 that includes at reagents involved for at least one step of a labeling process. The entire labelling process may require multiple steps of different reagent compositions and concentrations, for varying time and temperatures. The result is a generation of a physical map that can be interrogated on the long nucleic acid molecule (1727).

FIG. 17(C) demonstrates a device and method of extracting at least a single strand from a large nucleic acid molecule. Here, a large nucleic acid molecule prepared with a physical map pattern 1742 is in an interrogation region (reaction chamber) that is fluidically connected to a fluidic connection port 1746, through an entropic barrier 1743 and an elongation region 1745 (previously defined). There is at least one other fluidic connection to interrogation region, but these are not shown. In this embodiment, the instrument controller employing any of methods previous discussed to "prepare for interrogation" can pull out, or separate out, at least a single long nucleic acid molecule strand 1745 from the larger mass. In the preferred embodiment, the 2D physical map present in the larger mass 1742 is generated by a method that is compatible with linear physical maps 1745. For example, the physical map is generated by a labelling body that binds to the nucleic acid molecule directly via a process that generates a correlation with the underlying AT/CG content. With such a physical map the labeling process that generates the 2D physical map karyotyping bands also generates a linear physical map along an elongated portion of the long nucleic acid molecule originating from the larger molecule mass. Either the 2D physical map, or the linear physical map can be comparted to a reference. In some embodiments, the long nucleic acid molecule is manipulated so as to extract the single strand from the main mass from a region within the main mass based on analysis of the karyotyping bands. In some embodiments the single strand remains physically attached to the main mass. In some embodiments, the single is separated from the main mass by cleaving, in some embodiments, by photo cleaving. In some embodiments the entropic barrier and the elongation region are one of the same, as the confining space of the elongation region provides a sufficiently large entropic barrier to the long nucleic acid molecule.

Confining Dimension

Figure 18:
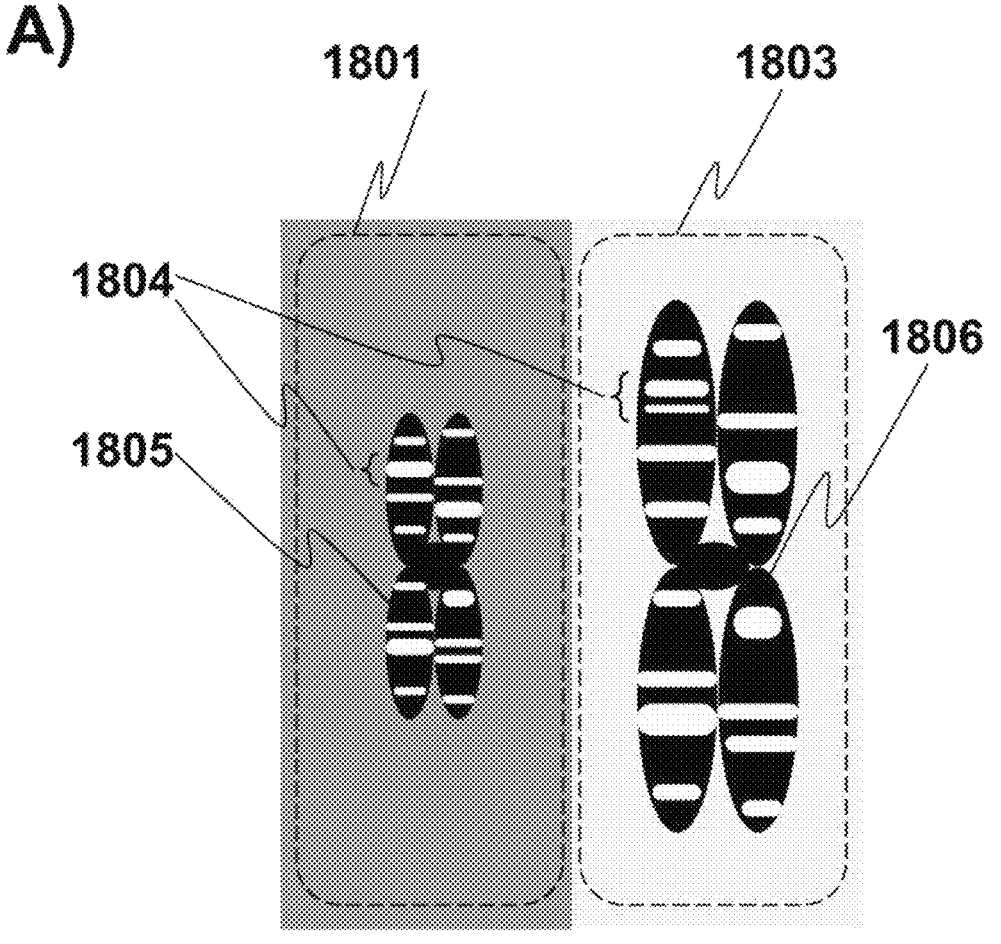
FIG. 18(A) illustrates a top down view of long nucleic acid molecule with a physical map in two different states of physical confinement within an interrogation region of a fluidic device.
FIG. 18(B) illustrates a cross-sectional view of FIG. 18(A)
Figure 18:
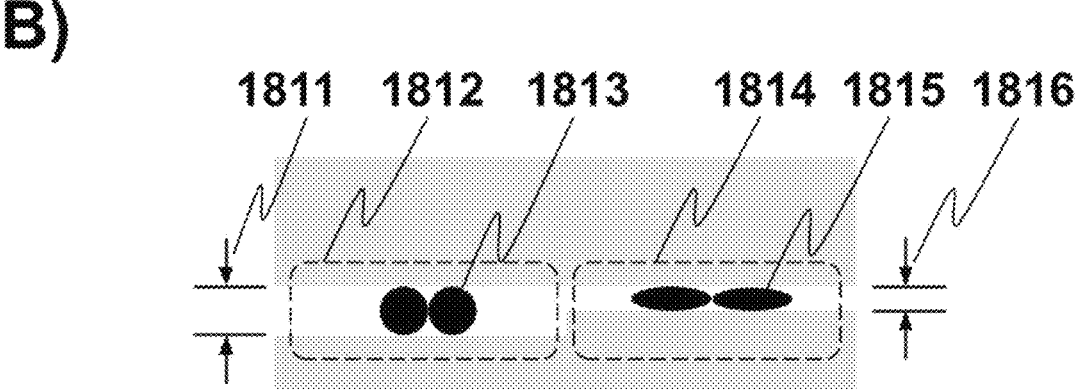

FIG. 18 represents an embodiment method and device where-by the resolution of a physical map on the long nucleic acid molecule (shown here as a karyotype 2D physical map on a chromosome in metaphase) by increasing the physical confinement of the molecule along a dimension that preferably is parallel to the optical axis of interrogation. FIG. 18(A) shows a top view of the embodiment with a long nucleic acid molecule 1805 in a relatively deep section 1801 of the fluidic device, and the same molecule 1806 in a relatively shallow section 1803 of the device. By transporting the molecule from the deep to the shallow section, the resolution of the physical map can be improved. In this particular embodiment, the physical map is a karyotyping banding pattern, in which a single band in the deep section, is resolved (1804) to be two separate bands in the shallow section.

FIG. 18(B) shows a cross-section of FIG. 18(A), whereby the molecule 1813 in the deep section 1812 with depth 1811 has more freedom to physically relax to its most energetically favorable shape, where-as the same molecule 1815 in the shallow section 1814 of depth 1816 has less freedom to physically relax, and so will conform more to the physical boundaries in which it occupies, and so is substantially elongated along the plane normal to the dimension of confinement.

In some embodiments the shallow and deep sections are at physically different locations within the device, as shown in FIG. 18. In some embodiments, the shallow and deep sections are the same region of the device, however the confining dimension is adjustable. In the preferred embodiment, the adjustment is controllable by the control instrument. In some embodiments, there is a range of various depths that span from 1811 to 1816 in which the molecule can be interrogated in.

Elongation Channel Integration

Figure 19:
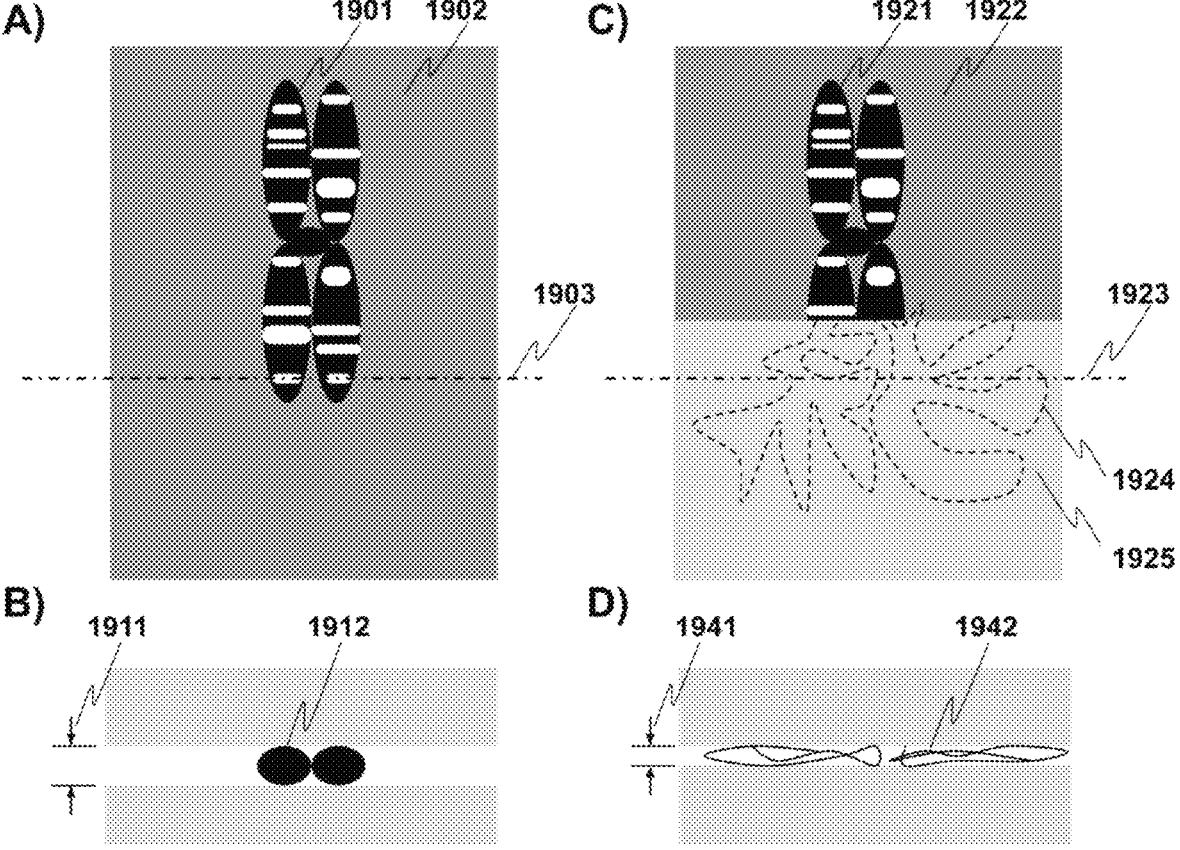
FIG. 19(A) illustrates a top down view of a long nucleic acid molecule with a physical map in an interrogation region of a fluidic device.
FIG. 19(B) illustrates a cross-sectional view of FIG. 19(A).
FIG. 19(C) illustrates a top down view of a long nucleic acid molecule with a physical map in an interrogation region of a fluidic device, with at least a portion of the molecule contained in an elongation channel.
FIG. 19(D) illustrates a cross-sectional view of FIG. 19(C).

FIG. 19 demonstrates an embodiment device and method where-by at least a portion of a long nucleic acid molecule is exposed to an elongation channel under conditions that allow at least a portion of single strand of the long nucleic acid molecule to be in an elongated state during interrogation. FIG. 19(A) is a top-down view of a long nucleic acid molecule with a 2D physical map 1901 in an interrogation region 1902. FIG. 19(B) is the cross-sectional view of FIG. 19(A) through the line 1903 showing the molecule mass 1912 confined by dimension 1911. In the preferred embodiment, the molecule 1901 is a metaphase chromosome, previously exposed to protein digestion enzymes such that molecule has become swollen. In the preferred embodiment, the molecule has a 2D physical map generated from a labeling body bound to the nucleic acid that generates karyotyping bands correlate with the underlying AT/CG density. FIG. 19(C) shows the previously described molecule 1901 in the previously described interrogation region 1902, however here the molecule 1921 in the interrogation region 1922 is at least partially exposed to an elongation channel 1925 such that the long nucleic acid molecule strand 1924 that originates from the molecule mass 1921 can be at least partially elongated within the elongation channel during interrogation. In the preferred embodiment, there is a linear physical map along the length of the long nucleic acid molecule strand 1924 which correlates with the underlying AT/CG density, such that strand can be mapped to a reference, allowing for identification and comparison. In the preferred embodiment the karyotyping band region that individual strand originated from is monitored and recorded by the control instrument. FIG. 19(D) shows a cross section of FIG. 19(C) through the line 1923, showing the individual long nucleic acid molecule 1942 being confined in the elongation channel of confining dimension 1941. In all embodiments 1941 is smaller than 1911. In some embodiments 1911 is less than 20 microns, or less than 10 microns, or less than 5 microns, or less than 2 microns, or less than 1 micron, or less than 0.5 micron. In some embodiments 1941 is less than 500 nm, or less than 200 nm, or less than 100 nm, or less than 50 nm, or less than 25 nm.

In the preferred embodiment 1921 is a chromosome in metaphase, with proteins digested in a fluidic environment, allowing the chromosome to swell, but maintaining substantial structural proportionality of the original chromosome structure. In the preferred embodiment, bound to the nucleic acid is a labelling body that correlates with the underlying AT/CG content, karyotyping bands are formed allowing for identification via interrogation of chromosome type, structural changes of interest, or regions of interest identified by an algorithm or user input. In the preferred embodiment, a portion of the chromosome is then introduced to an elongation channel to further elongate at least a portion of the long nucleic acid molecule. In some embodiments, the portion of the chromosome that is elongated is random. In others, the portion of the chromosome that is elongated is a desired region of the chromosome based on some criteria. In some embodiments, the portion to be elongated is transported into an elongation region. In other embodiments, the portions to be elongated are transported into a region of the interrogation chamber that can become an elongation region through adjustment of physical boundaries.

Figure 20:
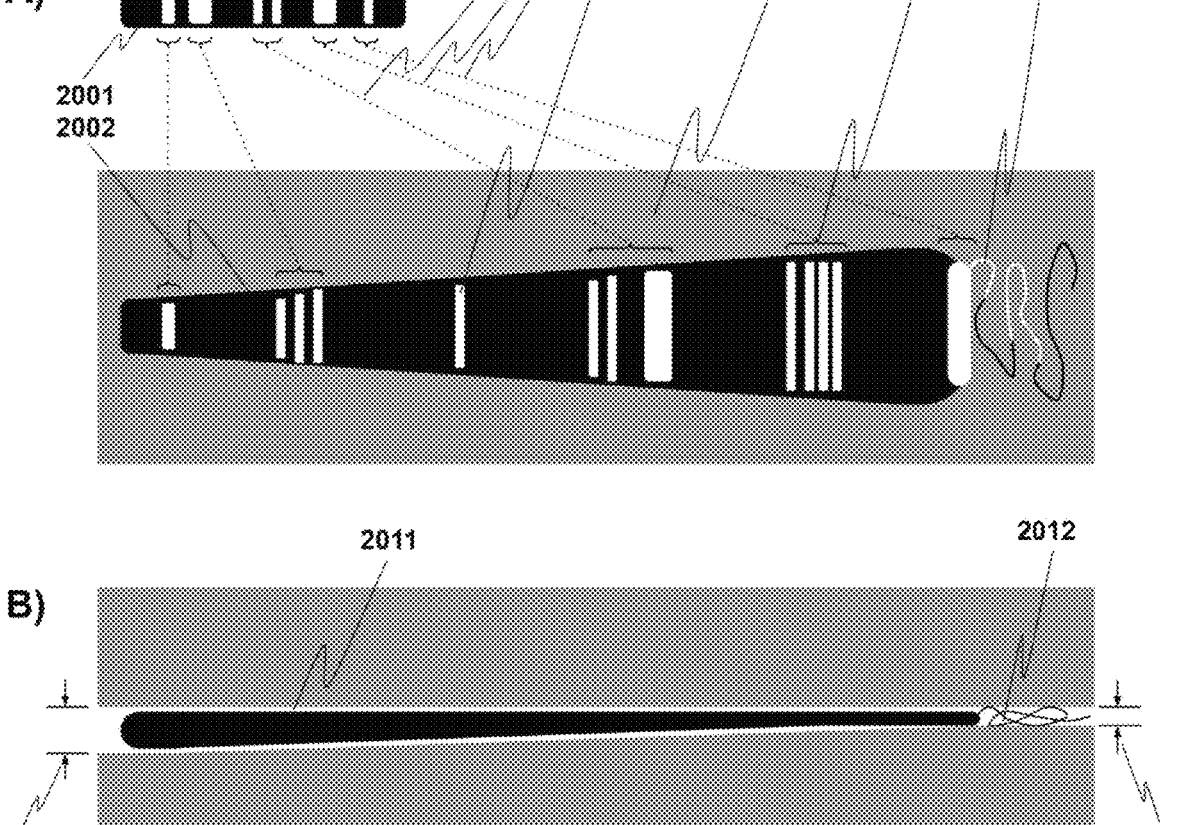
FIG. 20(A) illustrate a top down view of a long nucleic acid molecule with a physical map in a transition region of a fluidic device that connects the interrogation region with the elongation channel by gradually reducing the confinement dimension.
FIG. 20(B) illustrates a cross-section view of FIG. 20(A)

In another embodiment device and method as shown in FIG. 20, there is a transition region from the interrogation region to the elongation channel. In this embodiment a long nucleic acid molecule with a labelling body that correlates to AT/GC density (eg: karyotyping bands) are visible is shown 2001 as it would appear within the interrogation region with a consistent confining dimension parallel to the optical axis of interrogation (eg: channel depth). This same molecule is then shown as 2002 occupying the a region of transition from the interrogation region to the elongation channel. FIG. 20(B) is a cross-section of FIG. 20(A), where-by the confining dimension of the interrogation region 2013 decreases to the confining dimension of the elongation channel 2014, with a substantial portion of the molecule (2002, 2011) occupying the transition region. Such a device embodiment has many potential advantages. First, the resolution of the karyotyping bands will increase as the molecule becomes more confined. The dotted lines (2003) demonstrate how karyotyping bands change as the degree of confinement increases. For example, the collection of bands at 2006 can be individually resolved when the molecule is highly confined but are resolved as a single band molecule is in a less confined state 2001. Furthermore, new bands become apparent, that were previously not visible (2004). In addition, as the degree of confinement increases, and the degree of expansion of the molecule to such confinement increases, the individual nucleic acid strands that compose the molecule become visible (2007, 2012). In one preferred embodiment, the labelling bodies used to generate the karyotyping bands are also capable of generating a linear physical map on the individual nucleic acid molecule strand 2007. In some embodiments this transition region is at least 10 microns in length, or at least 50 microns in length, or at least 100 microns in length, or at least 250 microns in length.

Containing Macromolecules in Entropic Traps

Figure 21:
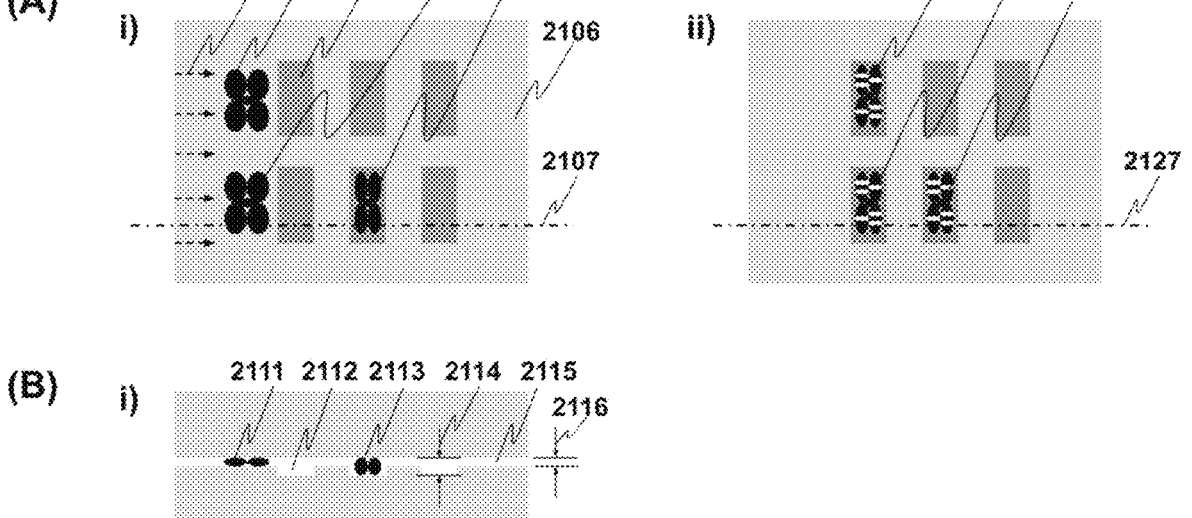
FIG. 21(A) illustrates a top down view of an interrogation region (reaction chamber) of a fluidic device that consists of entropic traps where-by i) long nucleic acid molecules are moved towards the traps, and ii) the molecules are all trapped.
FIG. 21(B) illustrates a cross-sectional view of FIG. 21(A)

FIG. 21 describes a device and method embodiment in which long nucleic acid molecules or packages are flowed into an interrogation region that includes a least one entropic trap 2103. In one preferred embodiment shown in FIG. 21(A), the entropic trap is sized appropriately to capture only one single long nucleic acid molecule, such that once occupied, another molecule cannot enter the trap. In one preferred embodiment there is an array of entropic traps 2103, and the long nucleic acid molecules (2102, 2104, 2105) are chromosomes which are flowed 2101 towards the array. As described previously, once a nucleic acid molecule encounters an entropic trap, it will be energetically favorable to occupy said trap. In one preferred embodiment the number of entropic traps in the array within the interrogation region equals or exceeds the number of long nucleic acid molecules within the interrogation region. In one embodiment, the number of traps in the interrogation region is at least one, or at least 2 or at least 5, or at least 10, or at least 50, or at least 100, or at least 500.

In one exception to the previously described embodiments, in one embodiment device where-by the reaction chamber contains within it at least one entropic trap, the at least one entropic trap becomes the reaction chamber, as once the macromolecule is positioned inside said entropic traps, fluid flow to support interaction of macromolecules with various reagents can be sustained while maintaining the macromolecule's physical isolation within said traps. Thus additional entropic barriers to fluidic connection points are not required, although in some embodiments they are maintained. Once the macromolecules are contained within the traps (2121, 2122, 2123), the macromolecules are exposed to various reagents and conditions to generate karyotyping bands.

FIG. 21(B) shows a cross-sectional view of FIG. 21(A) through line 2107. Here 2111 is the long nucleic acid molecule shown as 2104 which is currently in an interrogation region of critical dimension 2116 which is sufficiently small that the molecule 2111 is at least partially constrained by that dimension. The entropic trap 2112 critical dimension 2114 is larger than 2116, and thus is an entropic trap for the molecule 2113 that occupies the trap (see definitions on entropic traps).

In one preferred embodiment, the entropic trap array is used to maintain physical separation of the long nucleic acid molecules while they are being interrogated. In one preferred embodiment, the entropic trap array is used to maintain the long nucleic acid molecules in physical location while in the presence of a fluid flow that contains various regents of various compositions and concentrations for various time periods and temperatures.

Figure 22:
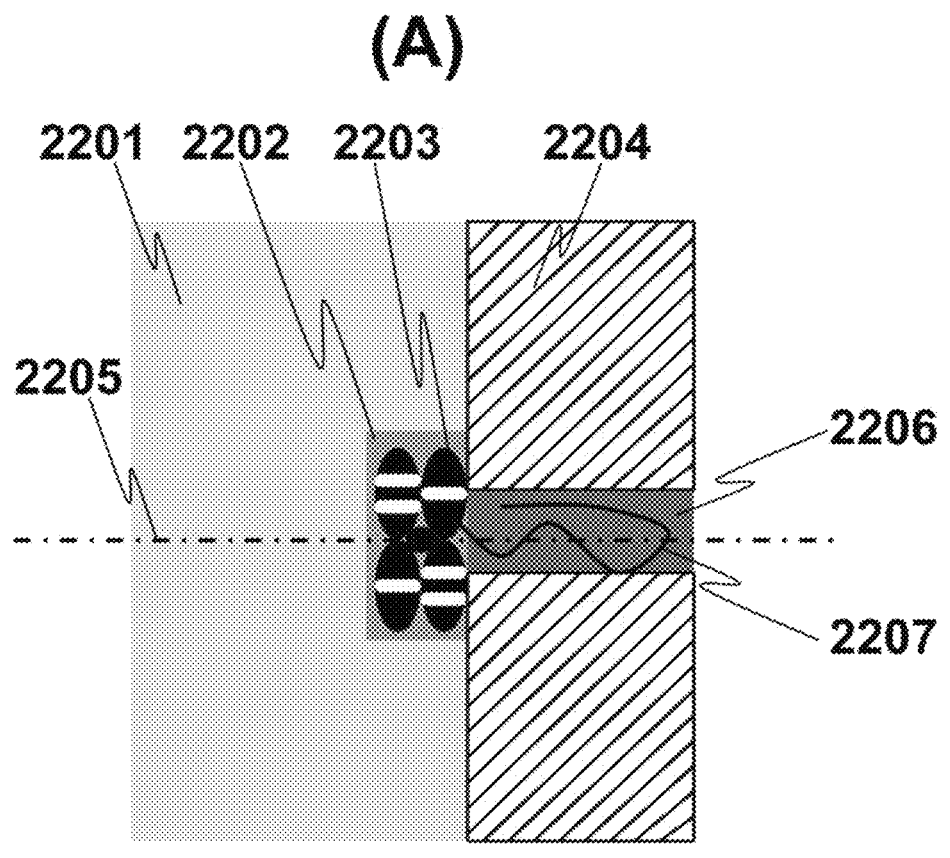
FIG. 22(A) illustrates a top down view of an entropic trap in a fluidic device for long nucleic acid molecules in an interrogation region, the entropic trap being connected to an elongation channel.
FIG. 22(B) illustrates a cross-sectional view of FIG. 22(B)
Figure 22:
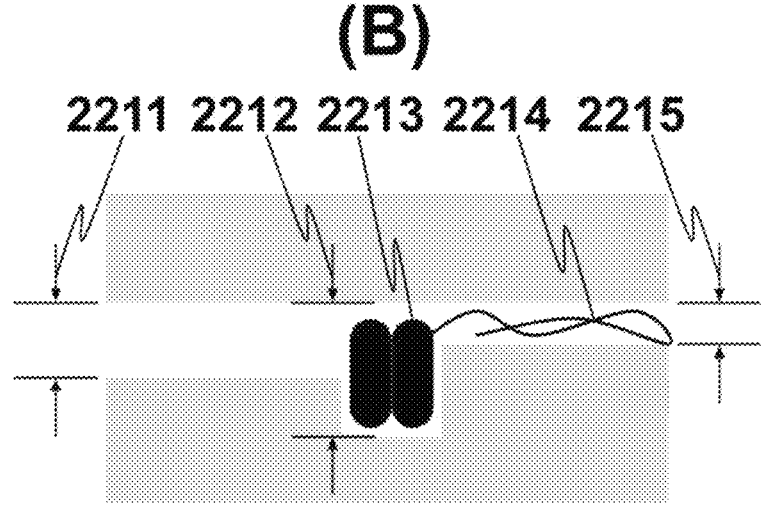

In another variation of this embodiment shown in FIG. 22, a long nucleic acid molecule 2203 is trapped in an entropic trap 2202, which is within an interrogation region 2201, and in fluidic contact with an elongation channel 2206. 2204 is physical barrier. In this embodiment, a long nucleic acid molecule strand 2207 can be extracted from the larger mass 2203, and interrogated in an elongation channel 2206. FIG. 22(B) is a cross-section of FIG. 22(A) through the line 2205, which shows the relative depths of the various features. The entropic trap has the largest confining dimension 2212, the elongation channel has the smallest confining dimension 2215, and the interrogation region has a confining dimension in between 2211. Under the preferred operation method embodiment of the device, at least a portion of the long nucleic acid molecule remains confined to the trap 2213, while a portion of its nucleic acid is interrogated in the elongation region 2215.

Containing Macromolecules in Adjustable Entropic Traps

Here we disclose a device and associated methods for manipulating long nucleic acid molecules and other deformable objects such as cells, nucleoli, and droplets with entropic traps that have controllable entropic barriers. As previously discussed (see definition on entropic barriers), entropic traps can be highly effective at capturing deformable objects, and as such, can be implemented to isolate and sort such objects. However, one significant limiting factor for implementing such a device is tuning the physical dimensions of the entropic barriers such that there is a large operational window for capturing and releasing the deformable object. For example, if the minimum external force is required to release a chromosome from an entropic trap is a flow velocity of a few microns per second, than any desired reagent exchange of the chromosome's surrounding fluid while maintaining the chromosome captured in the trap will be time limited not to exceed this minimum flow rate. The minimum external force required to release the object can be increased by increasing the energy barrier of the entropic trap, typically by reducing the confining dimension of the barrier. However, all things remaining equal, reduction of the confining dimension typically results in a commiserate reduction in the volume flow rate (eg: nanoliters per second), which again impacts the time necessary for reagent exchange within the trap. In the extreme, the confining dimension can be reduced to zero, in which case there is no force large enough to escape the object, nor can any reagent exchange solution flow, as the fluidic egress has been blocked. Optimization of these parameters can be performed with an iterative process of device design and testing, or with numerical simulation provided the simulated models of the objects are sufficiently accurate. However, even if successful, the resulting dimension is only optimized for the specific deformable object in question. Here we disclose a device and method where-by the confining dimension of the entropic barrier can be adjusted on-the-fly to allow real-time optimization of the desired task. Such an invention is particularly valuable when the desired deformable objects to be captured vary in size, such as the 24 different human chromosomes.

Figure 23:
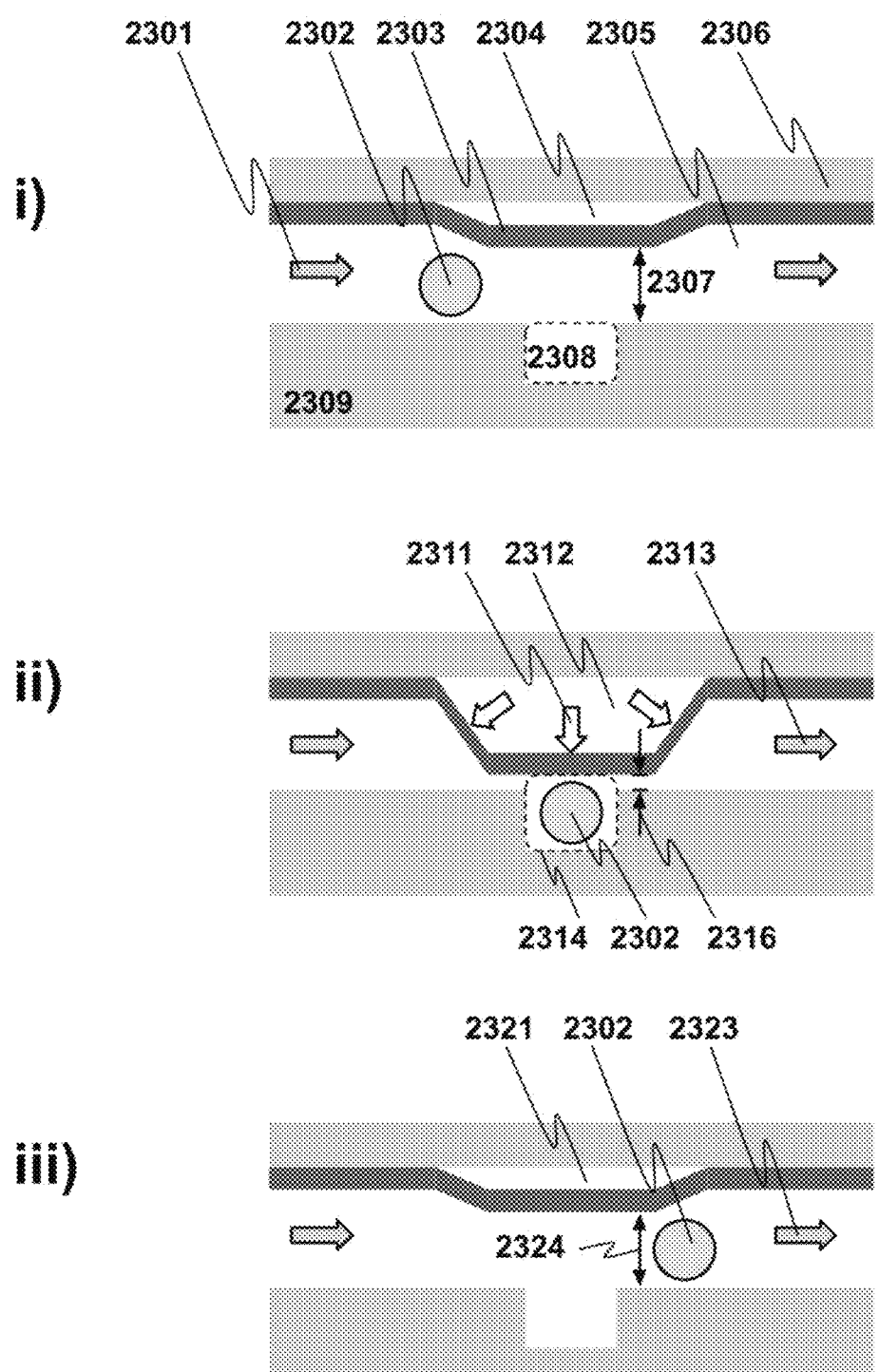
FIG. 23 illustrates an adjustable entropic trap in a fluidic device in which i) a deformable object is approaching the trap, ii) the adjustable confining dimension of the trap is reduced, and the object is trapped in the entropic trap, and iii) the adjustable confining dimension of the trap is increased, and the object is escaped from the entropic trap.

In one embodiment demonstrated in FIG. 23, a pit (2308) defined in a first substrate (2309) is in fluidic communication with a fluidic channel (2305). The lid composed of an elastomeric boundary (2303) above the pit, and defines the height (2307) comprising the entropic barrier's confining dimension. In this embodiment, the height 2307 can be modulated by adjusting the pressure differential between the fluidic channel 2305 that transports the deformable objects 2302 via an applied force 2301, and a second channel 2304 located above the elastomeric material, and below a second substrate 2306 substantially parallel to the first substrate 2309. Here the second channel may carry liquid, gas, or a mixture of either. In this embodiment, the entropic trap is defined by the pit 2308, and the region above the pit to the elastomeric boundary 2304. It should be noted however, that the entropic trap is functionally only a "trap" to the object 2302 when the confining dimension 2307 is sufficiently small in comparison to the object's physical size and conformation (refer to the definition of entropic traps).

In the preferred embodiment, the device is comprising a viewing window such that the response of the deformable object to a change in the confining dimension 2307 and/or external force 2301 can be observed by the instrument controller, and thus, the instrument controller can use a feedback system to control the external force(s) and confining dimension.

FIG. 23 (ii) demonstrates the deformable object (2302) after having been trapped in an entropic trap 2314 defined by the pit and the new confining dimension 2316, that has been reduced from its previous value (2307) via an increase in pressure 2311 in the second channel 2312. Here, the confining dimension is appropriately set by the controller instrument such that the external force 2313 is insufficient to escape the object. At a later time-point, decreasing the pressure in the second channel 2321 to increase the confining dimension 2324, allows for an applied external force 2323 to escape the object.

There are multiple methods of trapping the deformable object. In one embodiment, the object is blindly trapped without observation by defining the confining dimension such that an applied force on the object is sufficient to position the object in the trap, but insufficient to escape it. In the preferred embodiment for blind capture, the entropic trap is physically defined such that there is only sufficient room to capture a single object. In another embodiment, the deformable object can be monitored by the instrument controller which then modulates the confining dimension and/or external force when the object is in the vicinity of the trap. In some embodiments, the confining dimension and/or applied force can be modulated while at least a portion of the deformable object is in the entropic trap, while under the observation and control of the controlling instrument. In some embodiments, such observations can be used to measure the minimum external force needed to escape or trap an object for a given confining dimension. In some embodiments, such observations can be used to physically manipulate the object's shape and/or conformation. For example, untangling and/or elongating a long nucleic acid molecule that is coiled configuration. In another example, untangling and/or elongating a chromosome that is a metaphase configuration, preferably after, or during exposure to protein digestion.

In another embodiment, the device can be used to form droplets that contain at least one deformable object. In this embodiment, after the deformable object is trapped in the entropic trap, the surrounding aqueous solution is displaced with an oil to form water-in-oil droplets in the pits as previously disclosed [Amselem, 2016]. It should be noted that the confining dimension cannot be zero for such an embodiment, as fluid exchange between the transport channel and entropic trap is required for water displacement by oil. Once the droplet has been formed, it can be released by either increasing the external force, increasing the confining dimension, or a combination of both.

In another embodiment, an array of entropic traps with independently addressable confining dimensions can be used to sort and/or select deformable objects. For example, a collection of deformable objects are transported into a fluidic chamber comprising such an array. Either by blind capture or with instrument controller feedback, the objects are trapped in said traps. In the preferred embodiment, only one object per trap. The instrument controller can then interrogate the trapped objects, and based on a decision criterion, individually release a desired object by adjusting the object's respective trap's confining dimension.

Figure 25:
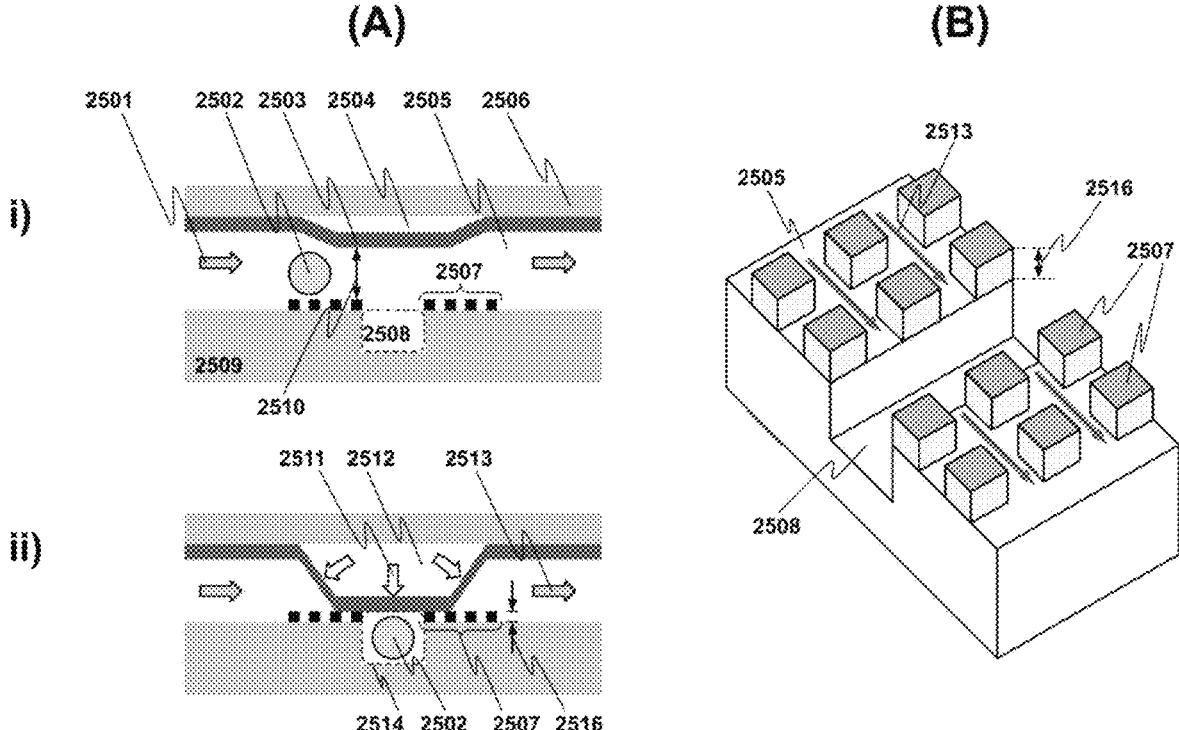
FIG. 25(A) illustrates a fluidic device with an adjustable entropic trap with patterned features to set the minimum confining dimension, in which i) a deformable object is approaching the trap, and ii) the adjustable confining dimension of the trap is reduced to the minimum value, and the object is trapped.
FIG. 25(B) illustrates an isometric view of FIG. 25(A).

In another embodiment, described in FIG. 25(A), the confining dimension has a non-zero minimum value allowed by patterned features 2507 adjacent to the entropic trap. This embodiment is similar to the previously described in FIG. 23, in that a deformable object 2502 is transported in a transport channel 2505 via an external force 2501 towards a pit 2508 defined in first substrate 2509. Above the pit is an elastomeric boundary 2503 which separates the transport channel, and a second channel 2504, itself defined partially by a second substrate 2506 that is substantially parallel to the first substrate 2509. In this embodiment however, with an increase in pressure 2511 in the second channel 2512, the elastomeric boundary can come into contact with the patterned features 2507. The patterned features are designed such they allow for fluidic contact between the entropic trap 2515 and the transport channel 2505 when the features are in physical contact with the elastomeric boundary 2511 as shown in ii). As such, an external force 2513 can be used to transport solution into, and out of, the entropic trap in this state. Furthermore, the confining dimension 2516 is defined by the patterned feature's physical dimensions. Such an embodiment is advantageous when desired confining dimension is known, and does not need to be optimized, as by sufficiently pressurizing the second channel, the desired confining dimension is achieved.

FIG. 25(B) demonstrates an isometric view of the device in FIG. 25(A) with the elastomeric boundary (2503) and second substrate (2506) not drawn for clarity. On adjacent sides of the pit 2508 are the patterned features 2507, which in this embodiment, are pillars. The spacing between the pillars allows for fluidic connection 2513 between the pit 2508 and the transport channel 2505. The patterned features can be any collection of features that allow for said fluidic connection after physical contact with the elastomeric boundary. The dimensions of the features will depend on the intended use, particularly what type of deformable object is to be trapped.

Figure 24:
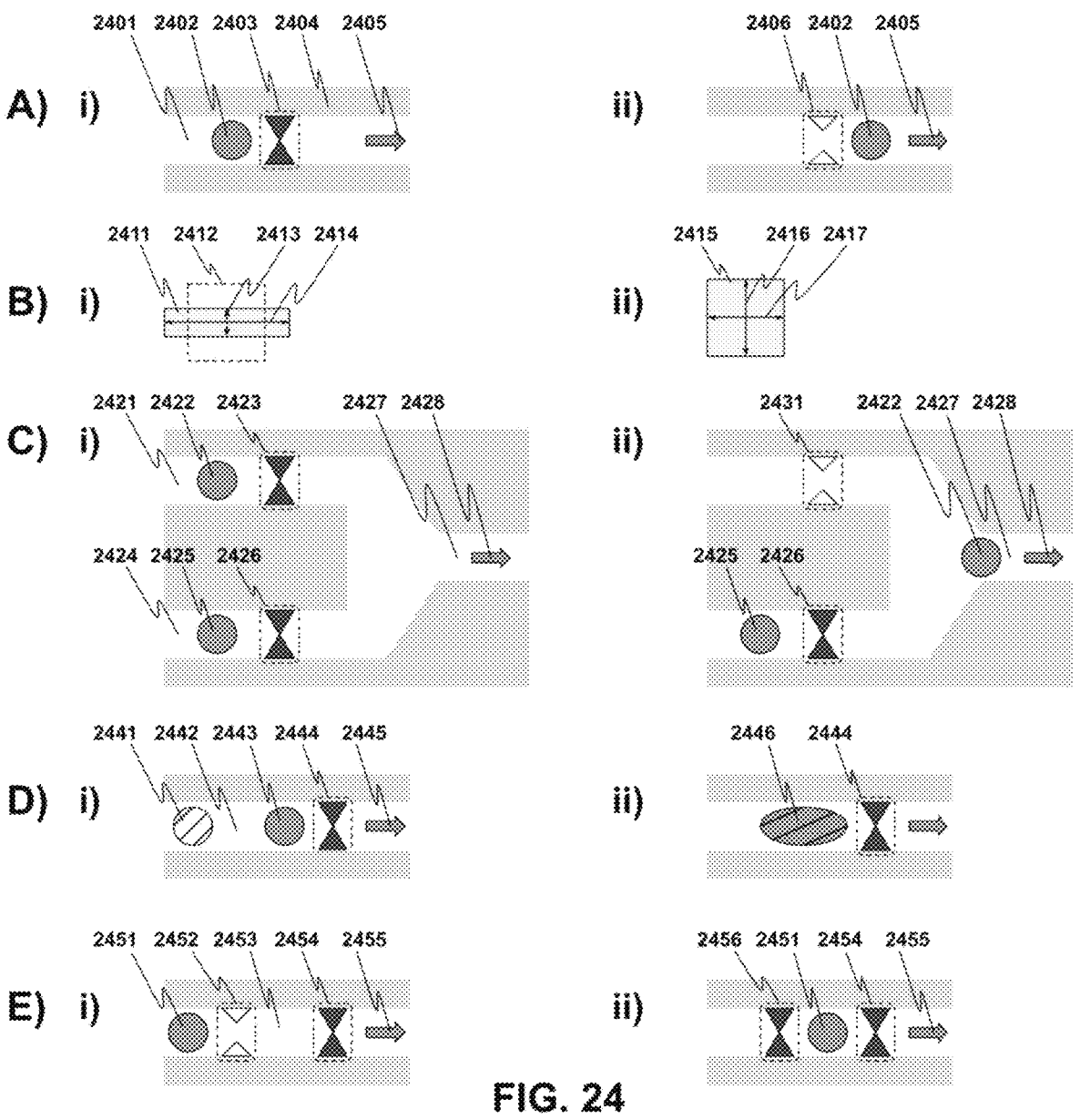
FIG. 24(A) illustrates a schematic of a deformable object in fluidic device in which i) the object is blocked with closed adjustable entropic barrier gate, and then ii) releasing the object by opening the gate.
FIG. 24(B) illustrates a schematic of a cross-section of an adjustable entropic barrier gate in a fluidic device for which i) the gate is closed, and ii) the gate is open.
FIG. 24(C) illustrates a schematic of a fluidic device for selecting deformable objects in which i) there is a selection of objects to choose from, and ii) after a selection has been made.
FIG. 24(D) illustrates a schematic of a fluidic device for merging deformable objects in which i)th objects are co-localized behind a closed gate, and then ii) merging said objects together.
FIG. 24(E) illustrates a schematic of a fluidic device for trapping deformable objects in which i) the object is transported through an open gate, towards a closed gate, and then ii) trapping said object between two gates.

In another set of embodiments described in FIG. 24, the variable barrier is used to control deformable object flow within a microfluidic device, in particular, when the deformable object is a droplet. It has been previously shown that changes in feature size in the channel dimensions can be used to manipulate droplets. These changes include openings to physically pin droplets [Boehm, 2008, U.S. Pat. No. 9,664,619], and constrictions to block droplets [Fraden, 2007, U.S. Pat. No. 8,592,221]. However, again the dimensions of these features must be set at the time of manufacture of the device, and thus their utility is limited. Most droplet microfluidic devices operate in a mode where-by the external force used to transport the droplets is typically held constant, or modulated to suit a desired function, such as droplet formation. As such, modulating an external force on a droplet to enter or escape an entropic trap is often not an option allowed by design constraints. Furthermore, even if modulating an external force to manipulate a droplet is feasible, said external force will also be applied to neighbor droplets, as droplets are often generated in great numbers and occupy the fluidic device in high densities. By incorporating entropic barriers with adjustable confining dimensions, significant individual droplet control functionality can be incorporated into a droplet microfluidic device. Furthermore, adjustable entropic barriers are highly advantageous in fluidic devices where-by blocking or trapping deformable objects with valves that completely (or nearly completely) stop fluid flow would not be feasible as the device design requires a substantially continuously fluid flow. Such adjustable entropic barriers allow for control over the droplet's position, without significantly interrupting fluid flow in the device.

FIG. 24(A) demonstrates a simple schematic to express gating functionality in which a "closed" entropic barrier is represented as a dark gate 2403 when the confining dimension is sufficiently small to block the transport of a deformable object 2402 in a fluidic channel 2401 in the presence of an external force 2405. Similarly, when confining dimension is widened as shown in ii) to allow for the object 2407 to transit through the entropic barrier with an external force 2405, the "open" entropic barrier is represented as a white gate 2407.

FIG. 24(C) demonstrates an embodiment where-by such gates are used to implement a deformable object selection system. Here, two deformable objects (2422 and 2425) are each respectively in a fluidic channel 2421 and 2424, with each channel respectively having a gate 2423 and 2426, and each channel in fluidic connection with an outlet channel 2428. With the gates in closed position, both deformable objects will remain behind their respective gate with the external force applied 2428. However, by opening the gate 2431 (previously closed as 2423), the object 2422 can transit through the gate, and enter the exit channel. Meanwhile, the other deformable object 2425 remains behind the closed gate 2426. Such a selection device can be used to select, sort, or discard deformable objects. In some embodiments, the opening or closing of the gate(s) may be based on a timing mechanism, such that the release (or holding back) of an object allows for synchronizing with other functions in the fluidic device. In some embodiments, the opening or closing of the gate(s) may be based on an interrogation of the deformable objects in which some criterion for release (or holding back) is determined.

FIG. 24(D) demonstrates an embodiment where-by such a gate can be used to merge two mergeable deformable objects (eg: droplets). Here, two different objects 2441 and 2442 in a fluidic channel 2442 with a closed gate 2444 in the presence of an external force 2445. As the gate is closed, the two objects will be pushed up against each other at the gate by the external force, and under suitable conditions, will merge into a single object 2446. Such an embodiment can be used to merge droplets containing different contents so as to initiate, modify, or stop, a reaction. For example, such an embodiment may be downstream for a selection mechanism similar to that shown in FIG. 24(C) in which a variety of droplets of different contents can be selected, thus allowing for on-the-fly mixing of different contents of the desired reagent and ratio. This is highly advantageous, as droplet merging in devices typically relies on merging multiple flows of droplet streams in a continuous fashion, requiring careful synchronization of the dynamic movements, and thus minimal flexibility for selecting different combinations of droplets to be merged.

FIG. 24(E) demonstrates an embodiment where-by two such gates are employed to form an entropic trap. Here, a deformable object 2451 transiting in a fluidic channel 2453 due to an external force 2453 passes through a first gate in an open state 2452, and will halt at the second gate in a closed state 2454. Once the object has passed through the first gate, the first gate closes (2456), thus trapping the object between the two gates. Such an embodiment is highly advantageous, as it allows for reversing the direction of the external force, while maintaining the object in the desired location (trap). Alternatively, if there are multiple objects in the channel, such an embodiment can be used to physically isolate such objects, and then release when desired. This allows for on-the-fly tuning of the physical spacing of the object in the downstream channel. In applications where-by synchronization of the droplets in a single-file droplet stream with some process downstream, such control is highly beneficial. For example, merging droplets from multiple droplet streams to form combinatorial variations droplet contents.

There are multiple possible methods of manufacturing such a gate, so long as the adjustment of the cross-section results in a modulation of the entropic barrier energy height for the deformable object in question, as previously discussed in the definitions. FIG. 24(B) demonstrates an example cross-section of the fluidic channel in which the confining dimension of the entropic barrier is defined, where gate transitions from "closed" 2411, to "open" 2415. In this embodiment, when the gate is closed, the confining dimension 2413 is reduced from the original cross-section of the channel when open 2416, however the other non-confining dimension 2414 has increased from the original channel when open 2417, in much the same way compressing a circular hoop reduces one axis, and enlarges the other axis, to form an oval. (For reference, 2412 shows the dimensions of the channel when open 2415.)

It should be noted that words referencing orientation (eg: "height", "above", etc) are used only for clarity in describing a particular example, and do not limit the invention. The adjustable confining dimension can be altered along any spatial axis within the fluidic device. In addition, while one dimension becomes more confining to increase the entropic energy barrier, other dimensions may expand (as shown in FIG. 24(B)), or remain the same, or decrease. Similarly, the overall cross-section area may decrease, stay constant, or increase.

In some embodiments, the gate can be manufactured in much the same was as an active micro-value used to control fluid flow in a microfluidic device, as reviewed by [Ahn, 2006], however in these embodiments, there is no requirement to regulate fluid flow as required of a value. Instead, the adjustable entropic barrier requires the ability to control at least one confining dimension, and so can utilize micro-valve technology that modulates channel dimensions, including magnetic, electrical, piezoelectric, or thermal effects that are integrated into the device. Alternatively, non-mechanical elements can be integrated into the device to modulate the channel dimension such as bi-stable materials, phase-change materials, rheological materials. In addition, external mechanisms can be used to modulate a channel dimension by applying a vacuum or pressure to the device.

In the preferred embodiment, the adjustable entropic barrier is comprising an elastic material that forms at least a portion of the channel who's confining dimension will be modulated. Prior art examples of modulation of a channel dimension via deformation of an elastic material include secondary pressurized channels to form values that close a primary channel [Unger, 1999, U.S. Pat. No. 6,899,137], and to form a roof that encloses nanochannels [Yao, 2015, 2019/0217295]. Alternatively, an external force was used on a device to enclose nanochannel [Leslie, 2017, 2020/0240898], [Mahshid, 2015], [Cohen, 2011, U.S. Pat. No. 10,048,193].

In some embodiments, the described device and methods employing adjustable entropic barriers are at least partially used to "prepare for interrogation" a package or long nucleic acid molecule.

Containing Macromolecules Between Attracting Substrates

In another set of embodiments, a biological body, for example a package or macromolecule, is contained between two substrates comprising a fluidic device, separated by a solution and spacers, that are brought together via an electrostatic force. When an electrostatic field is applied through a liquid between two substrates, charge-carrying mobile bodies in the liquid react to the electrostatic force and collect at one of the substrate interfaces, thus shielding the electric field, and reducing the attractive force between the surfaces. An oscillating electric field of sufficiently high frequency is necessary to prevent such accumulation of charge at the surface. Frequency dependent electrostatic forces have previously been explored as a means of modulating the separation of parallel surfaces in fluidic devices, specifically with the intent of using such forces to open and close valves for fluid control [Sounart, 2005], [Sounart, 2010]. Here we describe embodiment devices and methods that employees an oscillating electric field generated between two substrates to control the movement and/or disrupt bodies between said substrates.

Figure 26:
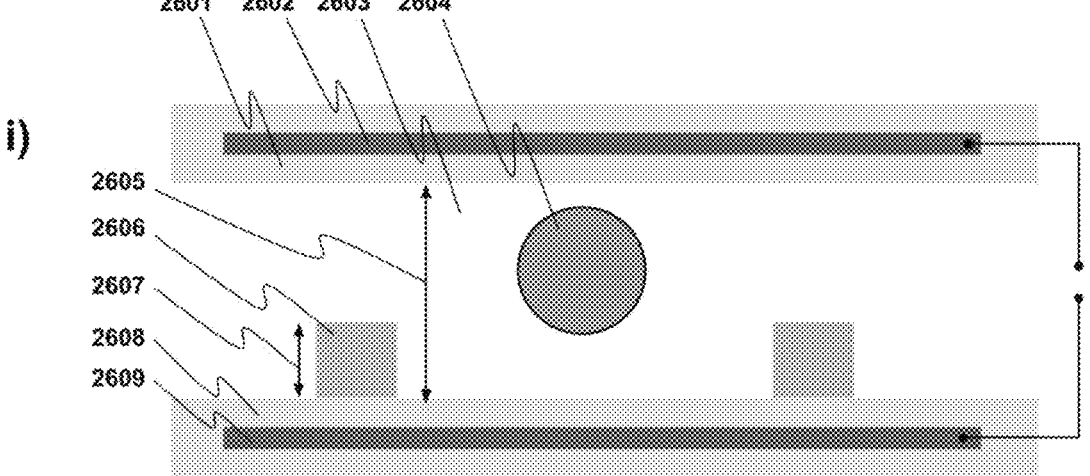
FIG. 26 illustrates an adjustable trap in a fluidic device in which i) a body is brought between two substrates, and then ii) the two substrates are electrostatically attracted to each other to trap the body.
Figure 26:
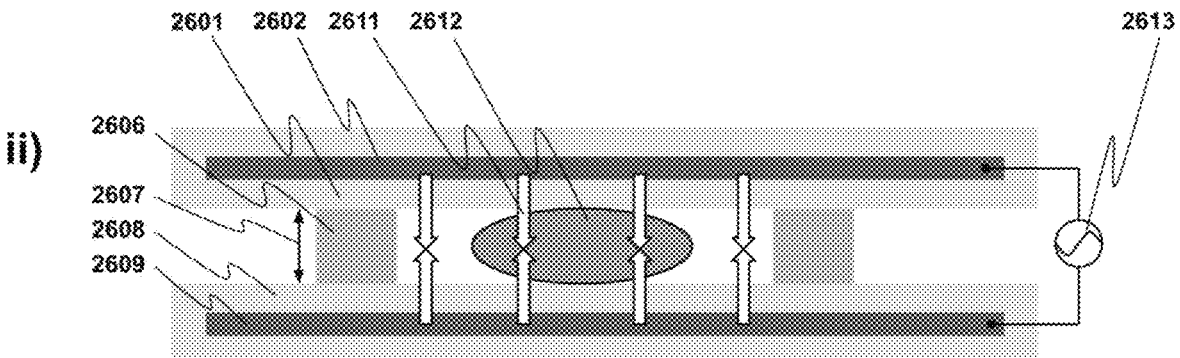

FIG. 26 demonstrates an embodiment device and method where-by two substrates (2601, 2608), each containing a conductive film (2602, 2609), are separated from each other by a distance 2605, and between the substrates is a solution 2603 that contains at least one body 2604. In this embodiment, spacers 2606 are added to at least one substrate such that when the substrates are attracted to each other, the spacer height 2607 defines the minimum distance at which the substrates can be brought within proximity to each other.

When an oscillating voltage source 2613 is applied to the films, an oscillating electric field is generated between the substrates that attracts 2611 the substrates together, resulting in confinement of the body 2612 between the substrates.

In this embodiment, the spacer physical dimensions are defined such that when bodies are physically confined in the vertical dimension between the substrates, when the substrates are in contact through the spacers. Such an embodiment can be used to physically isolate one body from another, to generate an entropic barrier when the bodies are deformable objects, and/or lyse/disrupt the bodies via a mechanical means of compression [Lele, 2015, Patent Application].

In some embodiments, there are no spacers. In some embodiments, spacers are defined on the top, the bottom, or both substrates. In the embodiments where-by the spacers are defined in the substrate(s), the spacers can formed by adding material to the substrate, in which the spacers are at least partially formed from the material added, or by subtracting material from the substrate, in which the spacer are at least partially formed from the material that remains, or a combination there-of. The spacers may be comprising of the same material as the substrate, or a different material. In some embodiments, the spacers are mobile bodies within the solution of a known physical shape, for example beads of a known diameter. One or both substrates may be flexible or deformable. One, or both of the substrates may be transparent. In some embodiments, the modulation of the applied voltage frequencies and magnitude may be controlled, at least in part, by the interrogation of the bodies.

The conductive film is composed of a conductive material that can be embedded in the substrate, or on the surface of the substrate. In the preferred embodiment, the conductive material is transparent to visible light, for example: ITO. In the preferred embodiment, the substrate material is a dielectric material. In some embodiments, at least one conductive film is a metal electrode that is externally applied to the device.

In some embodiments, the oscillating voltage source includes a frequency component between 100 and 1,000 Hz, or between 1,000 and 10,000 Hz, or between 10,000 and 100,000 Hz, or between 1,000,000 and 100,000 Hz, or between 1,000,000 and 10,000,000 Hz, or between 10,000,000 and 100,000,000 Hz.

In another embodiment, the fluidic device is comprising of multiple attracting substrate regions, each with its own electrode. The regions can share a common electrode, or have pairs of electrodes that are independent from other regions. In some embodiments, at least a subset of these regions can have their applied electric field independently controlled from another subset of regions.

In some embodiments, the described device and methods employing attracting substrates are at least partially used to "prepare for interrogation" a package or long nucleic acid molecule.

The height of the spacer(s), their spacing, density, and physical shape can vary depending on the desired application, in particular, the physical dimension of the body being contained. For example, an application where-by it is desired to physically isolate a 50 micron diameter droplet, the spacer material can be a continuous ring of 50 microns in height, with a 50 micron hole in the center in which the droplet may be contained. In another example, an application where-by it is desired to physically confine a metaphase chromosome within a 500 nm dimension parallel to the optical axis to allow for interrogation of the chromosome while exposing the chromosome to a fluid flow of reagents. Here, the spacers are pillars patterned in a ring formation, 500 nm in height, 2 microns in diameter, spaced no less than 1 micron apart, with 10 micron hole in the middle of the ring with no pillars into which the chromosome will be contained. In another example, an application where-by it is desired to lyse a cell via the applied pressure of being captured between the substrates, and so there are no spacers.

Containing Macromolecules in DEP Traps

In another set of embodiments, a macromolecule is physically manipulated by pushing the macromolecule up against a surface of a channel taper so as to confine and elongated the molecule via the application of an externally applied Dielectrophoresis (DEP) force. DEP is a phenomenon that occurs with a non-uniform electric field, in which an electrically neutral particle feels a force due to the interaction between the electric field and the particle's induced dipole moment. The direction of the DEP-induced particle motion depends on the particle's polarizability relative to the suspending medium, which in turn depends on the frequency of the applied electric field. The particles may move towards the higher electric field (called a positive DEP effect) or away from the field (negative DEP effect). Switching between positive and negative DEP can be achieved by adjusting the frequency of the electric field [Ahamed, 2018].

Typically a non-uniform electric field is generated in an fluidic device with interfacing regions of dielectric and conductive material. Electric field lines will locally concentrate at regions where conductive material narrows when interfacing with a dielectric material, as the electric field lines are more preferably present in the conductive material, as described by [Chou, 2002], in which the conductive material is a conductive solution within a fluidic device channel.

Figure 27:
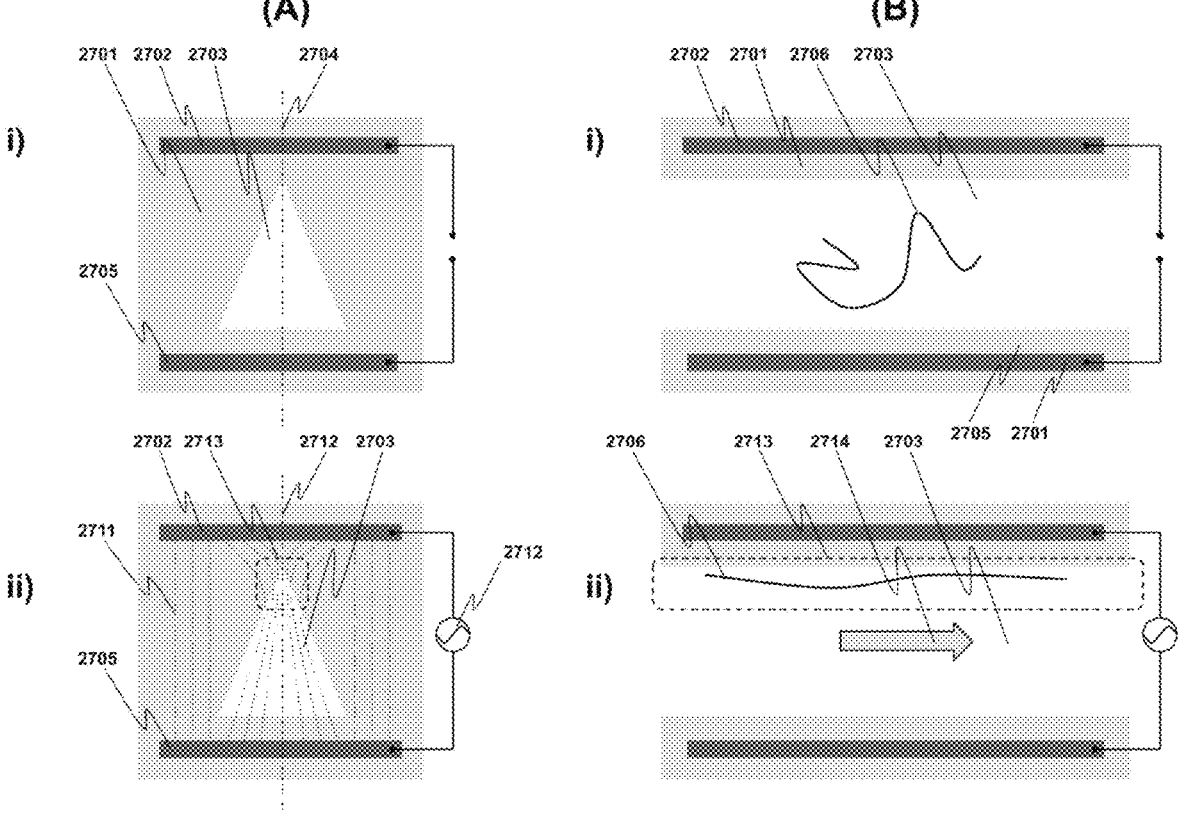
FIG. 27(A) illustrates a tapered channel for trapping and/or elongating a long nucleic acid molecule in a fluidic device in which i) the molecule is transported into the channel sandwiched by electrodes, and then ii) a DEP force is used to pull the molecule into the taper.
FIG. 27(B) is a cross-sectional view of FIG. 27(A).

FIG. 27 demonstrates an embodiment device and method for tuning the degree of elongation of a long nucleic acid molecule in a tapered fluidic channel, via the modulation of the DEP effect on a long nucleic acid molecule such that the nucleic acid is forced into the tapered region of the channel, and thus experiences a greater degree of confinement. The degree of nucleic acid elongation is directly related to the degree of physical confinement in which the nucleic acid resides [Reisner, 2005]. Here, the DEP force is tuned to push the nucleic acid molecule into a taper. The greater the DEP force on the molecule, the deeper into the taper the molecule will be pushed, which in turn increases the molecule's degree of physical confinement, elongation, and energy state (see definitions on Entropic traps). When the force is removed, the molecule relaxes to a lower energy state, and freely occupies the channel in a free coil formation. As such, the degree of confinement the molecule experiences can be adjusted by tuning the direction and magnitude of the DEP force on the molecule into the taper point.

In this embodiment, a tapered channel 2703 shown in FIG. 27(A) is defined in dielectric material 2701, with the channel sandwiched between two electrodes 2702 and 2705. In the preferred embodiment, within a cross-section of the channel, there is a taper, or point, that is substantially normal the electrodes, as shown in FIG. 27(A). FIG. 27(B) demonstrates a cross-section of the device shown in FIG. 27(A) through the drawn line 2704. Here, a long nucleic acid molecule 2706 is confined within the channel 2703, however the cross-sectional dimensions of the channel are sufficiently large that the molecule is unconstrained and free to form a random coil in solution. In some embodiments, the smallest confining dimension is at least 500 nm, or at least 1 micron, or at least 2 microns, or at least 5 microns, or at least 20 microns, or at least 50 microns.

When an oscillating electric voltage source 2712 is applied to the electrodes, electric field lines 2711 form between the electrodes within the device in a non-uniform fashion such that there is a concentration of the field lines at the taper region of the channel 2713. FIG. 27(B)(ii) shows a cross-section of the device shown in FIG. 27(A)(i) through the line defined by 2712. The oscillating electric field will induce a DEP force on the long nucleic acid molecule 2706 towards the taper point of the channel 2713. In addition to the DEP force acting on the molecule, an additional external force 2714 applied normal to the DEP force can be used to further manipulate the molecule.

Such an embodiment device and method allow for tunable elongation on demand. In one method, a long nucleic molecule may be identified as an object of interest via. After identification, the molecule is brought to rest, and then a DEP force is applied such that long nucleic acid molecule is pulled into the taper and elongated. In some embodiments, the process of elongating the molecule is aided with the application of an additional external force on the molecule, normal to the DEP force. In some embodiments, the polarity of the force is oscillatory. Confining the molecule within the taper allows for a tunable degree of elongation, and corresponding reduction in random thermal motion in the molecule, via the strength of the DEP force and narrowness of the taper point. In some embodiments, the taper point has a radius of 100 nm or less, or 75 nm or less, or 50 nm or less, or 25 nm or less, or 15 nm or less, or 10 nm or less.

In another embodiment method, such a device could be used to aid in the uncoiling of a long nucleic acid from a random coil configuration to at least a partially elongated state, as part of "preparation for interrogation". In another embodiment, such a device could be used to physically localize a macromolecule within a channel with an applied DEP force while in the presence of a fluid flow in the channel. This embodiment allows for reagent solution exchange around the molecule.

In another embodiment, the fluidic device is comprising of multiple DEP regions, each with its own electrode. The regions can share a common electrode, or have pairs of electrodes that are independent from other regions. In some embodiments, at least a subset of these regions can have their applied electric field independently controlled from another subset of regions.

There are many ways of manufacturing such a tapered channel device. In one embodiment, material is deposited on the top of an existing rectangular channel to generate a taper [Austin, 2001, Patent]. In another embodiment, a plasma assisted etch can be tuned to etch a substrate with a patterned mask, such that the resultant channels have sloped sidewalls. This process can be further optimized for various taper geometries by adding a deposition/passivation process with the etch, either simultaneously, or via cycling [Horowitz, 1989]. In another embodiment, the channels can be imprinted or embossed in a polymer, or polymer film using a tapered mold [Yu, 2004]. For example, a mold could be manufactured by wet etching a silicon substrate to expose the {111} crystal planes with a mask to generate long triangle-like gratings [Frühauf, 2005], which can then be transferred into a polymer via a molding process. Such a process allows for taper radius of 5 nm or less.

In some embodiments, the electrodes are integrated in the device. In some embodiments, at least one electrode is externally applied to the device.

Containing Macromolecules in Phase Shift Materials

In another set of embodiments, at least a portion of a body (eg: package or macromolecule) is contained within a phase-change material contained a fluidic device, such that the mobility of the body can be controllably reduced via the process of the material undergoing a transition. In some embodiments, the transition is reversible. In other embodiments, the transition is non-reversable.

It has been demonstrated previously that immobilizing biological bodies in a sol-gel material that has been gelled is an effective way of improving the resolution fluorescent microscopy imaging, due to the suppression of thermal noise [Lira, 2016]. In this set of embodiments, the phase-change material is contained within a region of a fluidic channel of a fluidic device and is used to reduce the mobility of the body at least partially within the phase-changed material. In some embodiments, a corresponding reduction in thermal noise with mobility reduction can be used to improve the resolution of the body when being interrogated. In some embodiments, the mobility reduction can be used to physically localize a body, such that it can be selected or sorted from a population. In some embodiments, the mobility reduction can be used as part of process to manipulate the physical shape or conformation of the body.

Phase-change materials have been used extensively in fluidic devices, however their application has largely been limited to mechanical manipulation of fluidic components, such as valves and fluid flow control. A summary is included for reference [Hilbar, 2016]. In this set of embodiments we are specifically interested in using these materials to reduce the mobility of various bodies, preferably packages and macromolecules, and thus a complete phase-change from liquid to solid is not a necessary requirement. In some embodiments, a partial transition, due to an incomplete phase-change and/or dilution of the material, is desired. In prior art, a phase-change material in a fluidic device was used as a fluid control mechanism [Wang, 2011], where-by the localized phase transition in the device must be near complete to a solid material to block fluid flow.

Different phase-change materials, and mechanisms to trigger their phase-change are possible. These include gel-sol materials that undergo a gel-sol transition with a temperature change. Preferable embodiments employ a sol-gel material that exhibits a hysteresis in its liquid-to-gel transition such that both the translocation of the biological body into the liquid state sol-gel, and the analysis when in a solid (semi-solid) state are at room temperature. Non-limiting example of such materials include agarose, K-carrageenan, xanthan-carob mixed gels, polysaccharide containing gels, and the gels described in [Hilbar, 2016]. With such an embodiment, the body can be translocated into the sol-gel material in a liquid state, the device is then cooled, transitioning the sol-gel material into a gel, and containing at least a portion of the body in the gel. Other possible phase-change materials include electro-rheological, electro-magnetic-rheological, and magnetic-rheological fluids which can undergo a liquid-solid phase change in the presence of a suitable electric and/or magnetic field [Dong, 2019]. In this embodiment, a region of the fluidic device containing the material, and at least a part of the body is exposed to an electric and/or magnetic field that changes the material's state from liquid to solid. The field can originate from any source, including electrodes or coils embedded within the device, or externally supplied. Non-limiting example materials include those listed by the included reference [Dong, 2019] and [Hilbar, 2016]. In the preferred embodiment, optically transparent materials are used, to allow for optical interrogation of the bodies within the material.

Other possible phase-change materials include photo-rheological liquids where-by the phase-change is initiated via exposure to light. Non-limiting examples include surfactants, salts, polymers, or small-molecule gelators that contain photo-responsive azobenzene, stilbene, spiropyran, or alginate moieties. [Kelly, 2020], [Raghavan, 2016]. Other possible phase-change materials include liquid-crystals.

Figure 28:
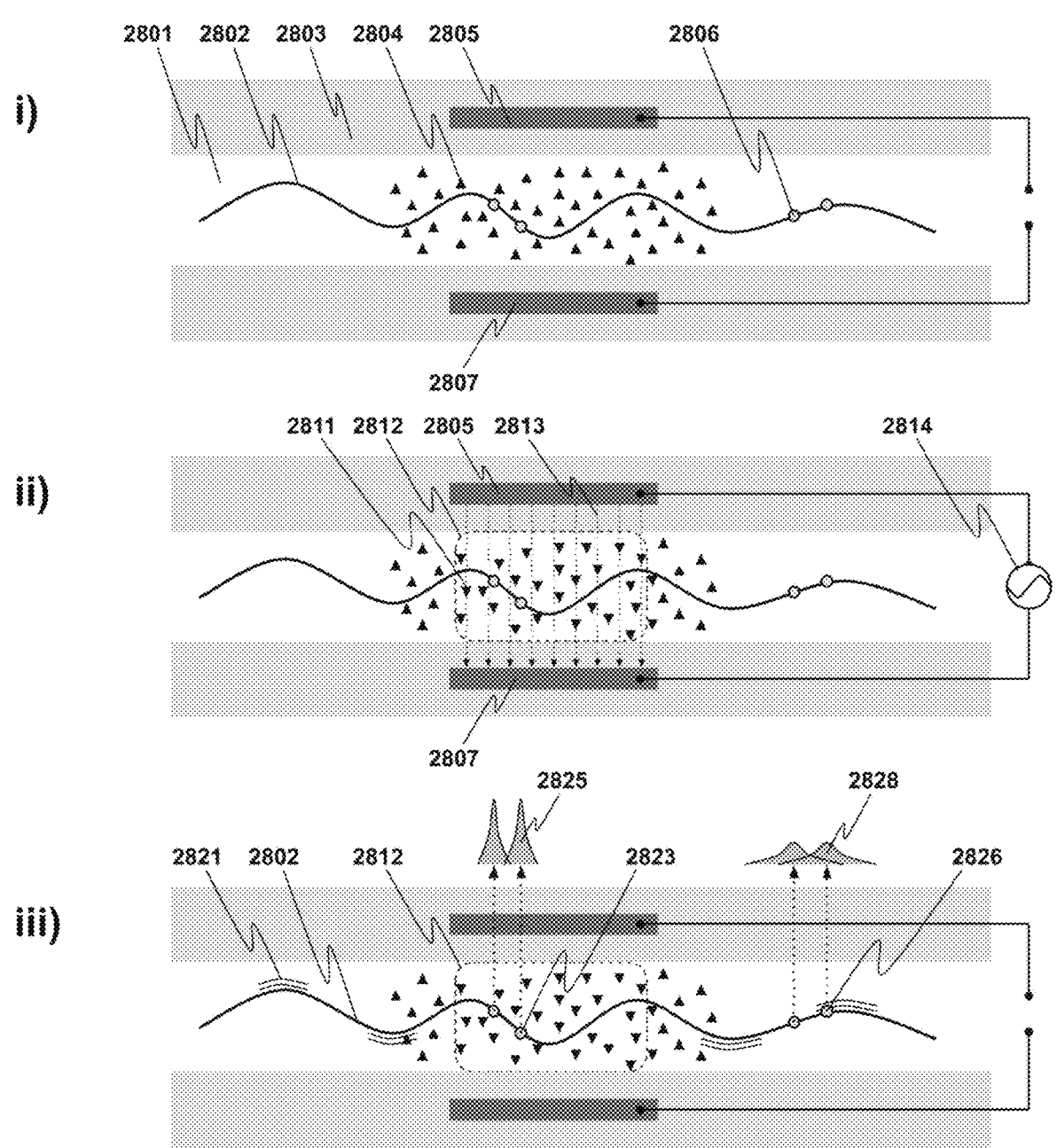
FIG. 28 illustrates a fluidic device with channel containing a phase-change material in which i) a long nucleic acid molecule is transported into the phase-change material, ii) the material undergoes a phase-change via the application of an applied electric field, and then iii) the localized mobility of the molecule in the phase-changed material is reduced.

FIG. 28 demonstrates an embodiment where-by a portion of a long nucleic acid molecule is contained with a phase-change material such that the local thermal noise can be reduced to improve resolution during interrogation. Here, a long molecule 2802, along which are fluorescent label bodies 2806 bound, is contained in a channel 2801 of a fluidic device 2803. Within the device are conductive electrodes 2805 and 2807 that sandwich the channel. Within the channel is an electro-rheological fluid 2804. When a region 2812 of the electro-rheological fluid is exposed to an electric field 2813 generated by an applied voltage 2814, the viscosity in that region increases due to a phase change 2811, and the localized random thermal motions are suppressed due to the localized reduction in mobility. When the molecule is fluorescently interrogated, the measured signal 2825 from labels 2823 within the region will have improve resolution than the measured signal 2828 from labels 2826 outside the region due to the higher degree of thermal noise 2821.

Two Labeling Body Type Scheme

In this set of embodiments, we describe a method of generating a physical map along the length of a long nucleic acid molecule using two different types of labeling bodies.

In one set of embodiments, a melt-map physical map is generated with a first labeling body type that specifically binds to double-strand nucleic acid, and a second labeling body type that specifically binds to single strand nucleic acid. Single labeling body melt-mapping has previously been shown to be an effective means of generating a physical map along the length of a long nucleic acid molecule. In this method the profile is generated by uniformly staining the molecule with an intercalating dye, and then selectively releasing the dye in certain regions of low CG concentrations by partially melting the DNA, thus generating a fluorescent signature along the length of the molecule (a linear physical map) that correlates with the underlying genomic content. The DNA is then fluorescently interrogated, and the physical map can be used to identify the molecule. There are limitations to this method. Firstly, after the intercalating dye has been shed off the AT rich regions, the dye can re-bind to the AT rich regions once the DNA has returned to its fully double-strand state. Thus, care must be taken when implementing the labeling protocol to ensure the fidelity of the physical map. Secondly, the measured fluorescent analog signal along the length of the imaged molecule's major axis contains a significant amount of ambiguity with regards to differentiating between the signal modulating due to AT/CG variation along the length of the major axis, or due to the nucleic acid density variation along the length of the major axis.

Here we describe an embodiment method of using two different labeling body types to resolve these issues. The first labeling body type binds non-specifically to a double strand nucleic acid molecule, while the second labeling body type binds non-specifically to a single-strand nucleic acid molecule. For embodiments where-by the interrogation system is a constriction device, such a nanopore, where-by the signal measured is the current blockade through the pore, or tunnel current across the pore, as the nucleic acid molecule translocates through the pore, the two labeling body types need not be fluorescent, as their physical conformation when bound to the nucleic acid will generate a signal. Rather, in the preferred embodiment, the two labeling body types have a different physical conformation when bound to the nucleic acid so at to generate a unique current blockage signal. For embodiments where-by the interrogation system is a fluorescent imaging system, and the long nucleic acid molecule is interrogated when at least a portion of the molecule is in an elongated state in a fluidic channel of a fluidic device, or combed on a surface of substrate or fluidic device, at least one labeling body type generates a fluorescent signal. In the preferred embodiment, both labelling body types generate a fluorescent signal, where each type has a different emission wavelength, or a different excitation wavelength.

In some embodiments, the first labeling body type that binds to double strand nucleic acid may be selected from a group of different cyanine fluorescent dyes, which may be obtained from Invitrogen (www.invitrogen.com) such as TOTO-1™ and YOYO-1™ (1,1'-(4,4,8,8,-tetramethyl-4,8-diazaundecamethylene)bis[4-[3-methyl-benzo-1,3-oxazol-2-yl]methylidene]-1,4-dihydroquinolinium] tetraiodide). More examples from Invitrogen include POPO-1™, BOBO-1™, JOJO-1™, POPO-3™ LOLO-1™, BOBO-3™, YOYO-3™ and TOTO-3™.

In some embodiments, the second labeling body type that binds to single-strand nucleic acid may be a single-strand binding protein. In some embodiments, the single-strand binding protein is modified to include a fluorescent label. In some embodiments, modified single-strand binding protein is Alexa Fluor 488 (AF488SSB) or 546 (AF546SSB) dye. In some embodiments, the single-strand binding protein is a replication protein, or a modified variant of a replication protein A (RPA). In some embodiments, the RPA is modified to include a fluorescent tag. In some embodiments, the second labeling body type includes any one of the following: QuantiFluor, SYBR Green II, OliGreen. In some embodiments, the second label body type is a nucleic acid binding body capable of hybridizing.

Figure 29:
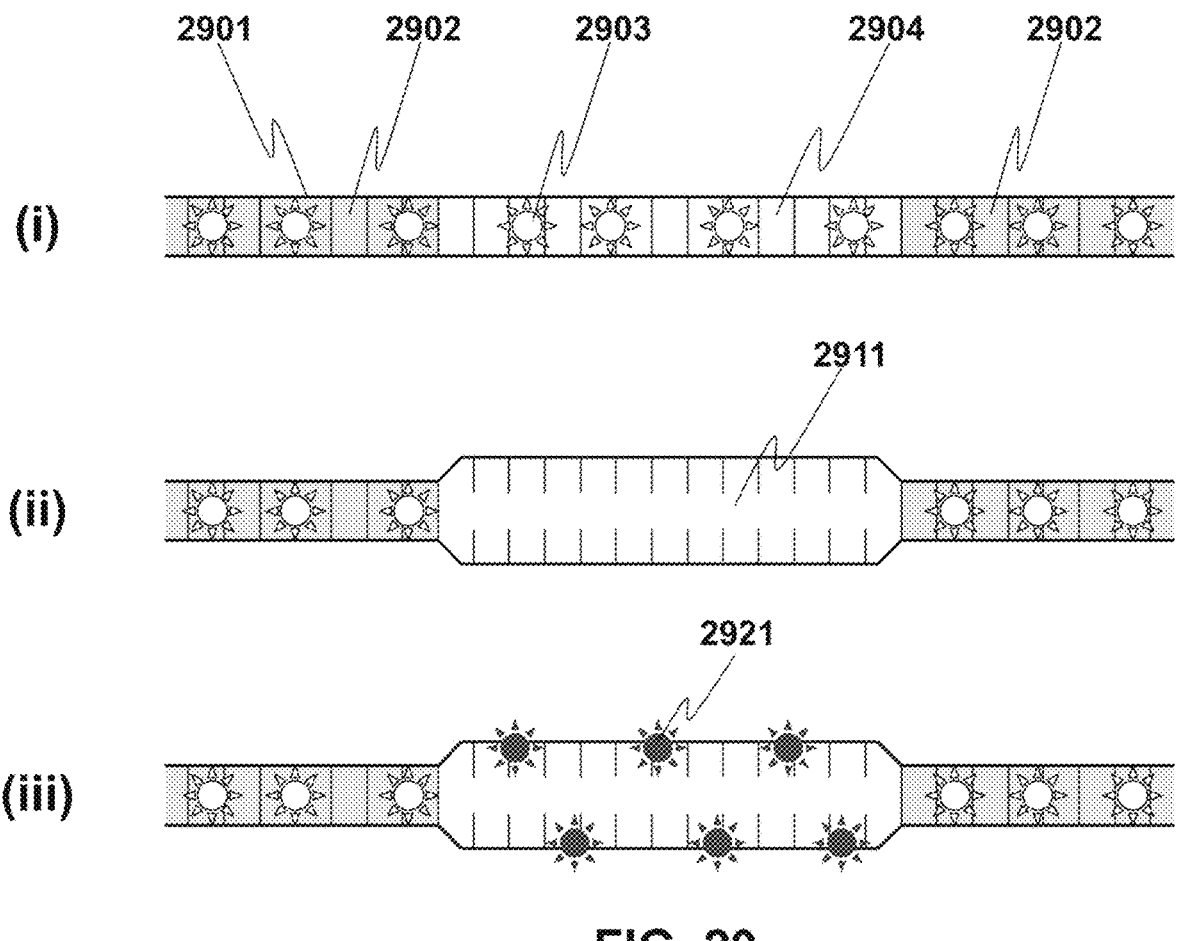
FIG. 29 illustrates a method for generating a differential two color AT/CG density linear physical map on a long nucleic acid molecule, in which i) the molecule is non-selectively labeled with a double-stranding binding labeling body of color 1, ii) the molecule is partially melted, releasing the labeling bodies in the AT rich regions, and iii) a single-strand labeling body of color 2 is bound.

In one embodiment for labeling the long nucleic acid, described in FIG. 29, first the fully-natured molecule 2901 is non-selectively bound to the first labeling body type 2903, such that both CG rich regions 2902 and AT rich regions 2904 are uniformly bound to. Next, the molecule is exposed to conditions that partially de-nature (2911) the molecule as described previously [Tegenfeldt, 2008, U.S. Pat. No. 10,434,512]. While the molecule is in a partially de-natured state, the second labeling body type 2921 is bound to the exposed single strands. Finally, the molecule is returned to environmental conditions that favor the molecule being fully-denatured. However, due to the presence of the single-strand labeling bodies in the AT rich regions, said labeling bodies will restrict the molecule from returning to a fully natured (double-strand) state in the AT rich regions, and as a consequence the first labeling body will be less likely to re-bind in these regions, thus maintaining the fidelity of the labeling pattern.

In another embodiment for labeling the long nucleic acid, the molecule is first exposed to conditions that partially de-nature the molecule. While the molecule is in a partially de-natured state, the second labeling body type is bound to the exposed single strands. The molecule is then returned to environmental conditions that favor the molecule being fully-natured, and the first labeling body type is bound to the double-strand DNA. However, due to the presence of the single-strand labeling bodies in the AT rich regions, said labeling bodies will restrict the molecule from returning to a fully natured (double-strand) state in the AT rich regions, and as a consequence the first labeling body will be less likely to bind in these AT rich regions, thus maintaining the fidelity of the labeling pattern.

In the preferred embodiment, the first and second type of labelling bodies are both fluorescent, each with a different emission wavelength, or a different excitation wavelength, such that a differential two color physical map can be generated. Here we describe an embodiment method of using two different colors that selectively identify the AT and CG rich regions to overcome some challenges of the single-color physical maps that correlate with AT/CG linear density (eg: melt map, competitive binding). With just a single color physical AT/CG map, the map is ambiguous if a variation in fluorescent signal along the length of the long nucleic acid molecule's major axis is due to variation in AT/GC content, or localized variation in the molecule's stretch (eg: localized nucleic acid density). Furthermore, dark regions along the length of the molecule may be due to high AT content or two molecules adjacent to each other with a space between. These ambiguities can be overcome by employing two colors to generate a differential signal, such that the variation in stretch can be corrected for. For example, if there is an increase in one color C1 (the first labeling body type that is associated with regions of CG content), this may be due to localized higher nucleic acid density of the molecule in the fluorescent image (eg: a compression, a fold, a knot), or an enrichment in CG content. By employing a secondary color C2 (the second labeling body type that is associated with regions of AT content) the ambiguity can be resolved. A localized compression of the molecule will result in an increase in both the measured C1 and C2 at that spatial location, while a localized CG enrichment would result in an increase in measured C1, and a decrease in C2. Furthermore, the end of molecules can be unambiguously identified by the lack of both colors.

Figure 30:
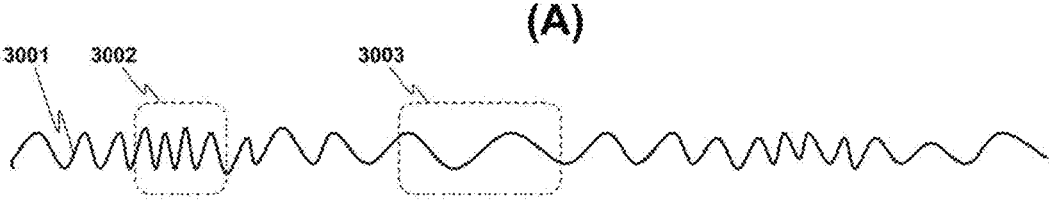
FIG. 30(A) illustrates an elongated long nucleic acid molecule with variable nucleic acid density along the length of the molecule's major axis.
FIG. 30(B) is a schematic of the variation in measured signal of color-1 and color-2 from the molecule of FIG. 30(B).
Figure 30:
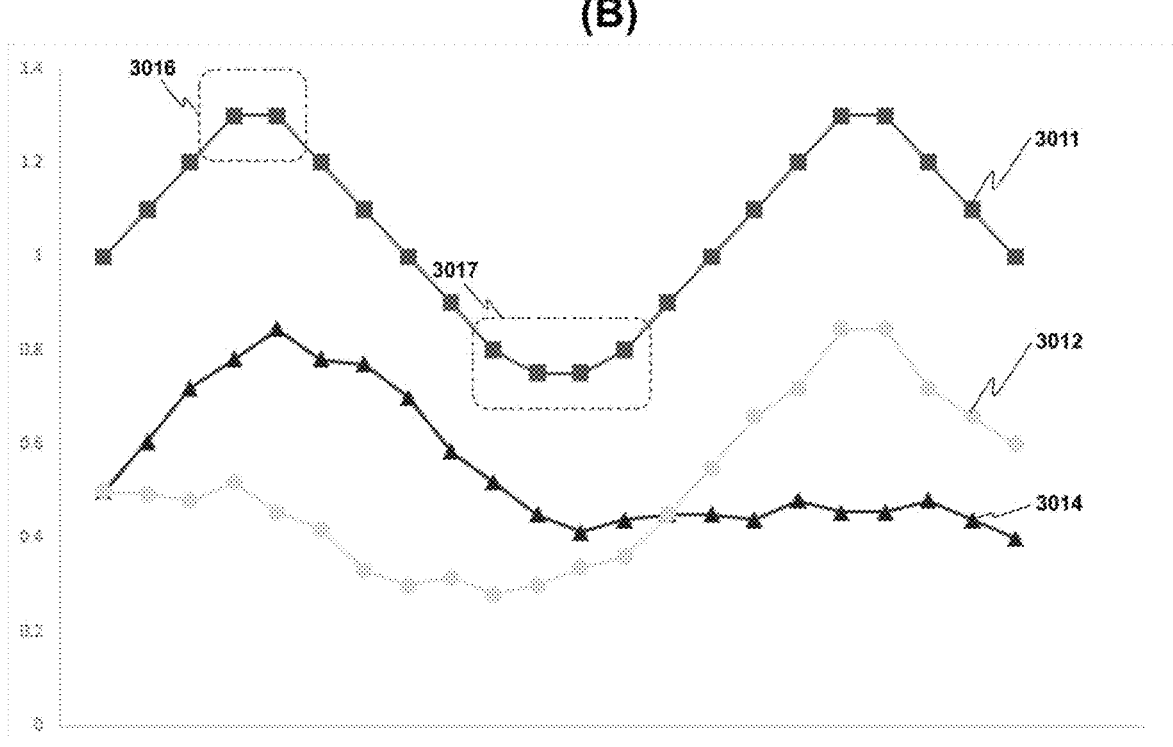

FIG. 30 demonstrates an embodiment method of interpreting the two-color AT/CG density physical map from a long nucleic acid molecule that is fluorescently interrogated while in an elongated state. FIG. 30(A) shows an elongated molecule 3001 where-by there is a variation in nucleic acid density along the major axis of the molecule. In this example, the variation in density is due to variation in stretch, such in some regions along the major axis, the molecule is more compressed and has a higher linear density 3002, while in other regions, the molecule is less compressed, and has a lower linear density 3003. FIG. 30(B) shows a plot of the measured fluorescent signal values along the length of the molecule's major axis (assuming for this example a simple model of signal linearity from each labeling body). Here, 3012 is the normalized (to 0.5) signal from labeling body type 1, 3014 is the normalized (to 0.5) signal from labeling body type 2, and 3011 is the summation of the two signals. In this simple model example, the summation of the two signals would result in a constant normalized value of 1 if the molecule had uniform linear density along the major axis. In other embodiments, a calibration curve would be generated, through experiment or simulation, that provides the expected value of the summation of the normalized signals, given a constant linear density. The summation curve 3011 is then used to generate a map of the molecule's linear nucleic acid density along the length of the molecule's major axis, indicating regions of high density 3016, and low density 3017. Such a map can then be used to correct the interpreted physical map of the molecule, to provide a more accurate estimate of molecule's AT/CG density along the genomic sequence in base-pairs.

Another embodiment method to generate a differential signal physical map along the length of a long nucleic acid molecule is to use competitive binding [Nyberg, 2012] where-by the two labeling body types each have a different emission wavelength, or different excitation wavelength. In this method, the first labelling body type will out-compete the second labeling body type to bind to AT rich regions, while the second labeling body type will out-compete the first to bind to CG rich regions, while the entirety of the molecule remains in a fully natured (double-stranded) state.

In another embodiment method to reduce the ambiguities associated with variation in linear nucleic acid density along the major axis of an elongated long nucleic acid molecule when being fluorescently interrogated is to reduce the impact of speckle from the fluorescent illumination system. The speckle effect is a result of the interference of many waves of the same frequency, having different phases and amplitudes, which add together to give a resultant wave whose amplitude, and therefore intensity, varies randomly. When using a coherent laser source to illuminate a fluorescent sample, this can be a source of noise [Deschamps, 2006], and as such various techniques have been developed to manage this noise including modulators, and multi-mode fibers. In many fluorescent imaging applications, speckle is not a significant source of noise to warrant attention. This is particularly true for applications where-by the signal is an isolated fluorescent molecule. However, when multiple fluorescent molecules are brought in close proximity together, far below the diffraction resolution limit, the single becomes a continuum. In some applications, for example AT/CG density physical maps, the modulation of this continuum along the length of the molecule provides useful information, and here speckle is significant source of noise. Suppression of speckle can be accomplished either via using a non-coherent light source such as LEDs, halogen lamps, mercury lamps, etc, or by suppressing the speckle from a coherent light source, such as fibers, oscillating windows.

Applications—Telomere Analysis

Telomere analysis is one application of the systems, compositions and methods disclosed herein. Telomeres are common eukaryotic genetic features of specialized protein-DNA constructs present at the ends of linear chromosomes (At the very 3'-end of the telomere a 300 bps overhang called T-loop, maintained by several proteins called the shelterin complex, consists of six proteins identified as TRF1, TRF2, TIN2, POT1, TPP1, and RAP1), which prevent them from easy progressive degradation during replications and ensure the integrity of linear chromosomes by preventing end-to-end chromosomal fusion. Most vertebrate telomeric DNA consists of long (TTAGGG) n repeats of variable length, often around 3-20 kb. As the cell divides the telomeres on the end of the chromosome eventually get smaller (DNA in cultured human cell is shortened by 50-100 base pairs per cell division), acting as a sort of time-delay "fuse", or measurement of somatic cell aging, eventually running out after a certain number of cell divisions (average 50 and 70 times) and resulting in normal senescence/cell death due to the eventual loss of vital coding genetic information further behind the termini of linear chromosomes. Unless in germ line and cancer cells, an active enzyme telomerase, would maintain the elongation of the telomeres causing the cells to be very long-lived.

Telomeres are critical for maintaining genomic integrity and may be factors for age-related diseases. telomere dysfunction or abnormal shortening can lead to genomic instability, chromosome loss and the formation of non-reciprocal translocations commonly acquired due process of somatic cellular aging, psychosocial and oxidative stress and tumor development. Telomeres in tumor cells and their precursor lesions are significantly shorter than surrounding normal tissue.

Subtelomeres are segments of DNA between two telomeric end caps and chromatin, the most distal (farthest from the centromere) region of unique DNA on a chromosome, and they are unusually dynamic and variable mosaics of multichromosomal blocks of sequence, sometimes spanning 100s of kilobases. The subtelomeric regions are structural variation hotspots enriched with chromosomal rearrangement and copy number variations, such as long segmental duplications, tandem or interspersed repeats, often implicated in disorders like facioscapulohumeral muscular dystrophy (FSHD), Alzheimer's disease, and peculiar syndromic diseases (malformation and mental retardation), as well as important functions in immunity.

Genomic analysis, especially sequencing and profiling of patient telomeric and subtelomeric regions, is difficult because of the end locations, repeated sequences, length of stretches, and lack of databases on the topic. Some current methods are mostly "estimation" technologies with indirect, inference based approach, based on averaged bulk solution samples.

So capability to directly monitor and characterize chromosomal ends and sub regions in their native genomic and epigenomic context, especially at single cell and single molecule level, are highly desirable and of critical biological and medical value in cancer, stem cell research, wellness and aging/longevity field.

In one application embodiments, the capability to precisely identify in the genome through physically mapping, the location, type of de novo or inherited large changes intractable by sequencing alone, to directly measure the physical length of the telomeres, at single molecule/chromosome and/or single cell level, directly image and measure the features and patterns of telomeric and subtelomeric regions in the context of sequence coding, chemical moiety modification or protein binding or physical folding, analyze and correlate these variant loci data, influencing or altering the biological or pathological consequences, in the context of other existing functional, regulatory, or structural genomic content, to reach diagnostic, prognostic or identifying actionable drug target for DNA damaging, lesions, cellular aging progress, or cancer progress for guidance of wellness management or development of therapeutics strategies.

For example, it is becoming apparent that reversing shortening of telomeres through temporary activation of telomerase may be a potent means to slow aging. Three routes have been proposed to reverse telomere shortening: drugs, gene therapy, or metabolic suppression, so-called torpor/hibernation. Techniques to extend telomeres could be useful for tissue engineering, because they might permit healthy, noncancerous mammalian cells to be cultured in amounts large enough to be engineering materials for biomedical repairs.

Wellness and longevity industry has growing rapidly as a 17-trillion dollar market to reach 27 trillions in 2026. The Longevity industry will dwarf all other industries in both size and market capitalization, reshape the global financial system, and disrupt the business models of pension funds, insurance companies, investment banks, and entire national economies.

An example of subtelomeric disorder, FSHD is associated with a deletion in the subtelomeric region of chromosome 4q. A series of 10 to >100 kb repeats is located in the normal 4q subtelomere, but FSHD patients have only 1-10 repeat units. This deletion is thought to cause disease owing to a position effect that influences the transcription of nearby genes, rather than through the loss of the repeat array itself.

A top down visualization technology tool able to visualize the event is very useful to allow the further isolation and dissemination of the variant copy numbers, location, exact fusion point, and its influence of the adjacent genes for diagnosis and therapeutics.

Numbered Aspects of the Disclosure Herein

The disclosure is further elucidated through reference to the following numbered aspects of the embodiments herein. 1. A fluidic device composed of patterned surface features or patterned surface energies that allows for the arrangement of at least two macromolecules originating from a single package for interrogation such that the probability of said two macromolecules overlapping each other is reduced, when compared to a similar device without said patterned surface features. 2. The device of any of the above aspects, wherein the at least two macromolecules are delivered to the device within said package. 3. The device of any of the above aspects, wherein the package can be any of the following: cell, nucleus, vesicle, droplet, mitochondria, organelle. 4. The device of any of the above aspects, wherein the sample solution contains a lysing agent. 5. The device of any of the above aspects, wherein the package is partially ruptured. 6. The device of any of the above aspects, wherein the package is in an over-pressurized state. 7. The device of any of the above aspects, wherein the package is in a hypotonic state. 8. The device of any of the above aspects, wherein the at least two macromolecules arranged on the surface of the device are immobilized. 9. The device of any of the above aspects, wherein the at least two macromolecules are long nucleic acid molecules. 10. The device of any of the above aspects, wherein the at least two long nucleic acid molecules at least partially comprising any of the following: at least a portion of a chromosome, chromosomes in metaphase, chromosomes in interphase, chromatin native nucleic acid with cellular proteins bound. 11. The device of any of the above aspects, wherein said at least two long nucleic acid molecules are at least partially elongated. 12. The device of any of the above aspects, wherein the major axis of elongation is substantially parallel to the major axis of the patterned surface features and/or pattern surface energies. 13. The device of any of the above aspects, wherein the at least two long nucleic acid molecules are each bound to by at least two labeling bodies. 14. The device of any of the above aspects, wherein the at least two labeling bodies on the long nucleic acid molecule are comprising a physical map. 15. The device of any of the above aspects, wherein the physical map is a linear physical map. 16. The device of any of the above aspects, wherein the physical map is a 2D physical map. 17. The device of any of the above aspects, wherein by the physical map is a 3D physical map. 18. The device of any of the above aspects, wherein the binding of at least two labeling bodies is done prior to introduction of the long nucleic acid molecule to the device. 19. The device of any of the above aspects, wherein the binding of at least two labeling bodies is done after the long nucleic acid molecule is introduced to the device. 20. The device of any of the above aspects, wherein the labeling body is comprising any of the following: A nucleic acid stain or dye, a double-strand nucleic acid stain or dye, a single-strand nucleic acid stain or dye, a karyotyping stain or dye, an AT specific stain or dye, an intercalating dye, a CG specific stain or dye, a FISH probe, a fiber-FISH probe, a methylation fluorescent probe, a fluorescently modified nucleotide, an incorporated fluorescently modified nucleotide, a guiding RNA fluorescent probe, a sequence specific fluorescent probe, a physical mapping labeling body, a linear physical mapping labeling body, a 2D physical mapping labeling body, a 3D physical mapping body, a telomere stain, a fluorescently modified DNA or RNA binding enzyme, a fluorescently modified CRISPR complex, a fluorescent modified DNA or RNA binding agent, a fluorescently modified single-strand DNA binding body. 21. The device of any of the above aspects, wherein the at least two macromolecules are exposed to any of the following, or combinations there-of: a reagent, a solution, a solvent, a temperature change, a humidity change, a centrifugal force, a pressure change, a vapor, an external force, an ultrasonic force, a dispensing system, a contact probe. 22. The device of any of the above aspects, wherein the ultrasonic is used to assist in any of the following, or combination there-of: lysing packages, separating chromosomes, separating long nucleic acid molecules, elongating long nucleic acid molecules, shearing long nucleic acid molecules. 23. The device of any of the above aspects, wherein the macromolecule is arranged within the device's patterned surface features or patterned surface energies via deposition from a receding meniscus of solution over said patterned features or patterned surface energies. 24. The device of any of the above aspects, wherein the direction and/or speed of the receding meniscus is at least partially influenced by the patterned surface features or patterned surface energies. 25. The device of any of the above aspects, wherein the direction and/or speed of the receding meniscus is at least partially influenced by gravity. 26. The device of any of the above aspects, wherein the direction and/or speed of the receding meniscus is at least partially influenced by a capillary force. 27. The device of any of the above aspects, wherein a macromolecule contained within a package in the solution is lysed during the process of deposition. 28. The device of any of the above aspects, wherein the defined features are comprising at least one channel, or at least wall, or at least one pit, or at least one pillar on the surface of the device. 29. The device of any of the above aspects, wherein the surface of the most topologically prominent features are hydrophobic. 30. The device of any of the above aspects, wherein the macromolecules are arranged within the device's patterned surface features or patterned surface energies via capillary driven solution flow. 31. The device of any of the above aspects, wherein the direction or speed of the capillary flow is at least partially influenced by the patterned surface features or patterned surface energies. 32. The device of any of the above aspects, wherein the direction or speed of the capillary flow is at least partially influenced by at least one capillary pump. 33. The device of any of the above aspects, wherein the device is comprising at least one CRV. 34. The device of any of the above aspects, wherein there is at least one confining channel defined such that along at least one dimension of the channel, the dimension length is confining to at least one package. 35. The device of any of the above aspects, wherein the confining dimension of the channel is less than 95% the package's length along the major axis when un-confined and suspended in solution. 36. The device of any of the above aspects, wherein at least one entropic trap is patterned within said channel. 37. The device of any of the above aspects, wherein the volume of the entropic trap is 150% or less the volume of the package. 38. The device of any of the above aspects, wherein there is at least one confining channel defined such that along at least one dimension of the channel, the dimension length can be modulated to reduce the confining dimension to 95%, or less, the package's length along the major axis. 39. The device of any of the above aspects, wherein the modulation is via an external compressive force on the device, applied at designated locations. 40. The device of any of the above aspects, wherein the modulation is used to lyse the package. 41. The device of any of the above aspects, wherein the smallest patterned surface feature or patterned surface energy dimensional length that is substantially parallel to a 2D plane that is substantially normal to the optical axis of interrogation is 10 microns. 42. The device of any of the above aspects, wherein the smallest patterned surface feature or patterned surface energy dimensional length that is substantially parallel to a 2D plane that is substantially normal to the optical axis of interrogation is 2 microns. 43. The device of any of the above aspects, wherein the smallest patterned surface feature or patterned surface energy dimensional length that is substantially parallel to a 2D plane that is substantially normal to the optical axis of interrogation is 0.5 microns. 44. The device of any of the above aspects, wherein the smallest patterned surface feature or patterned surface energy dimensional length that is substantially parallel to a 2D plane that is substantially normal to the optical axis of interrogation is 0.1 microns. 45. The device of any of the above aspects, wherein the smallest patterned surface feature or patterned surface energy dimensional length that is substantially parallel to the optical axis of interrogation is 10 microns. 46. The device of any of the above aspects, wherein the smallest patterned surface feature or patterned surface energy dimensional length that is substantially parallel to the optical axis of interrogation is 2 microns. 47. The device of any of the above aspects, wherein the smallest patterned surface feature or patterned surface energy dimensional length that is substantially parallel to the optical axis of interrogation is 0.5 microns. 48. The device of any of the above aspects, wherein the smallest patterned surface feature or patterned surface energy dimensional length that is substantially parallel to the optical axis of interrogation is 0.1 microns. 49. The device of any of the above aspects, wherein the types of interrogation is comprising any of the following, or combinations there-of: electro-magnetic, fluorescent, confocal, TIRF, epifluorescence, brightfield, darkfield, AFM, SPM, TEM, SEM. 50. The device of any of the above aspects, wherein the form-factor is compatible with a standard microscope slide. (approximately 75×25 mm, or 3"×1"). 51. The device of any of the above aspects, wherein the device is comprising an integrated cover-slip. 52. The device of any of the above aspects, wherein a solution containment well for sample application to the device can be applied and/or removed by the user. 53. The device of any of the above aspects, wherein the patterned surface features are comprising channels, pillars, pits, grooves, mounds, corners, grids, walls, lines, pads, monolayers, topological changes, patterns of defined surface energy or charge. 54. The device of any of the above aspects, wherein the patterned surface features can be manufactured with any of the following methods, or combinations there-of: lithography, embossing, injection-molding, 3D printing, nanoimprint, ELB, photolithography, stamping, etching, plasma etching, wet etching, physical etching, lamination, bonding, transfer printing, printing, inkjet printing, dip-pen-lithography, deposition, self-assembly 55. The device of any of the above aspects, wherein the patterned surface energies can be formed by any of the following, including combinations there-of: material selection, surface treatment (liquid, vapor, UV, and/or plasma, deposition, selective agent binding), transfer printing monolayer. 56. The device of any of the above aspects, wherein the material composition of the device comprises any of the following, including combinations thereof: plastic, glass, silicon, elastomers, PDMS, COC, Topaz, PC, PS, silicon, silicon oxide, silicon nitride, borofloat, quartz, fused silica. 57. A fluidic device comprising: (i) A sample loading channel for receiving a sample solution containing at least one package suspended in solution, said package containing at least two macromolecules: (ii) At least one capture site for capturing a single package: (iii) At least one reaction chamber in fluidic connection with at least one capture site: (iv) At least one fluidic connection point in fluidic connection with the at least one reaction chamber through an entropic barrier, said barrier defined with respect to said macromolecules occupying the said reaction chamber. 58. The device of any of the above aspects, wherein preparing a macromolecule for interrogation is comprising any of the following: exposing the least one macromolecule in the reaction chamber to a reagent, a temperature, a pressure, a solvent, or combination there-of. 59. The device of any of the above aspects, wherein the reagent is comprising any of the following: enzymes, labeling bodies, DNA barcodes, PCR primers, PCR primers with barcodes, MDA primers, universal primers, DNA binding agent, DNA binding proteins. 60. The device of any of the above aspects, wherein the labeling body is comprising any of the following: A nucleic acid stain or dye, a double-strand nucleic acid stain or dye, a single-strand nucleic acid stain or dye, a karyotyping stain or dye, an AT specific stain or dye, an intercalating dye, a CG specific stain or dye, a FISH probe, a fiber-FISH probe, a methylation fluorescent probe, a fluorescently modified nucleotide, an incorporated fluorescently modified nucleotide, a guiding RNA fluorescent probe, a sequence specific fluorescent probe, a physical mapping labeling body, a linear physical mapping labeling body, a 2D physical mapping labeling body, a 3D physical mapping body, a telomere stain, a fluorescently modified DNA or RNA binding enzyme, a fluorescently modified CRISPR complex, a fluorescent modified DNA or RNA binding agent, a fluorescently modified single-strand DNA binding body. 61. The device of any of the above aspects, wherein the reagent is comprising a protein or nucleic acid digestive enzyme. 62. The device of any of the above aspects, wherein preparing a macromolecule for interrogation is comprising exposing at least one macromolecule in the reaction chamber to at least one external force. 63. The device of any of the above aspects, wherein the at least one external force is applied to the at least one macromolecule when said molecule is in the presence of at least one physical obstacle, a porous medium, a gel, or at least one entropic trap. 64. The device of any of the above aspects, wherein the at least one entropic trap is sized to accommodate a single macromolecule, and only a single macromolecule. 65. The device of any of the above aspects, wherein preparing a macromolecule for interrogation is comprising transporting via an external force at least a portion of said macromolecule into a region of increased confinement. 66. The device of any of the above aspects, wherein the region of increased confinement has a dimension parallel to the axis of optical interrogation that is 95% or less the length of the macromolecule's major axis. 67. The device of any of the above aspects, wherein preparing a macromolecule for interrogation is comprising positioning at least one portion of said macromolecule in a region of the device where-by at least one dimension that can be reversibly adjusted to decrease said dimension. 68. The device of any of the above aspects, wherein the dimension is parallel to the axis of optical interrogation. 69. The device of any of the above aspects, wherein the dimension can be reduced to at least 95% or less the length of the macromolecule's major axis. 70. The device of any of the above aspects, wherein the adjusted dimension is via at least one flexible wall of a fluidic channel within the fluidic device that can adjust its relative position to another wall within the same fluidic channel. 71. The device of any of the above aspects, wherein the adjusted dimension is via at least one wall of a fluidic channel within the fluidic device comprising at least partially of a phase-transition material that can adjust its relative position to another wall within the same fluidic channel due to some stimulus. 72. The device of any of the above aspects, wherein the adjusted dimension is via an application of an electrostatic attractive force between two opposing walls in a fluidic channel. 73. The device of any of the above aspects, wherein the electrostatic attractive force is generated via a time-varying electric field. 74. The device of any of the above aspects, wherein preparing a macromolecule for interrogation is comprising positioning at least one portion of said macromolecule in an electrowetting device. 75. The device of any of the above aspects, wherein preparing a macromolecule for interrogation is comprising applying a dielectrophoretic (DEP) force on at least one portion of said macromolecule. 76. The device of any of the above aspects, wherein an instrument controller modulates its interfaces with said fluidic device at least partially based on a feedback system, said feedback system having at least one input being data originating from the interrogation of at least one macromolecule. 77. The device of any of the above aspects, wherein at least one macromolecule is bound to at least two labeling bodies. 78. The device of any of the above aspects, wherein the at least two labeling bodies are comprising a physical map on the macromolecule. 79. The device of any of the above aspects, wherein the physical map is a linear physical map. 80. The device of any of the above aspects, wherein the physical map is a 2D physical map. 81. The device of any of the above aspects, wherein the physical map is a 3D physical map. 82. The device of any of the above aspects, wherein the physical map can be generated from any of the following methods, or combination there-of: melt-mapping, differential mapping, competitive binding, labeled nick sites, bar-coding, methylation mapping, methyl-transferase mapping, sequence specific binding, chemical moiety binding, anti-body, CRISPR-Cas and derivatives from modified enzymes. 83. The device of any of the above aspects, wherein the physical map is comprising karyotyping Q-bands. 84. The device of any of the above aspects, wherein the dyes used is comprising one of the following: quinacrine, Hoescht 33258, Hoechst 33342, DAPI (4',6'-diamidino-2-phenylindole) and diimida-zolinophe-nylindole (DIPI), daunomycin. 85. The device of any of the above aspects, wherein the physical map is comprising karyotyping G bands. 86. The device of any of the above aspects, wherein the dyes used is comprising one of the following, or combination there-of, but not limited to: Giemsa, Wright, and Leishman. 87. The device of any of the above aspects, wherein the physical map is comprising karyotyping R bands. 88. The device of any of the above aspects, wherein the dyes used is comprising one of the following, or combination there-of, but not limited to: chromomycin A3, olivomycin, mithramycin, 7-amino actinomycin D. 89. The device of any of the above aspects, wherein the physical map is comprising karyotyping C bands (heterochromatin density). 90. The device of any of the above aspects, wherein the physical map identifies sister chromatids. 91. The device of any of the above aspects, wherein the process of labeling the macromolecule with labeling bodies is at least in part controlled by the control instrument using a feedback system to optimize the signal contrast of the physical map. 92. The device of any of the above aspects, wherein the at least one macromolecule is collected after interrogation based at least partially on the results of said interrogation. 93. The device of any of the above aspects, wherein a portion of the macromolecule, consisting of a long nucleic acid molecule, is at least partially elongated in an elongation channel, and at least a portion of the said portion is interrogated. 94. The device of any of the above aspects, wherein said elongated portion is comprising a linear physical map. 95. The device of any of the above aspects, wherein said portion is physically connected to the macromolecule during interrogation. 96. The device of any of the above aspects, wherein said portion is physically disconnected from the macromolecule before or during interrogation. 97. The device of any of the above aspects, wherein said portion is selected for interrogation based on its originating location within the macromolecule. 98. The device of any of the above aspects, wherein the elongation channel has a confining dimension that is parallel to the optical axis of interrogation, and is 100 nm or less. 99. The device of any of the above aspects, wherein the macromolecule can be any of the following, but not limited to: Chromosomes, Chromosomes in or near metaphase, Chromosomes in or near Interphase, Extra chromosomes, ecDNA, Segments of Chromosomes, long nucleic acid molecules, chromatin. 100. The device of any of the above aspects, wherein by two packages can be sequentially interrogated in the same reaction chamber by first flushing the first package's contents from the chamber before loading the second package's contents. 101. The device of any of the above aspects, wherein at least one package to be interrogated is selected via selectively lysing said at least one package while said package is in a capture site. 102. The device of any of the above aspects, wherein the selective lysing is implemented by the selective application of any of the following, or combinations there-of, to the package: photo-lysing, flow of lysate agent, heat, acoustic energy, ultrasonic energy, electric field. 103. The device of any of the above aspects, wherein the selection criteria can be any of the following, or combinations there-of: package size, package shape, presence or absence of marker on the package. 104. The device of any of the above aspects, wherein multiple fluidic reaction chambers are in fluidic connection with each other via entropic barriers. 105. The device of any of the above aspects, wherein the entropic barrier to the macromolecule presents a confining dimension that is 95% or less the length of the molecule's major axis. 106. The device of any of the above aspects, wherein the interrogation region and reaction chamber are one of the same. 107. The device of any of the above aspects, wherein the interrogation region area measured in a plane substantially normal to the optical axis of interrogation is at least as large as 100000 microns squared. 108. The device of any of the above aspects, wherein the interrogation region area measured in a plane substantially normal to the optical axis of interrogation is at least as large as 10000 microns squared. 109. The device of any of the above aspects, wherein the interrogation region area measured in a plane substantially normal to the optical axis of interrogation is at least as large as 1000 microns squared. 110. The device of any of the above aspects, wherein the interrogation region area measured in a plane substantially normal to the optical axis of interrogation is at least as large as 100 microns squared. 111. The device of any of the above aspects, wherein the interrogation region has at least one portion of the region with a depth, measured as the dimension substantially parallel to the optical axis of interrogation, that is sufficiently shallow that the two said macromolecules do not overlap when interrogated. 112. The device of any of the above aspects, wherein the interrogation region has at least one portion of the region with a depth, measured as the dimension substantially parallel to the optical axis of interrogation, that is 195% or less the length of the macromolecule's major axis. 113. The device of any of the above aspects, wherein the interrogation region has at least one portion of the region with a depth, measured as the dimension substantially parallel to the optical axis of interrogation, that is 10 microns or less. 114. The device of any of the above aspects, wherein the interrogation region has at least one portion of the region with a depth, measured as the dimension substantially parallel to the optical axis of interrogation, that is 2 microns or less. 115. The device of any of the above aspects, wherein the interrogation region has at least one portion of the region with a depth, measured as the dimension substantially parallel to the optical axis of interrogation, that is 1 microns or less. 116. The device of any of the above aspects, wherein the capture site is a volume 195% or less that of the package. 117. The device of any of the above aspects, wherein the capture site has a confining dimension that is 195% or less the length of the length of the package's major axis. 118. The device of any of the above aspects, wherein the defined features can be formed with any of the following methods, or combinations there-of: lithography, embossing, injection-molding, 3D printing, nanoimprint, ELB, photolithography, stamping, etching, plasma etching, wet etching, physical etching, lamination, bonding, transfer printing, printing, inkjet printing, dip-pen-lithography, deposition, self-assembly 119. The device of any of the above aspects, wherein the material composition of the device is comprising any of the following: plastic, glass, silicon, elastomers, PDMS, COC, Topaz, PC, PS, silicon, silicon oxide, silicon nitride, borofloat, quartz, fused silica. 120. A method comprising: elongating at least a portion of a long nucleic acid molecule, said molecule labeled with at least two labeling bodies of type A, and labeled with at least two labeling bodies of type B, with A and B having a different fluorescent property, and with the type A labelling bodies comprising a spatial physical map of said molecule, and the type B labelling bodies comprising a spatial physical map of said molecule: where-by the physical map from type A correlates with the physical map from type B with respect to the molecule's spatial nucleic acid density, and the physical map from type A anti-correlates with the physical map from type B with respect to the molecule's spatial nucleic acid genetic content. 121. The method of any of the above aspects, wherein the fluorescent property is excitation wavelength. 122. The method of any of the above aspects, wherein the fluorescent property is emission wavelength. 123. The method of any of the above aspects, wherein the spatial nucleic acid genetic content is the ratio of AT/CG. 124. The method of any of the above aspects, wherein an analysis using both the physical map from type B and the physical map from type A is used to determine variation in the long nucleic acid molecule's spatial nucleic acid density. 125. The method of any of the above aspects, wherein an analysis using both the physical map from type B and the physical map from type A is used to determine variation in the long nucleic acid molecule's spatial genetic content. 126.

The method of any of the above aspects, wherein an analysis using both the physical map from type B and the physical map from type A is used to generate a new linear physical map of the molecule. 127. The method of any of the above aspects, wherein the new physical map associates the molecule's genomic content with the molecule's stretch corrected major axis. 128. The method of any of the above aspects, wherein the new physical map is compared against a reference. 129. The method of any of the above aspects, wherein multiple images of the same molecule are taken at different times, and then these images are processed according to an algorithm to generate a single physical map of the molecule with reduced noise. 130. The method of any of the above aspects, wherein labelling body type A preferentially binds to double-strand nucleic acid, and labelling body type B preferentially binds to single-strand nucleic acid. 131. The method of any of the above aspects, wherein the binding of labelling body type B is done when the molecule is partially melted. 132. The method of any of the above aspects, wherein the partial melting process is comprising the following: heat, salt, organic solvent. 133. The method of any of the above aspects, wherein labelling body type A is comprising: dimeric cyanine nucleic acid stain, POPO-1, BOBO-1, YOYO-1, JOJO-1, POPO-3, LOLO-1, BOBO-3, YOYO-3, TOTO-3. 134. The method of any of the above aspects, wherein labelling body type B is comprising: fluorescently tagged variant of the single-strand DNA binding protein (SSB). 135. The method of any of the above aspects, wherein the dye is comprising: Alexa Fluor 488 (AF488SSB) or 546 (AF546SSB) dye. 136. The method of any of the above aspects, wherein labelling body type B is comprising: a fluorescently tagged variant of replication protein A (RPA) 137. The method of any of the above aspects, wherein labelling body type B is comprising: QuantiFluor, SYBR Green II, OliGreen, 138. The method of any of the above aspects, wherein labelling body type A preferentially binds to AT-rich regions of nucleic acid, and labelling body type B preferentially binds to CG-rich nucleic acid. 139. The method of any of the above aspects, wherein labelling body type A is comprising: quinacrine, Hoescht 33258, Hoechst 33342, DAPI (4,6'-diamidino-2-phenylindole) and diimidazolinophe-nylindole (DIPI), daunomycin 140. The method of any of the above aspects, wherein labelling body type B is comprising: chromomycin A3, olivomycin, mithramycin, 7-amino actinomycin D. 141. The method of any of the above aspects, wherein the two types are bound at the same time. 142. The method of any of the above aspects, wherein the two types are bound sequentially. 143. The method of any of the above aspects, wherein at least a portion of the long nucleic acid molecule is elongated in a fluidic device. 144. The method of any of the above aspects, wherein at least a portion of the long nucleic acid molecule is elongated by combing. 145. A fluidic device comprising of two substantially parallel substrates, in which each substrate contains a conductive material, and between said two substrates is a solution containing at least one body, such that when a time-varying electrical field is applied between the two conductive materials, an attractive force is generated between the two said substrates. 146. The device of any of the above aspects, wherein the dimension that represents the shortest relative distance between the substrates can vary in response to the attractive force. 147. The device of any of the above aspects, wherein at least one substrate is flexible. 148. The device of any of the above aspects, wherein at least one substrate is transparent to at least one wavelength of electromagnetic radiation. 149. The device of any of the above aspects, wherein at least one substrate is conductive. 150. The device of any of the above aspects, wherein at least one conductive material contains ITO. 151. v at least one spacer body is located between the two substrates, and said spacer body's physical conformation defines the local minimum separation distance between the two substrates. 152. The device of any of the above aspects, wherein the spacer body is a bead suspended in solution. 153. The device of any of the above aspects, wherein the spacer body is a bead immobilized on at least one substrate that faces the other substrate. 154. The device of any of the above aspects, wherein the spacer body is a patterned feature on the surface of at least one substrate that faces the other substrate. 155. The device of any of the above aspects, wherein the feature is comprising: pillars, channels, wells, holes, pits, or walls. 156. The device of any of the above aspects, wherein the pattern feature forms an entropic trap to the body when the substrates are brought sufficiently near to each other. 157. The device of any of the above aspects, wherein the time-varying field is comprising at least one frequency component in the range of 1 Hz to 1 GHz 158. The device of any of the above aspects, wherein the body is comprising any of the following: cells, chromosomes, nuclei, vesicles, droplets, nucleic acid, long nucleic acid molecules, proteins, viruses, bacteria, mitochondria, or combination there of. 159. The device of any of the above aspects, wherein the body is captured between the substrates. 160. The device of any of the above aspects, wherein the body is a package, and is ruptured by the attraction of the two substrates. 161. The device of any of the above aspects, wherein application of the attractive force is at least partially controlled via the interrogation of the body between the substrates. 162. An adjustable entropic barrier device comprising an entropic barrier who's energy barrier to a deformable object can be modulated by modulating at least one confining dimension in a fluidic channel in a fluidic device via a mechanism integrated within said fluidic device. 163. The device of any of the above aspects, wherein the modulation of the confining dimension is via a deformable boundary that is comprising at least a portion of the channel, wherein a force is applied to the non-channel facing side of the boundary 164. The device of any of the above aspects, wherein the deformable boundary is an elastomer. 165. The device of any of the above aspects, wherein the force is a pressure is modulated with a liquid. 166. The device of any of the above aspects, wherein the force is a pressure is modulated with a gas. 167. The device of any of the above aspects, wherein the confining dimension can be modulated directly or indirectly via any of the following, including combinations there-of: piezoelectric device, Magnetic polymer composite, Ionically active polymer composite, Magneto rheological fluids, Electro rheological fluids, Dielectric elastomer actuator, Electro strictive ferroelectric polymers, Shape memory polymers, Liquid crystal elastomers, Polymer hydrogels, Conjugated polymers, Phase change materials 168. The device of any of the above aspects, wherein the confining dimension is modulated by an electrostatic attraction between two opposing substrates that form the fluidic channel. 169. The device of any of the above aspects, wherein the adjustable entropic barrier forms part of an adjustable entropic trap for the deformable object within a channel of the fluidic device. 170. The device of any of the above aspects, wherein the capture or release of the deformable object in the trap is determined by some criteria. 171. The device of any of the above aspects, wherein the criteria is determined at least in part by the instrument controller system interrogating the deformable object. 172. The device of any of the above aspects, wherein a water-in-oil droplet containing the deformable object is formed by the displacement of an aqueous solution with an oil solution while the object is in the trap. 173. The device of any of the above aspects, wherein the minimum confining dimension is defined by a patterned feature in the fluidic device. 174. The device of any of the above aspects, wherein control over the confining dimension is determined by an instrument controller system computing a feedback program in which at least one input to said program is data from interrogating the deformable object in the vicinity of the adjustable barrier. 175. A fluidic device in which at least a portion of at least one biological body occupies a fluidic channel containing a phase-changed material such that the body's mobility is either increased or decreased compared to the same condition in which the material is not phase-changed. 176. The device of any of the above aspects, wherein the phase-change material is comprising a photo-rheological fluid whose viscosity can be modified via exposure to electromagnetic radiation. 177. The device of any of the above aspects, wherein the phase-change material is comprising an electro-rheological fluid whose viscosity can be modified via the application of an electric field. 178. The device of any of the above aspects, wherein the phase-change material is comprising a magneto-rheological fluid whose viscosity can be modified via the application of a magnetic field. 179. The device of any of the above aspects, wherein the phase-change material is comprising a sol-gel, who's viscosity can be modified via a change in temperature. 180. The device of any of the above aspects, wherein the sol-get material exhibits a hysteresis in the liquid-to-gel transition. 181. The device of any of the above aspects, wherein the biological body is comprising: packages, cells, droplets, chromosomes, portions of chromosomes, chromatin, long nucleic acid molecule, native nucleic acid, DNA, dsDNA, ssDNA, RNA, virus, BACs, YACs, mRNA, DNA/RNA hybrids. 182. The device of any of the above aspects, wherein the biological body is interrogated while at least partially within the phase-change material. 183. The device of any of the above aspects, wherein the phase-change material is phase-changed before, after, or during the process of interrogation. 184. The device of any of the above aspects, wherein the interrogation is comprising: electro-magnetic, fluorescent, TIRF, epifluorescence, brightfield, darkfield, SEM, TEM, AFM, STM. 185. The device of any of the above aspects, wherein at least one labelling body is bound to the biological body. 186. The device of any of the above aspects, wherein the labeling body is comprising any of the following: A nucleic acid stain or dye, a double-strand nucleic acid stain or dye, a single-strand nucleic acid stain or dye, a karyotyping stain or dye, an AT specific stain or dye, an intercalating dye, a CG specific stain or dye, a FISH probe, a fiber-FISH probe, a methylation fluorescent probe, a fluorescently modified nucleotide, an incorporated fluorescently modified nucleotide, a guiding RNA fluorescent probe, a sequence specific fluorescent probe, a physical mapping labeling body, a linear physical mapping labeling body, a 2D physical mapping labeling body, a 3D physical mapping body, a telomere stain, a fluorescently modified DNA or RNA binding enzyme, a fluorescently modified CRISPR complex, a fluorescent modified DNA or RNA binding agent, a fluorescently modified single-strand DNA binding body. 187. The device of any of the above aspects, wherein the instrument controller system adjusts the degree of phase-change of the material. 188. The device of any of the above aspects, wherein the decision criterion for adjustment is based at least partially on a feedback system of which at least one input is data generated from interrogating the biological body. 189. A fluidic device in which at least a portion of a macromolecule occupies a channel with a tapered cross-section that is contained within a dielectric material and sandwiched between electrodes, such with the application of a time-varying electric field between the electrodes, a dielectrophoretic force is applied on said macromolecule. 190. The device of any of the above aspects, wherein the macromolecule is long nucleic acid molecule. 191. The device of any of the above aspects, wherein the direction of the applied force is towards the point of the taper. 192. The device of any of the above aspects, wherein the direction of the applied force is away from the point of the taper. 193. The device of any of the above aspects, wherein the time-vary electric field is modulated to modulate the direction and magnitude of the force. 194. The device of any of the above aspects, wherein the macromolecule is a long nucleic acid molecule, and the modulation of force is used to modulate the effective degree of physical confinement of the molecule in the taper. 195. The device of any of the above aspects, wherein the portion of the long nucleic acid molecule in the channel is elongated. 196. The device of any of the above aspects, wherein at least a second external force is applied on the macromolecule in a direction that is substantially parallel to a plane that is normal to the DEP force. 197. The device of any of the above aspects, wherein the at least second external force is time varying. 198. The device of any of the above aspects, wherein the at least second external force is an electric field. 199. The device of any of the above aspects, wherein the at least second external force is a fluid flow. 200. The device of any of the above aspects, wherein an instrument control modulates the time-varying electric field. 201. The device of any of the above aspects, wherein the decision criterion for modulation is based at least partially on a feedback system of which at least one input is data generated from interrogating the macromolecule. 202. The device of any of the above aspects, wherein the interrogation data is comprising physical map data from the macromolecule that has been compared to a reference. 203. The device of any of the above aspects, wherein the fluidic solution is comprising a reagent. 204. The device of any of the above aspects, wherein whereby the reagent is an enzyme. 205. The device of any of the above aspects, wherein the enzyme is a protein digestive enzyme. 206. The device of any of the above aspects, wherein the reagent is an MDA primer, primer, a universal primer, a polymerase, a label body. 207. The device of any of the above aspects, wherein at least one labelling body is bound to the macromolecule. 208. The device of any of the above aspects, wherein the labeling body is comprising any of the following: A nucleic acid stain or dye, a double-strand nucleic acid stain or dye, a single-strand nucleic acid stain or dye, a karyotyping stain or dye, an AT specific stain or dye, an intercalating dye, a CG specific stain or dye, a FISH probe, a fiber-FISH probe, a methylation fluorescent probe, a fluorescently modified nucleotide, an incorporated fluorescently modified nucleotide, a guiding RNA fluorescent probe, a sequence specific fluorescent probe, a physical mapping labeling body, a linear physical mapping labeling body, a 2D physical mapping labeling body, a 3D physical mapping body, a telomere stain, a fluorescently modified DNA or RNA binding enzyme, a fluorescently modified CRISPR complex, a fluorescent modified DNA or RNA binding agent, a fluorescently modified single-strand DNA binding body. 209. The device of any of the above aspects, wherein the taper is directed towards the viewing window. 210. The device of any of the above aspects, wherein the taper is directed away from the viewing window. 211. The device of any of the above aspects, wherein the channel with taper is at least partially manufactured via the deposition of a material on a channel. 212. The device of any of the above aspects, wherein the channel with taper is at least partially manufactured via the wet-etching of silicon along a crystal plane to produce an inverted triangle shape. 213. The device of any of the above aspects, wherein the channel with taper is at least partially manufactured via the patterning of a polymer film on a substrate. 214. The device of any of the above aspects, wherein the patterning is done via lithography, photo-lithography, embossing, nanoimprint, imprint, embossing, self-assembly, charge or mold induced shape formation. 215. The device of any of the above aspects, wherein the device is encapsulated via bonding of the tapered channels to a secondary substrate. 216. The device of any of the above aspects, wherein the bonding method is comprising any of the following, or combination there-of: thermal, plasma-activated, anodic, compression, fusion, adhesive, polymer-assisted.

EXAMPLES

Passive Device Examples

Example 1.1 Fabrication of a Passive Device for Cytogenetic Analysis

Figure 7:
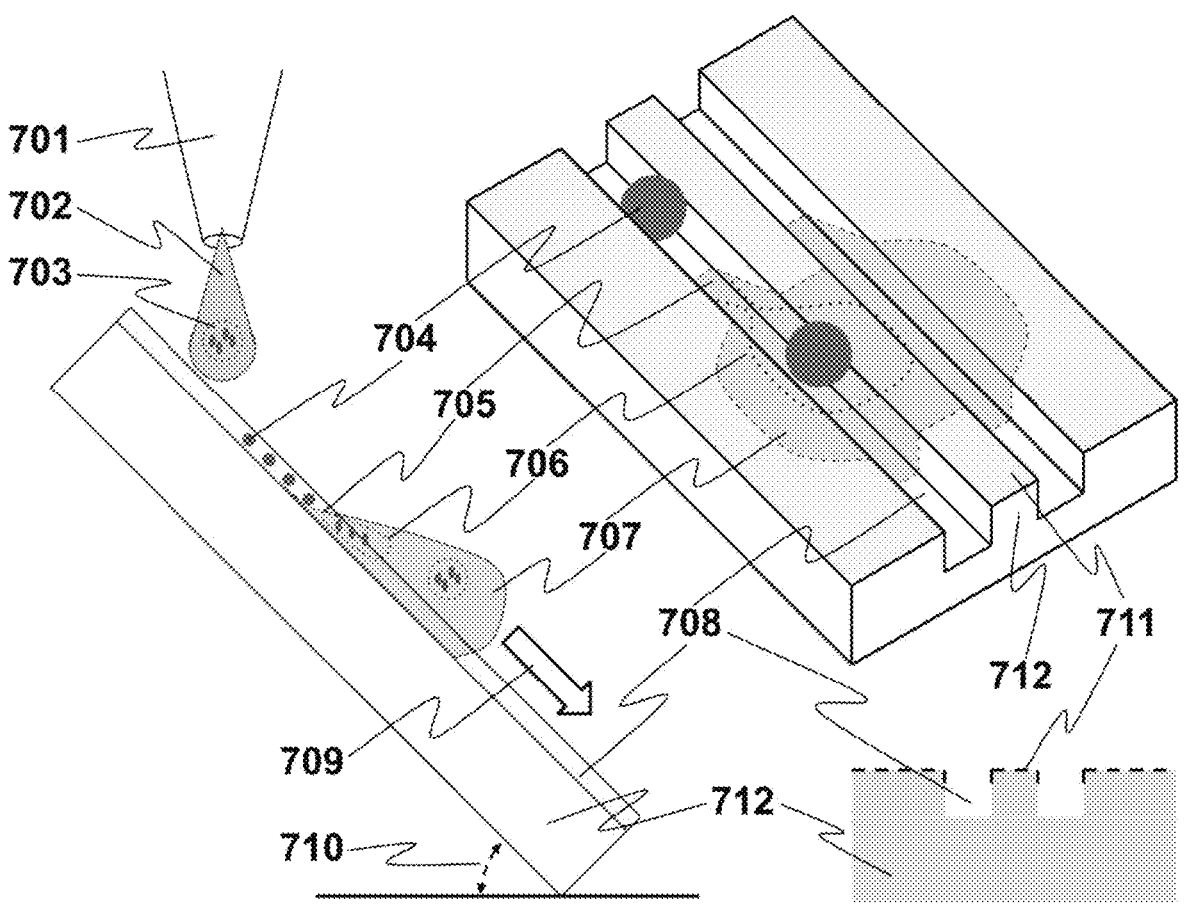
FIG. 7 illustrates a side, cross-sectional, and isometric view of a cytogenetic fluidic device used for generating chromosome spreads for genomic analysis, where-by a solution of packages containing nucleic acid molecules is dispensed via pipette onto the patterned surface features of the device, and the solution is allowed to flow along the patterned surface features of the device via the force of gravity, capillary forces, microconvection forces, surface energy and tension differentials, liquid phase differential, depositing the nucleic acid molecules onto the surface via the receding meniscus of the solution.

As an initial proof of concept, a model system for a passive fluidic device for cytogenetic analysis is developed in a geometry similar to the embodiment shown in FIG. 7. The intended device lateral geometries are first defined using a CAD software program such that contact photomasks can be specified for order from a mask vendor. Once obtained, a glass borofloat wafer 0.5 mm thick is coated with 20 nm of chrome and 100 nm of gold evaporated over the surface of substrate. Next, a layer of positive photoresist is spin coated over the surface, and then prepared for exposure according to the resist manufactures instructions. Operating a mask aligner in contact mode, the resist on the wafer is exposed through the mask to UV light, after which the resist is developed according to the instructions and chemicals recommended by the manufacturer to remove the exposed resist and expose the gold film surface where the channels will be formed. In this example, the channels are 1 micron wide, with pitch of 6 microns. The glass is submerged in a gold and chromium etchant to remove the metal in the channels, followed by an oxygen ash to remove the resist. The glass is submerged in a liquid glass etchant that contains HF and allowed to etch the glass to a depth of 1 micron. The HF wet etch is isotropic, so the channels grow laterally in size by 1 micron after etch, such that after removal of the metal hard masks, the channels in the glass are 3 microns wide, 1 micron deep, with a 3 micron spacing between adjacent channels. The etched glass substrate is then thoroughly washed in a heated mixture of water, ammonia, and hydrogen peroxide to remove any remaining organic material and facilitate particle removal from the surface. Next, fiducial markers for sample dispensing alignment are added by sand-blasting the top surface of the glass substrate through a shadow mask. Then the glass substrate is diced to the form factor of a standard microscope slide, generating several fluidic devices 75 mm×25 mm in size.

Next, the top glass surface is treated with a hydrophobic silane monolayer to silanize the surface. This will both allow for the receding meniscus of solution to wet into the channels, and for containment of solution and sample within the channels. Silane treatment is performed by contact printing against a PDMS film that was previously submerged in a solvent of silane molecules, thus transferring the molecules to the regions between the channels via direct physical contact. The contact printing does not modify the channels, which due to their depressed topography, retain the glass's hydrophilic nature. After a 50 C anneal for 1 hour, the device is ready for use. As designed in this example, the channels are 3 microns wide, and 1 micron deep, suitably sized to accommodate a single human metaphase chromosome lengthwise along the chromosome's major axis.

Example 1.2 Prepare Hypotonic Cells for Karyotyping

Peripheral blood composed of stimulated T cells incubated in a humidified 37° C., 5% CO2 incubator provides a reproducible source for large quantities of mitotic cells, Synchronization of the cell cycle in culture, combined with direct inhibition of chromosome condensation, yield longer high-resolution prophase or prometaphase preparations. Two- or three-day asynchronous cell cultures are blocked by addition of methotrexate (10 μM) to block DNA replication, a folate antagonist that prevents thymidine synthesis. Subsequent addition of thymidine (1 mM) releases a synchronized wave of cells to complete replication and proceed through G2 and into mitosis. Such preparations are used for detailed analysis of microdeletions or subtle rearrangements, fine breakpoint analysis, and refined mapping. Metaphase cells are obtained by treating cultures with Colcemid (10 μg/ml), a colchicine analog that disrupts the centriole/spindle-fiber complex by interfering with microtubule formation. This treatment results in mitotic arrest, which in turn leads to an accumulation of cells in metaphase. Mitotic arrest is followed by treatment with a hypotonic 75 mM KCl solution (hypotonic "shock") to increase cellular volume. The cells are then fixed with 3:1 methanol/acetic acid to remove water and disrupt cell membranes before being applied to a fluidic device.

Example 1.3 Preparation of Sample and Use of Passive Device for Cytogenetic Analysis Chromosome fluidic device preparation: (1) The passive microfluidic device of Example 1.1 is tilted to an angle of 45° (710) to the bench top surface. From a Pasteur pipet (701) 4 inches above the device, drops of fixed cell suspension (702) prepared in Example 1.2 are applied from one end of the device and proceeding toward the other end. Drops (702) strike the tilted device one-third of its width from the elevated long edge, and the drops burst on the device surface and spread out as they strike. This sequence allows excess suspension solution to spread across the surface without pooling on a specific spot of the device, and promotes even meniscus edge (705) dispersal across the device surface, allowing passive local micro-convection flows along the patterned surface features (708) and patterned surface energies (711) to first enrich the settlement and localization of cells then trap, align and elongate the released metaphase chromosomes (704): (2) after application of the cell suspension, the device surface is rinsed with a fixative across the top edge of the device surface. This displaces a front of remaining water across the device surface. It is important to avoid pooling of excess fluid on the surface of the device by blotting the device edge against wet paper towel, and to obtain a thin, even film of fixative to ensure more micro-convection controlled drying.

Devices to be used for fluorescence in situ hybridization (FISH) or karyotyping should be used within several weeks without baking or artificial aging. Because the chromosome preparations on the devices are biodegradable, they should be stored in a clean, dry container in the dark, at room temperature (short-term storage), or frozen at −70° C. (long-term storage).

Next, a G banding physical map is prepared on the metaphase chromosomes spread on the fluidic device. First, the following solutions are added to 4 Coplin jars. Jar #1=30 ml of 1× HBSS and 4 ml of 10× trypsin (0.5%); Jar #2=50 ml of 1× HBSS: Jar #3=45 ml of 1× HBSS and 5 ml of fetal bovine serum: Jar #4=50 ml of 1× HBSS. Second, the device is immersed in Jar #1 for 5 sec, quick rinse in Jar #2, remain in Jar #3 for least 30 sec, quick rinse in Jar #4, then allowed to dry. Third, fresh Giemsa Staining Solution (3:1 ratio of Gurr Buffer and Giemsa Stain) is prepared. The device is placed on a staining rack. The entire device surface is covered in the Giemsa staining solution. The chromosomes are stained for 5 min. Forth, the device is rinsed in distilled water. The device is allowed to dry for about 10 min.

To image the aligned G banded chromosomes, a coverslip is applied with Permount around the edges, and the cells are interrogated with a light microscope under 10× and 100× magnification.

Example 1.4 Preparation of Sample and Use of Passive Device for Cytogenetic Analysis Using the cells in metaphase prepared in Example 1.2, resuspend in loading buffer, the cells suspended in solution are dispensed from a pipette, into the inlet well (907) of the fluidic device shown in FIG. 9(C), resting flat on bench. The patterned surface features (945) and patterned surface energies (943) on the device surface around the loading well promote and enrich the arrangement and localization of cells. Violent shear forces from wetting the device with capillary action ruptures the cells (903), releasing discrete metaphase chromosomes (942) into the patterned fluidics of the interrogation region for analysis.

After being dried, the aligned chromosomes are prepared for G-band karyotyping using the protocol previously described in Example 1.3.

In this example, a bcr/abl translocation structural variant is identified by the physical colocalization of partial bcr gene patterns directly in juxtaposition of partial abl gene locus patterns along the same chromosomal or DNA long molecules, which normally these two gene loci belong to two separate chromosomes of 9 and 22.

Active Device Examples

Example 2.1 Fabrication of Active Device for Cytogenetic Analysis

As an initial proof of concept, a model system for an active fluidic device for cytogenetic analysis is developed in a geometry similar to the embodiment shown in FIG. 14(B). The intended device lateral geometries are first defined using a CAD software program such that contact photomasks can be specified for order from a mask vendor. In this design, the device is optimized for the capture of ~15 micron diameter human white blood cells containing chromosomes in metaphase. The sample loading channel (1431) is 50 microns wide, the package capture sites (1429, 1433) are 15 microns wide, with the laminar flow port (1430) and narrowing connection (1437) are both 2 microns wide. The reaction chamber (interrogation region) (1436) is 10,000 micron-square in area, and the pillars (1435, 1439) are 3 microns in diameter with a closest neighbor spacing of 1 micron.

A double-side polished borosilicate glass wafers (Pyrex 7740) wafer 0.5 mm thick is uniformly coated with an adhesion layer of chromium (20 nm) and seed layer of copper (200 nm), and then a film of photoresist (AZ9260) is coated on the substrate, exposed through the photomask, and developed according to the manufacturers instructions. Nickel is then electroplated to a thickness of 2 microns on the exposed regions of copper, after which the photoresist is removed by solvent and the Cr/Cu plating layer by reactive ion etching (RIE) to expose the glass substrate. The exposed glass substrate masked by the electroplated nickel is then etched in an inductively coupled plasma etcher using a plasma gas mixture of C4F8 and O2 to a depth of 1 micron to define the interrogation regions (1436, 1441) and connecting entropic barriers (1434, 1440, 1443), after which the nickel, copper, and chrome are removed by wet etchants. The process is then repeated to pattern the remaining features, aligning to the first set of features, this time etching to a depth of 15 microns.

With both the fluidic features now patterned in the surface of the glass substrate, the connection points (1421, 1422, 1423, 1424) are connected to fluidic ports by sand blasting through the glass wafer using a metal shadow mask. The glass substrate is then thoroughly washed in a heated mixture of water, ammonia, and hydrogen peroxide to remove any remaining organic material and facilitate particle removal from the surface. Finally, the fluidic device is completed by plasma assisted fusion bonding the patterned glass wafer to a non-patterned glass wafer at 400 C, and then annealed in an oven at 650 C. Once cooled, the wafer is then diced into individual chips, and the fluidic ports are interfaced with a plastic manifold allowing for luer lock connections to all inlet and outlet ports.

Example 2.2 Preparation of Cells for Loading into Fluidic Device

As an initial proof of concept, the following protocol is followed to prepare peripheral blood cells for loading into an active fluidic device. Peripheral blood is collected by venipuncture into a sodium heparin Vacutainer with 25 U preservative-free sodium heparin per milliliter of blood. Blood in sodium heparin is held for up to 4 days at 4° C. Next, 0.25 ml of the whole blood is inoculated into a sterile 15-ml centrifuge tube containing 5 ml complete RPMI/10% FBS medium, using a TB syringe equipped with a 21-G needle. 0.05 ml of reconstituted 100× PHA solution is added. A single culture typically yields three to five full-slide preparations. The tubes are incubated 3 days tilted at 45° in order to promote air exchange. Note: older patients' leukocytes require up to 4-day cultures because they do not respond as quickly to PHA stimulation. If larger cultures are desired, they can be grown in T25 flasks using a similar ratio of blood to media. The protocol in Example 1.2 for metaphase cell preparation is then followed. The cell suspension is mixed 1:1 with FACSFlow buffer (BD Bioscience), centrifuged at 400 rpm for 5 minutes and resuspended in FACSFlow. Finally, Live cells are stained with CellBrite® Green: Ex/Em 484/501 nm.

Example 2.3 Preparation of Sample and Use of an Active Device for Cytogenetic Analysis The active fluidic device demonstrated in Example 2.1 based on FIG. 14 is mounted on a holder allowing for interfacing with fluidic tubing for solution exchange within the device and an optical microscope for interrogation. Fluorescence imaging is performed using an inverted microscope equipped with a 60×/1.00 water immersion objective and an SCMOS camera. The temperature inside the device is controlled by a heater held in contact with the backside of the device.

Prior to receiving the cells, the device is flushed by 1% sodium dodecyl sulfate, buffer solution (0.5 TBE, 3% b-mercaptoethanol (BME) and 0.5% Triton X-100) and BSA at 1 mg/mL for 10 minutes.

A solution containing cells (1425) prepared in Example 2.2 is introduced to the fluidic device at an inlet port (1421) of the sample loading channel (1431) and flowed towards the outlet port (1422) until a cell is confirmed captured at the capture site (1429) by fluorescent imaging the stained cell. Next, an alkaline lysing solution is flowed from the inlet port (1421) to the secondary outlet port (1424), which releases the metaphase chromosomes, and once released, flows the chromosomes through the narrowing connection (1437) into the reaction chamber (1436). With the chromosomes in the reaction chamber, their vertical height is now confined to 1 micron, requiring the chromosomes to distribute through the chamber in a non-overlapping manner. Next the chromosomes are prepared for interrogation by flowing reagents from the secondary inlet port (1423) to the secondary outlet port (1424) at a rate of 1-10 nL/min. These regents include proteinase K to digest the DNA binding proteins, RNase to digest RNA, and YOYO-1 to stain the chromosomes (all reagents from Thermo Fisher). All digested molecules, and non-chromosome material, and excess reagent is washed to the exit port, with the entropic barrier maintaining the chromosomes in the reaction chamber. Times and concentrations of protein digestion are per the manufacturer's instructions. With protein digestion complete, a physical melt map is generated on the chromosomes by controlled heating of the device to the desired protocol as previously described [Tegenfeldt, 2009, U.S. Pat. No. 10,434,512], while maintaining a solution flow to rinse away the released YOYO to the outlet port (1424). Finally, the chromosomes are suitably arranged within the chamber with the application of a time-varying electric field in the range of −30 to +30 Volts applied between the inlet port (1423) and outlet port (1424). The swelled, non-overlapping chromosomes with AT/CG YOYO melt map are then imaged.

Example 2.4 Selectively Karyotyping Circulating Tumor Cells from Blood Samples The fluidic device demonstrated in FIG. 15 is fabricated using the methods described in Example 2.1. The device is optimized for screening large numbers of cells, and contains an array of 16 interrogation regions (1515) each connected to 64 cell capture sites (1508). The interrogation regions are arrayed in series, separated by entropic traps. The device sits in a nest in an inverted microscope which contains several fluorescence channels, brightfield excitation and a fluidic interface to control the ingress and egress of fluids from the device. A 60× 1.4 NA oil immersion objective is used. The system additionally contains a 100 mW 405 nm laser diode (Obis LX, Coherent) which is expanded into an elongated beam with a 1:6 aspect ratio and 10 mm 1/e2 beam waist along the widest portion. The beam is launched through the objective on axis to create a focused line 1.3 um×0.22 um at the sample.

A blood sample is taken from a patient and enriched for potential CTCs using a commercially available microfluidic sorter (Parsortix, Angle plc) and eluted per manufacturer's protocol. Eluted cells are cultured and cell cycle arrested as described in Example 2.2. Cells are stained using a mixture of Alexa 488 labelled anti Cytokeratin antibody, Alexa594 labelled anti CD45 antibody, and DAPI, and harvested.

The stained cells are introduced through the device and flowed along the Sample Loading Channel (1503) from port 1501 to port 1502 using pressure driven flow. The sample is observed under brightfield microscopy and flow is stopped when approximately 3/4 of the traps are filled with cells. Cells are then imaged for all three fluorophores and CTC candidates are selected for interrogation based on fulfillment of all three criteria: (a) presence of a nucleus (b) positive for Cytokeratin and (c) negative for CDC45. For each interrogation area, a single cell (if any) is selected. If multiple cells pass the selection criteria, they are ranked by the ratio of Cytokeratin to CD45 fluorescence.

Once a cell is selected for interrogation, it is selectively photolyzed by translating the stage to position the focus of the 405 nm laser at the interface of the cell trap and the narrowing connection (1508/1516), with the orientation of the elongated laser focus parallel to the sample inlet channel. The location of the laser is placed over the portion of the cell membrane that points towards the interrogation channel and gentle fluid flow is initiated from 1501 to port 1521. The 405 nm laser is pulsed for 1.0 s to disrupt the membrane [Paterson, 2005] and allow the cell contents to move into the interrogation region. Lysis is repeated for other cells of interest in each interrogation region.

Chromosomes in the interrogation regions are stained as per Example 1.3, but instead of dipping a slide in a Coplin jar containing a reagent, the reagents are flowed through the common interrogation channel 1520-1521. Prior to imaging, cells are flushed off of the entropic barriers separating the interrogation regions by reversing the flow through the interrogation channel then applying a sinusoidal fluidic pulsing to distribute the chromosomes throughout the interrogation region. Images of chromosome G banding are saved alongside fluorescence images of the antibody fluorescence of the intact cell.

Example 2.5 Manufacture of a DEP Device

As an initial proof of concept, a model system for a DEP device is developed in a geometry similar to the embodiment shown in FIG. 27. Two glass substrates (A and B) are coated with a 100 nm layer of conductive ITO film, with the "top" substrate (A) then coated with 1 micron thick film of COC, while the "bottom" substrate (B) coated with a 0.2 micron thick film of COC. An embossing mold is prepared by first wet etching with KOH a silicon wafer to expose the {111} crystal planes as described by [Frühauf, 2005] to generate a triangle grating. Second the silicon surface is thermally oxidized to a thickness of 10 nm, and on the silicon oxide surface a self-assembled silane based hydrophobic monolayer is prepared to allow for mold release. The triangle grating mold has a pitch of 2.2 microns, with a depth of 1.6 microns. The mold is used to emboss the triangle pattern into the COC film of substrate A by applying pressure and heat above the COC's glass transition temperature. The COC will flow and conform to mold, leaving a 0.2 micron thick COC separation from the triangle tip (taper) and the ITO film. Finally, the COC coated sides of substrates A and B are brought into contact, and the with applied pressure and heat, the substrates are bonded, producing confined channels with a taper within a dielectric material (COC).

Example 2.6 Differential Melt Map Protocol

The device shown in FIG. 22 is used. Prior to chromosome loading, the device is washed with 0.1% Tween-20 and the sample is incubated with YOYO-1 at sufficient concentration to achieve a 1:5 dye to basepair ratio. The sample is loaded and processed, resulting in portions of the chromosome extending into the elongation channel of the interrogation region. The device is held onto a microscope stage by means of a temperature regulated nest containing Peltiers, thermocouples for active feedback and a precise controller (TEC-1089-SV, Meerstetter).

A differential staining buffer is gently flowed into the device and the temperature is increased to melt approximately 50% of the DNA. The buffer does not contain YOYO-1 but does contain a fluorescent thermostable Single Strand Binding Protein (SSB) (origin: *Thermotoga maritima*, expressed in *E. coli* with point mutation S116C and Maleimide labeled with Atto647N). Temperature is held at the melting point for 60s before ramping down to 20 C at a ramp rate of 2C/s. Imaging buffer (0.5× TBE, 0.1% Tween-20, 1 mM B-Mercaptoethanol) is flowed into the device to wash out excess fluorescent SSB and YOYO-1.

DNA is imaged in two fluorescence channels in quick succession to minimize DNA movement between images. LED excitation for YOYO-1 is accomplished by operating a single diode (GV QSSPA1.13, OSRAM) in Koehler illumination, with the LED die imaged to the back aperture of the objective (60× 1.4 NA) with 7× magnification. LED excitation for Atto647N is accomplished likewise (KS DMLS31.23, OSRAM) with 9× magnification.

The DNA backbone is identified computationally and a trace of the intensity profiles is generated in each channel. The traces are background subtracted and a cumulative brightness histogram is generated for each channel. The traces are normalized by their 80th percentile brightness value. The ratio of the normalized YOYO intensity to the sum of the normalized YOYO plus the normalized SSB-Atto647N is computed as a best estimate of GC content and the physical map of the DNA strand under analysis.

The physical map is compared with a pre-computed reference physical maps that are derived from sequences of the human genome assembly GRCh37 analyzed for melting state by the method of [Tostesen, 2005]. Reference map segments are sampled at intervals corresponding to one pixel of detected image and each pixel worth of GC ratio information is normalized as a signed 8 bit integer, where −128 represents 100% AT, 127 represents 100% GC. The reference map is pre-computed for a variety (up to 20) DNA stretch ratios, so the same sequence is present multiple times. Observed maps are compared with the physical map references in two steps, first each molecule is artificially segmented into 32 pixel segments starting every other pixel. This corresponds to approximately 8-13 kbp depending on DNA stretch. The dot product of each segment and a 32 pixel tile of the reference map segments is computed. The top 4k matches are passed to the second stage, which repeats the dot product on neighboring regions in both the map and the sample and scores them with a Smith-Waterman algorithm to permit local insertions and deletions. Detection cutoffs are determined empirically.

We claim:

1. A method comprising: elongating at least a portion of a long nucleic acid molecule, said molecule labeled with at least two type A labeling bodies having a first fluorescent property, and labeled with at least two type B labeling bodies having a second fluorescent property, and with the type A labelling bodies indicating a first spatial physical map of said molecule, and the type B labelling bodies comprising a second spatial physical map of said molecule; wherein the first physical map correlates with the second physical map with respect to spatial nucleic acid density of the long nucleic acid molecule, and wherein the first physical map anti-correlates with the second physical map with respect to spatial nucleic acid genetic content of the long nucleic acid molecule.

2. The method of claim 1 wherein the spatial nucleic acid genetic content is the ratio of AT/CG.

3. The method of claim 1 wherein labelling body type A preferentially binds to double-strand nucleic acid, and labelling body type B preferentially binds to single-strand nucleic acid.

4. The method of claim 1 wherein labelling body type A preferentially binds to AT-rich regions of nucleic acid, and labelling body type B preferentially binds to CG-rich nucleic acid.

5. The method of claim 1 wherein at least a portion of the long nucleic acid molecule is elongated in a fluidic device.

6. The method of claim 1 wherein at least a portion of the long nucleic acid molecule is elongated by combing.

* * * * *